United States Patent
Stover et al.

(10) Patent No.: US 11,744,874 B2
(45) Date of Patent: Sep. 5, 2023

(54) FORMULATED AND/OR CO-FORMULATED LIPOSOME COMPOSITIONS CONTAINING TOLL-LIKE RECEPTOR ("TLR") AGONIST PRODRUGS USEFUL IN THE TREATMENT OF CANCER AND METHODS THEREOF

(71) Applicant: Nammi Therapeutics, Inc., Los Angeles, CA (US)

(72) Inventors: David Stover, Encino, CA (US); Dhruba Bharali, Sherman Oaks, CA (US); Bruce A Hay, Niskayuna, NY (US); Tahmineh Safaie, Los Angeles, CA (US)

(73) Assignee: Nammi Therapeutics, Inc., Los Angeles, CA (US)

( * ) Notice: Subject to any disclaimer, the term of this patent is extended or adjusted under 35 U.S.C. 154(b) by 260 days.

(21) Appl. No.: 16/974,306

(22) Filed: Dec. 21, 2020

(65) Prior Publication Data
US 2021/0187066 A1    Jun. 24, 2021

Related U.S. Application Data

(60) Provisional application No. 62/974,746, filed on Dec. 20, 2019.

(51) Int. Cl.
*A61K 47/54*    (2017.01)
*A61K 47/69*    (2017.01)
(Continued)

(52) U.S. Cl.
CPC .......... *A61K 38/177* (2013.01); *A61K 45/06* (2013.01); *A61K 47/543* (2017.08); *A61K 47/6911* (2017.08)

(58) Field of Classification Search
None
See application file for complete search history.

(56) References Cited

U.S. PATENT DOCUMENTS 7,576,068 B2    8/2009    Averett
8,034,802 B2    10/2011    Averett
(Continued)

FOREIGN PATENT DOCUMENTS

EP    2322178 A3    5/2011
WO    WO2009/030996 A1    3/2009
(Continued)

OTHER PUBLICATIONS

Engel, et. al., The Pharmacokinetics of Toll-like receptor agonsits and the impact on the Immune System, Expert Rev. Clin. Pharmacol, 4(2): 275-289 (Mar. 2011).
(Continued)

*Primary Examiner* — Nissa M Westerberg
(74) *Attorney, Agent, or Firm* — LOSMP; Shane M. Popp

(57) ABSTRACT

Formulated and/or co-formulated liposomes comprising TLR prodrugs and/or TLR Lipid Moieties and methods of making the liposomes are disclosed herein. The TLR prodrug compositions comprise a drug moiety, a lipid moiety, and linkage unit that inhibit Toll-Like Receptor (e.g., TLR1/2, TLR4, and/or TLR7). The TLR prodrugs can be formulated and/or co-formulated into a liposome to provide a method of treating cancer, immunological disorders, and other disease by utilizing a targeted drug delivery vehicle.

9 Claims, 29 Drawing Sheets

(51) Int. Cl.
*A61K 31/4164* (2006.01)
*A61K 38/17* (2006.01)
*A61K 45/06* (2006.01)

(56) References Cited

U.S. PATENT DOCUMENTS

| | | |
|---|---|---|
| 8,211,863 B2 | 7/2012 | Averett |
| 8,343,497 B2 | 1/2013 | Shi et al. |
| 8,343,498 B2 | 1/2013 | Alexis et al. |
| 8,367,670 B2 | 2/2013 | Desai et al. |
| 8,535,683 B2 | 9/2013 | Kersten et al. |
| 8,562,998 B2 | 10/2013 | Shi et al. |
| 8,591,905 B2 | 11/2013 | von Andrian et al. |
| 8,629,142 B2 | 1/2014 | Desai et al. |
| 8,808,703 B2 | 8/2014 | Wu et al. |
| 8,809,527 B2 | 8/2014 | Desai et al. |
| 9,045,470 B2 | 6/2015 | Wu et al. |
| 9,228,184 B2 | 1/2016 | Guiducci et al. |
| 9,233,141 B2 | 1/2016 | Chakraborty et al. |
| 9,255,111 B2 | 2/2016 | An et al. |
| 9,308,239 B2 | 4/2016 | Thiboutot et al. |
| 9,452,166 B2 | 9/2016 | Desai et al. |
| 9,517,993 B2 | 12/2016 | Yin et al. |
| 9,676,818 B2 | 6/2017 | Salunke et al. |
| 9,750,803 B2 | 9/2017 | Irvine et al. |
| 10,030,067 B2 | 7/2018 | Golde et al. |
| 10,172,860 B2 | 1/2019 | Desai et al. |
| 10,335,486 B2 | 7/2019 | Frederick et al. |
| 10,414,789 B2 | 9/2019 | Debensky, Jr. et al. |
| 10,799,580 B2 | 10/2020 | Seder et al. |
| 10,973,917 B2 | 4/2021 | Frederick et al. |
| 2003/0232074 A1 | 12/2003 | Lipford et al. |
| 2006/0172966 A1 | 8/2006 | Lipford et al. |
| 2009/0214578 A1 | 8/2009 | Bauer |
| 2009/0215710 A1 | 8/2009 | Upadhyay et al. |
| 2009/0297533 A1 | 12/2009 | Lichter et al. |
| 2009/0306177 A1 | 12/2009 | Uhlmann et al. |
| 2010/0129439 A1 | 5/2010 | Alexis et al. |
| 2010/0130425 A1 | 5/2010 | Stenzel-Poore et al. |
| 2011/0077263 A1 | 3/2011 | Kast et al. |
| 2012/0148660 A1 | 6/2012 | Carson et al. |
| 2013/0156807 A1 | 6/2013 | Carson et al. |
| 2013/0202629 A1 | 8/2013 | Carson et al. |
| 2013/0230578 A1 | 9/2013 | Wightman |
| 2013/0266584 A1 | 10/2013 | Schuppan et al. |
| 2014/0135487 A1 | 5/2014 | Lipfoed et al. |
| 2014/0161725 A1 | 6/2014 | Morse et al. |
| 2014/0302120 A1 | 10/2014 | Carson et al. |
| 2015/0147276 A1 | 5/2015 | Ingber et al. |
| 2015/0225432 A1 | 8/2015 | Cortez et al. |
| 2015/0251987 A1 | 9/2015 | Yin et al. |
| 2016/0175433 A1 | 6/2016 | Wightman |
| 2016/0194381 A1 | 7/2016 | Thiboutot et al. |
| 2016/0347791 A1 | 12/2016 | Caligiuri et al. |
| 2017/0095573 A1 | 4/2017 | Oh et al. |
| 2017/0182152 A1 | 6/2017 | Alving et al. |
| 2017/0189521 A1 | 7/2017 | Wightman |
| 2017/0333553 A1 | 11/2017 | Wightman |
| 2018/0085445 A1 | 3/2018 | Chow et al. |
| 2018/0200364 A1 | 7/2018 | Wightman |
| 2018/0280497 A1 | 10/2018 | Seder et al. |
| 2018/0326051 A1 | 11/2018 | Wightman |
| 2018/0344641 A1 | 12/2018 | Brinker et al. |
| 2019/0119341 A1 | 4/2019 | Ramsburg et al. |
| 2019/0275135 A1 | 9/2019 | Poolman |
| 2020/0030441 A1 | 1/2020 | Wightman |
| 2020/0085850 A1 | 3/2020 | Sherwood et al. |
| 2020/0276299 A1 | 9/2020 | Fox et al. |
| 2020/0330581 A1 | 10/2020 | Black |
| 2020/0375912 A1 | 12/2020 | Serda et al. |
| 2021/0017189 A1 | 1/2021 | Cheng et al. |
| 2021/0179621 A1 | 6/2021 | Yin et al. |
| 2022/0096630 A1 | 3/2022 | Frederick et al. |

FOREIGN PATENT DOCUMENTS

| | | |
|---|---|---|
| WO | WO2009/030998 A1 | 3/2009 |
| WO | WO2011/085981 A1 | 7/2011 |
| WO | WO2014/201245 A1 | 12/2014 |
| WO | WO2015/000022 A1 | 1/2015 |
| WO | WO2015/171951 A1 | 11/2015 |
| WO | WO2017/070735 A1 | 5/2017 |
| WO | WO2018/213631 A1 | 11/2018 |

OTHER PUBLICATIONS

Cen, et. al., TLR1/2 Specific Small-Molecule Agonsist Suppresses Leukemia Cancer Cell Growth by Stimulating Cytotoxic T Lymphocytes, Adv. Sci. 6, pp. 1-12 (2019).

Nakamura, et. al., Synthesis and evaluation of 8-oxoadenine derivatives as potent toll-like receptor 7 agonsists . . . , Bioorg. & Med. Chem. Letters 23 (2013) pp. 669-672.

Kurimoto, et. al., Synthesis and Structure-Activity Relationships of 2-Amino-8-hydroxyadenines as orally . . . Bioorg. & Med. Chem. 11 (2003) pp. 5501-5508.

Basith, et. al., Toll-like Receptor Modulators: A Patent Review (2006-2010), Expert Opin. Ther. Patents (2011) 21(6) pp. 927-944.

Rodell, et. al., TLR7/8-agonist-loaded nanoparticles promote the polarization of tumour-associated . . . Nat. Biomed. Eng. 2:578-588 (2018).

Offermanns, et. al., Lipopeptides are Effective Stimulators of Tyrosine Phosphorylation in Human Myeloid Cells, Biochem J. 282, pp. 551-557 (1992).

Nguyen, et. al., The Synthetic Bacterial Lipopeptide Pam3CSK4 Modulates Respiratory Syncytial Virus . . . , Plos Pathogens vol. 6, Issue. 8 pp. 1-13 (Aug. 2010).

Mura, et. al., Lipid Prodrug Nanocarriers in Cancer Therapy, J. Controlled Release, 208 pp. 25-41 (2015).

Smirnov, et. al., Vaccine Adjuvant Activity of 3M-052: An imidazoquiniline designed for local activity without . . . , Vaccine (2011), doi: 10.1016/j.vaccine.2011.05.061.

Macedo, et. al., Targeting Cellular and Tissue HIV Reservoirs With Toll-Like Receptor Agonists, Frontiers in Immunology, vol. 10, Art. 2450 (Oct. 2019).

Genito, et. al., Liposomes Containing Monophosphoryl Lipid A and QS-21 Serve as an Effective Adjuvant for Soluble, Vaccine 35 (2017) pp. 3865-3874.

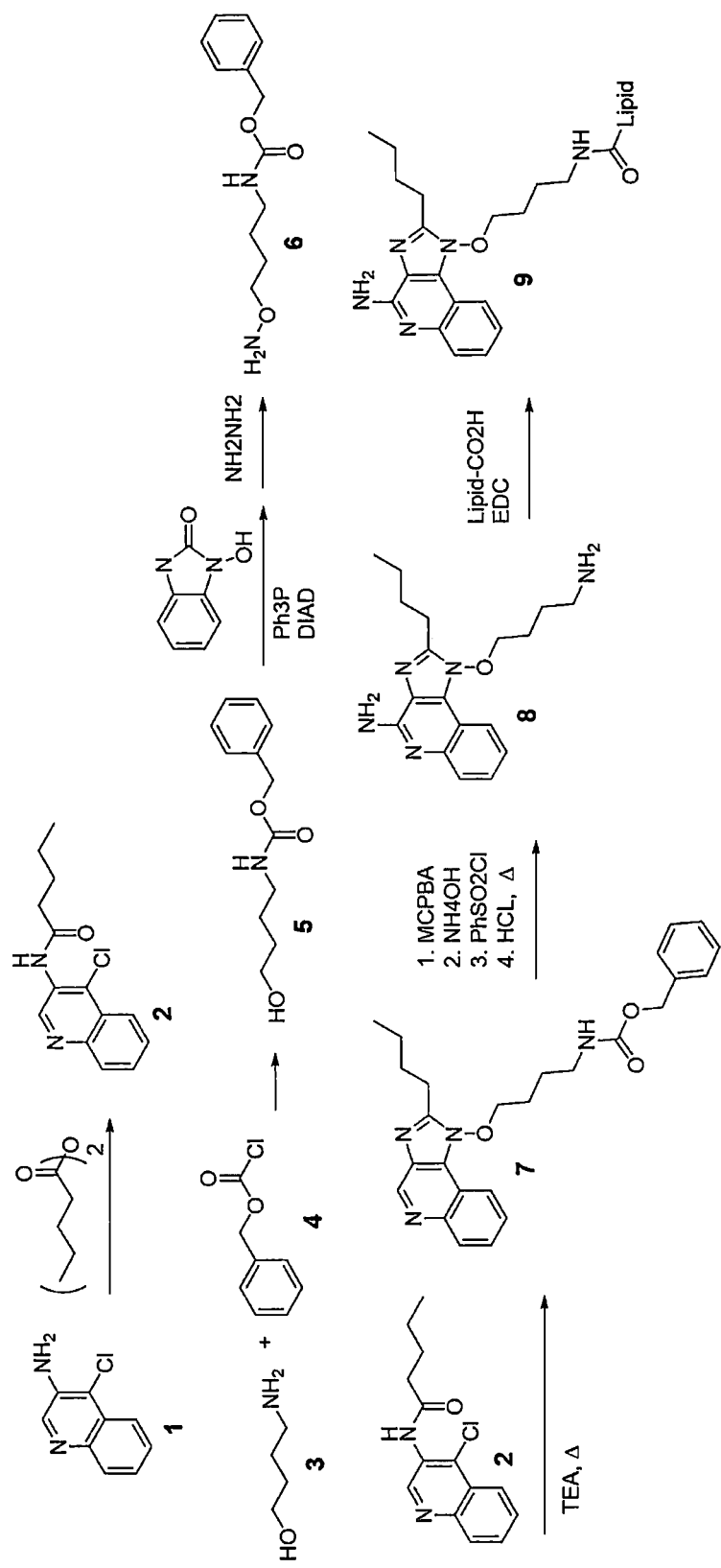
Figure 1. General Chemical Synthesis for TR5(B)

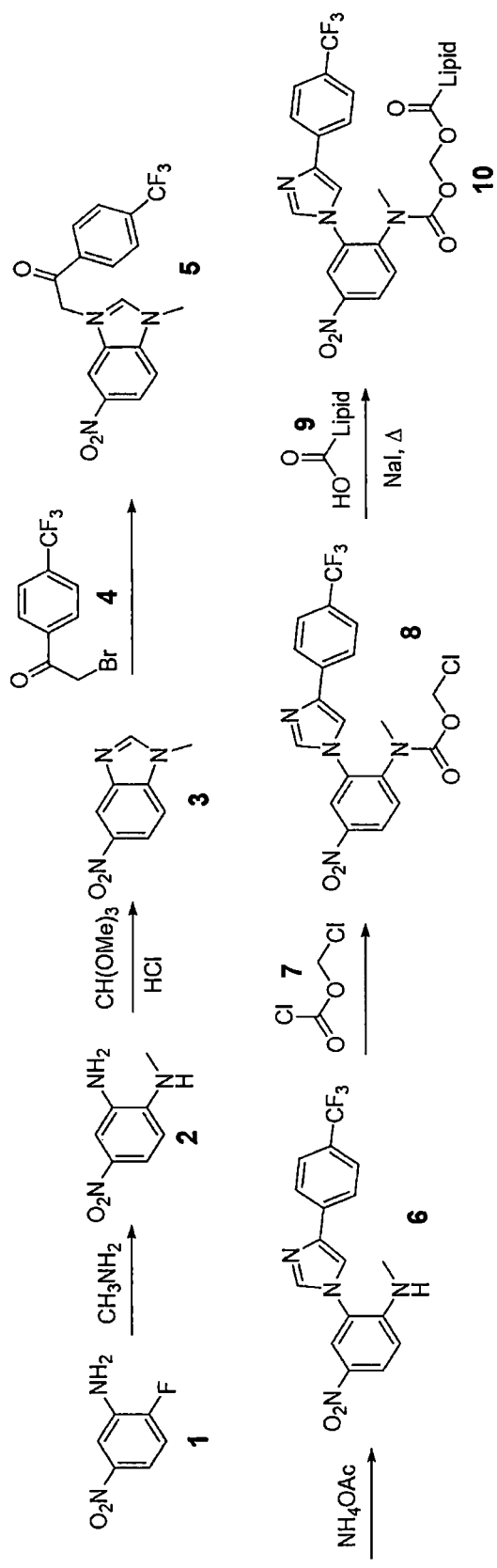
Figure 2. General Chemical Synthesis for TR6

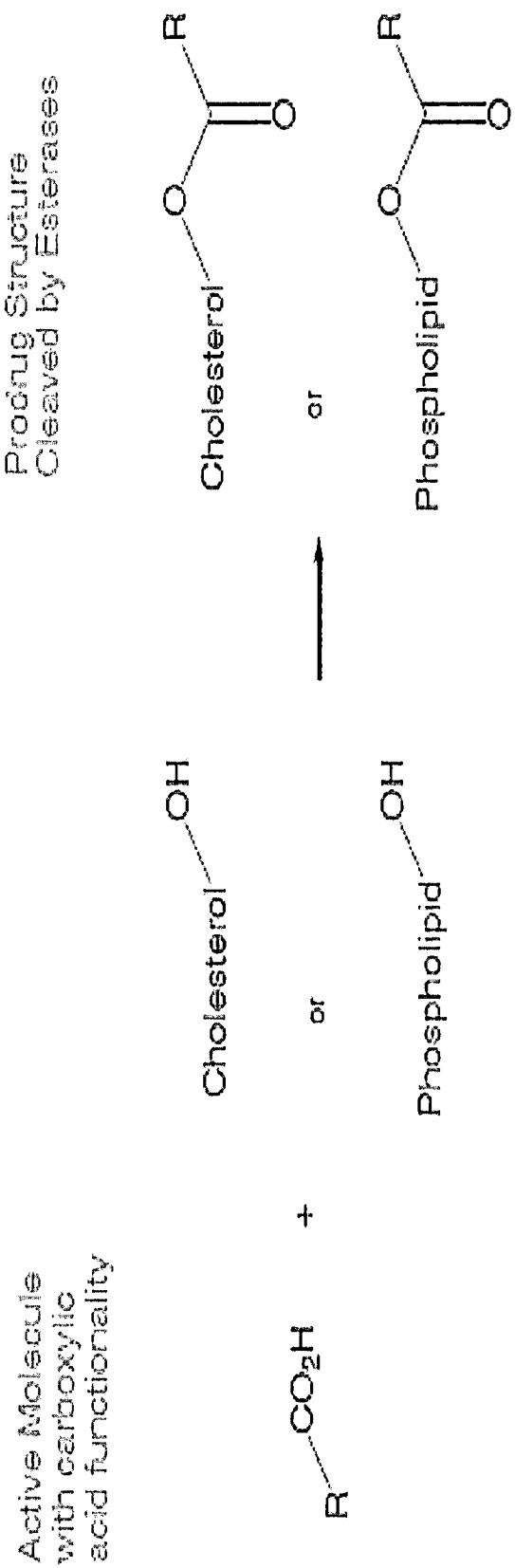
Figure 3. TLR Inhibitor Prodrug Synthesis Schema with Carboxylic Acid Functionality Figure 4. TLR Inhibitor Prodrug Synthesis Schema with Alcohol Functionality
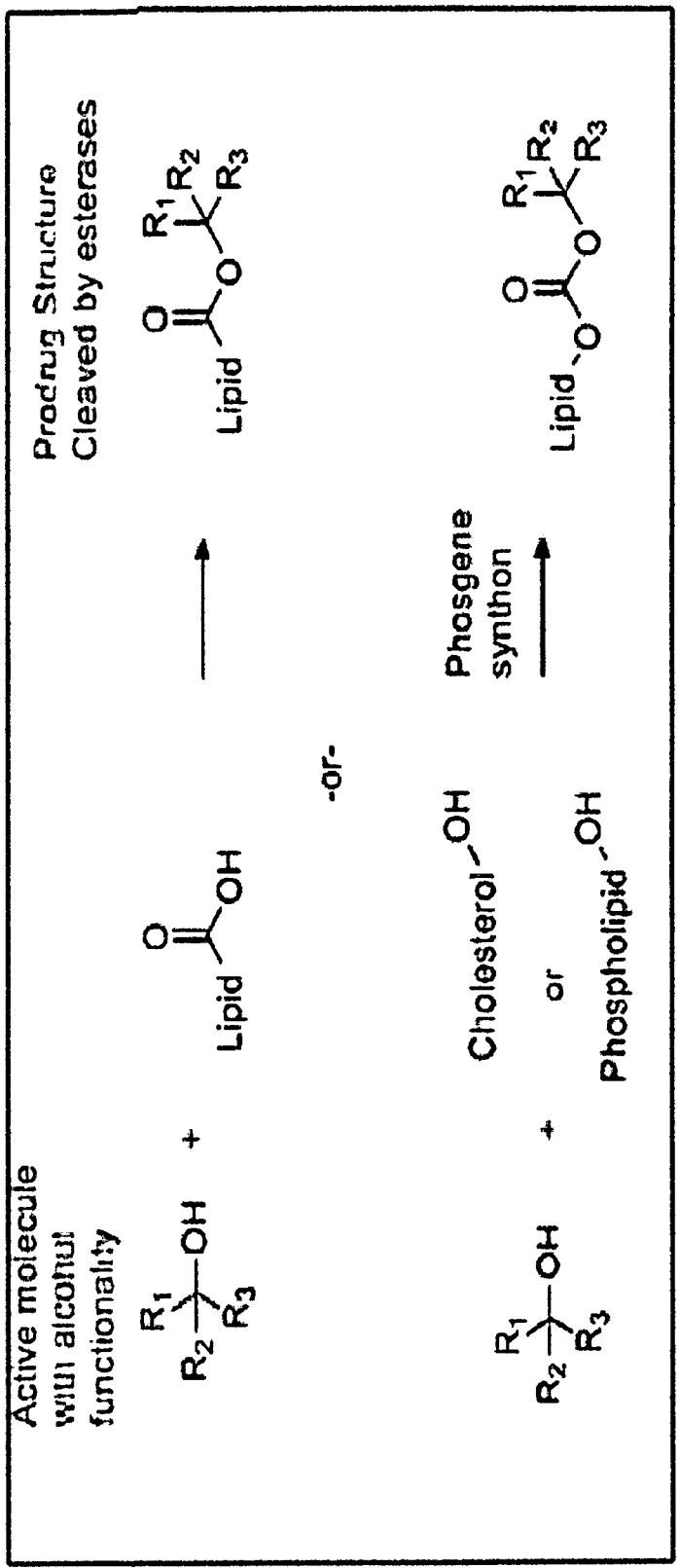

Figure 5. TLR Inhibitor Prodrug Synthesis Schema with Secondary Amine, Amide, or Aniline Functionality
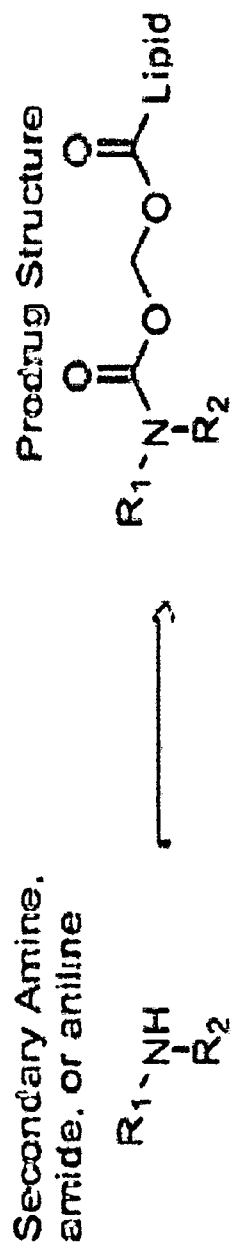

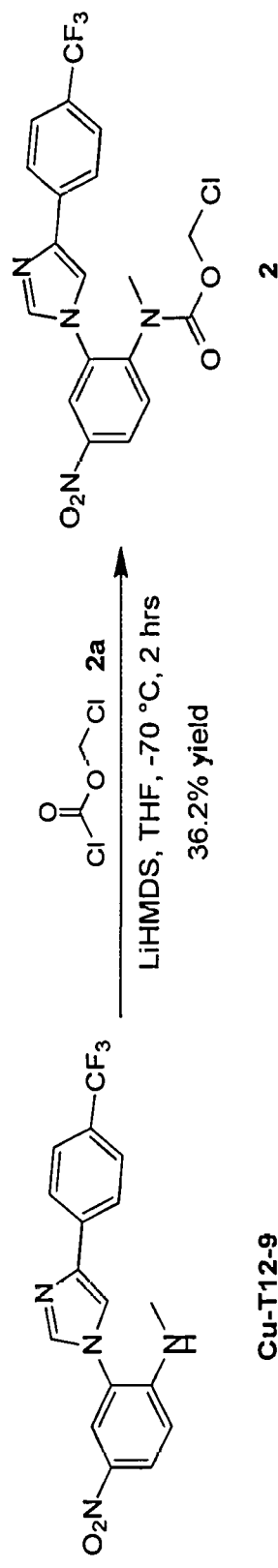
Figure 6. Chemical Synthesis for TR6 Prodrug Intermediate

Figure 7. Chemical Synthesis for TR6 Prodrug Comprising CHEMS
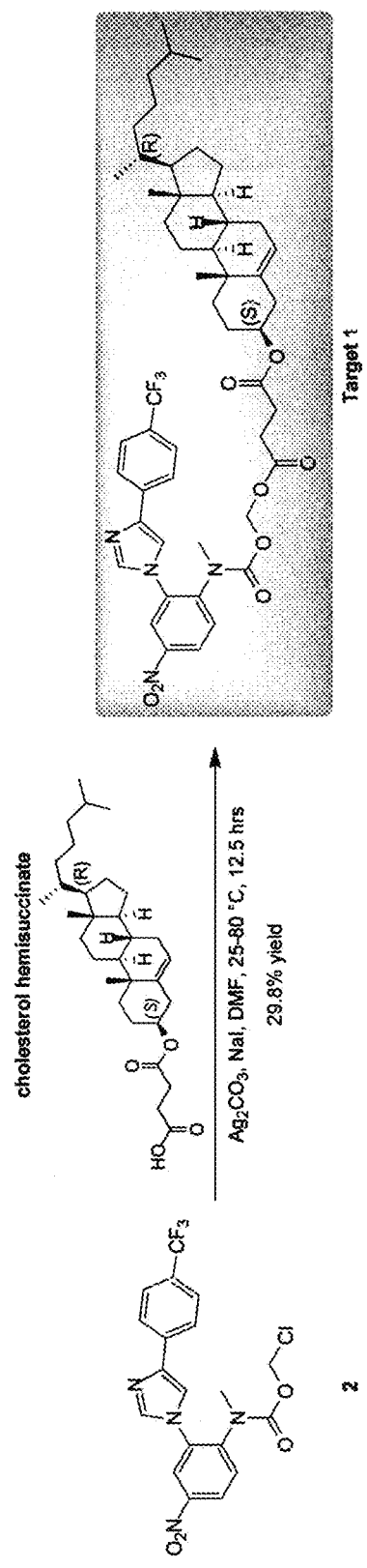

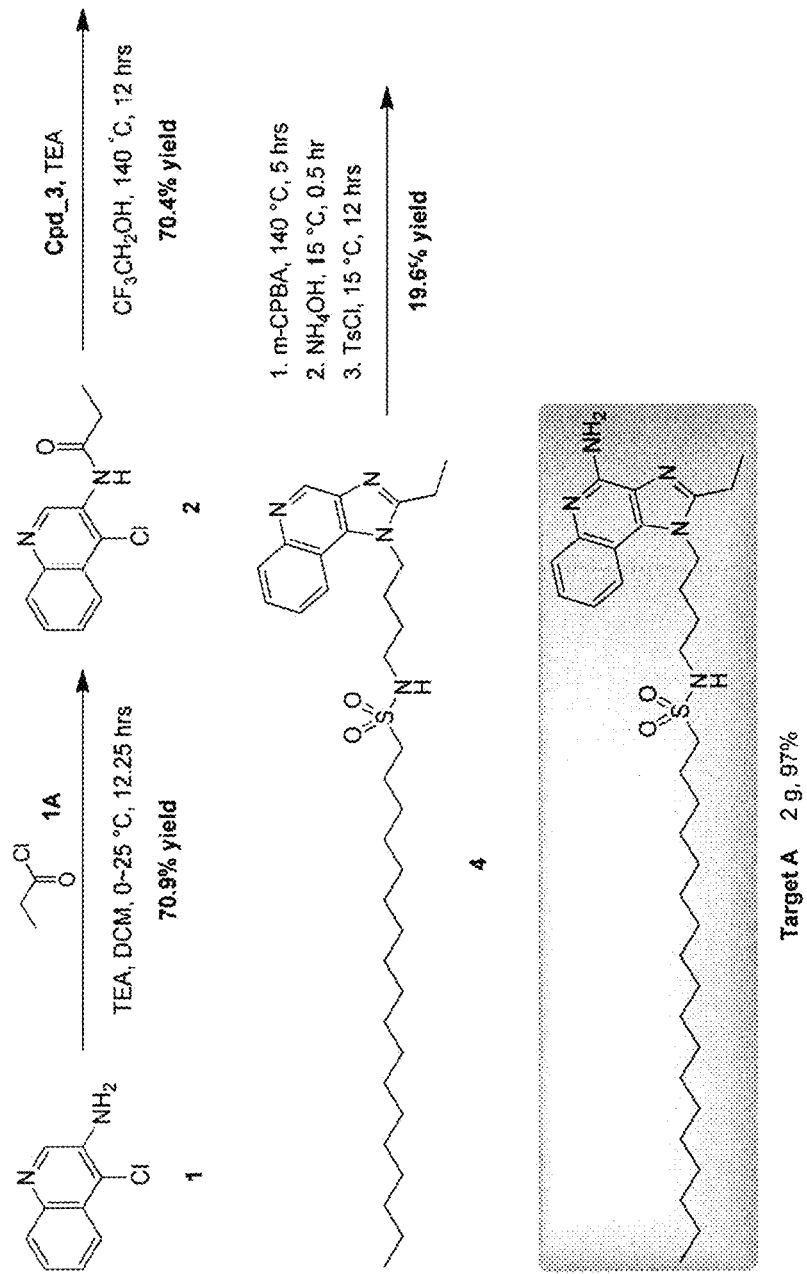
Figure 8. Chemical Synthesis for TR3

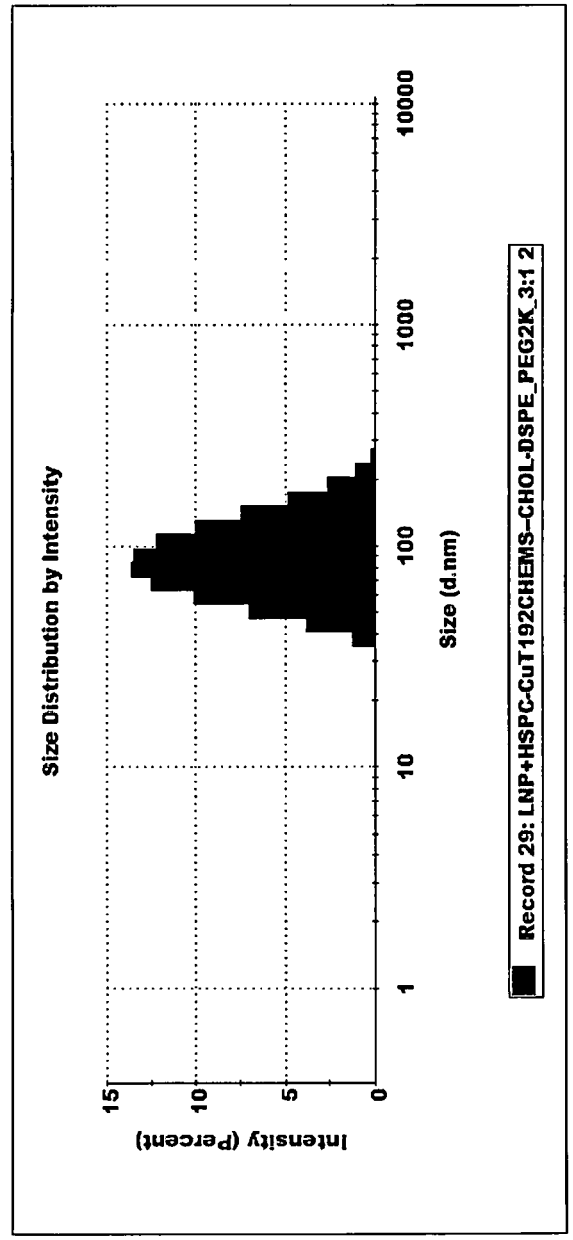
Figure 9. Characterization of LNP-TR6 Liposome

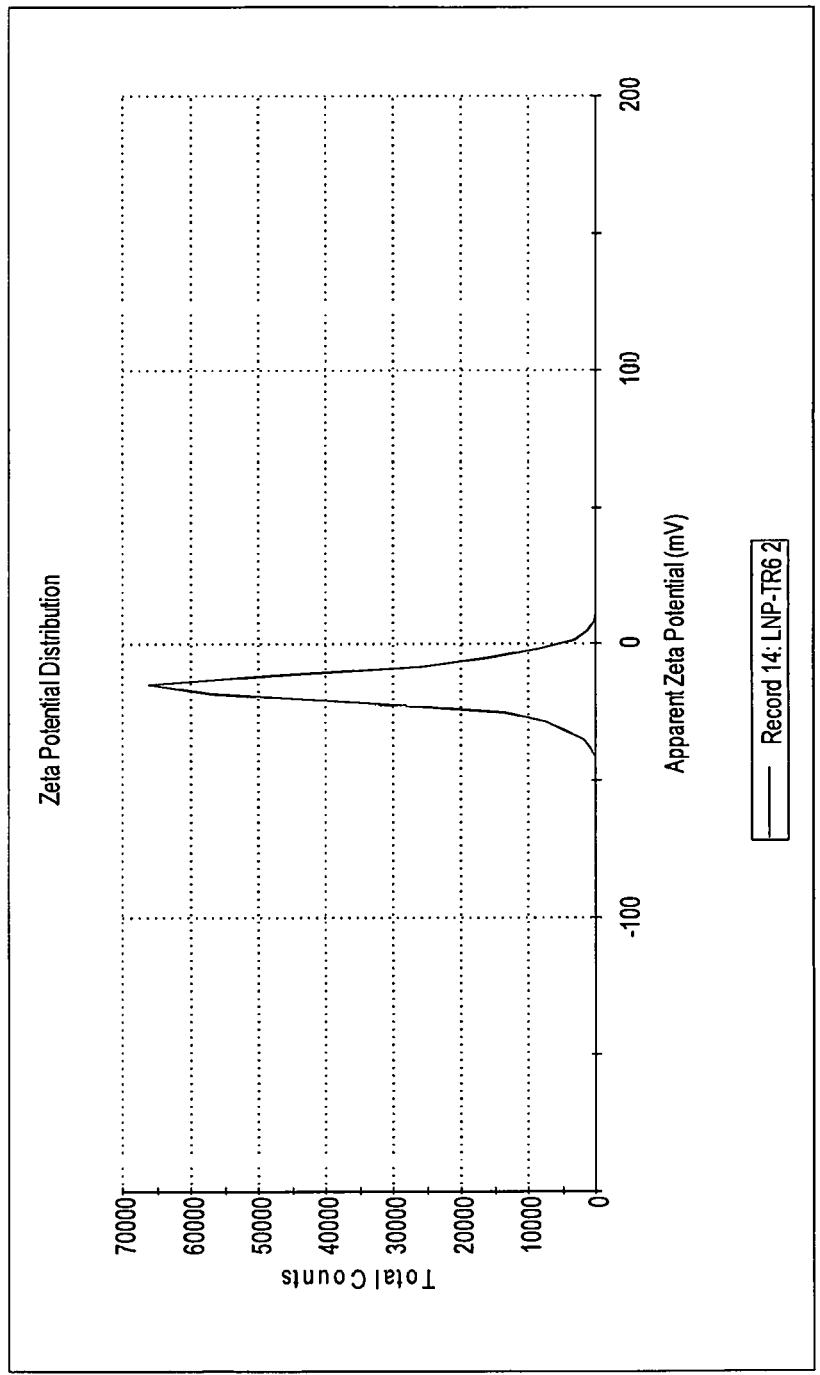
Figure 10. Characterization of LNP-TR6 Liposome (Zeta Potential)

Figure 11. Characterization of LNP-TR5 Liposome
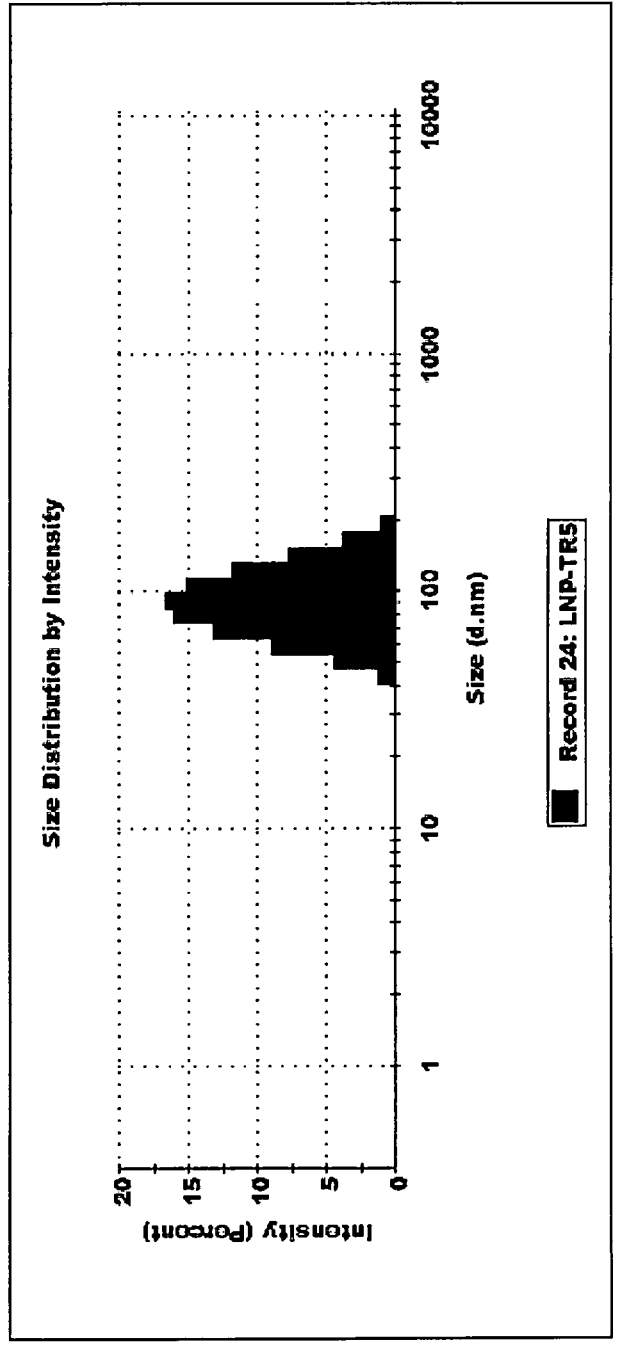

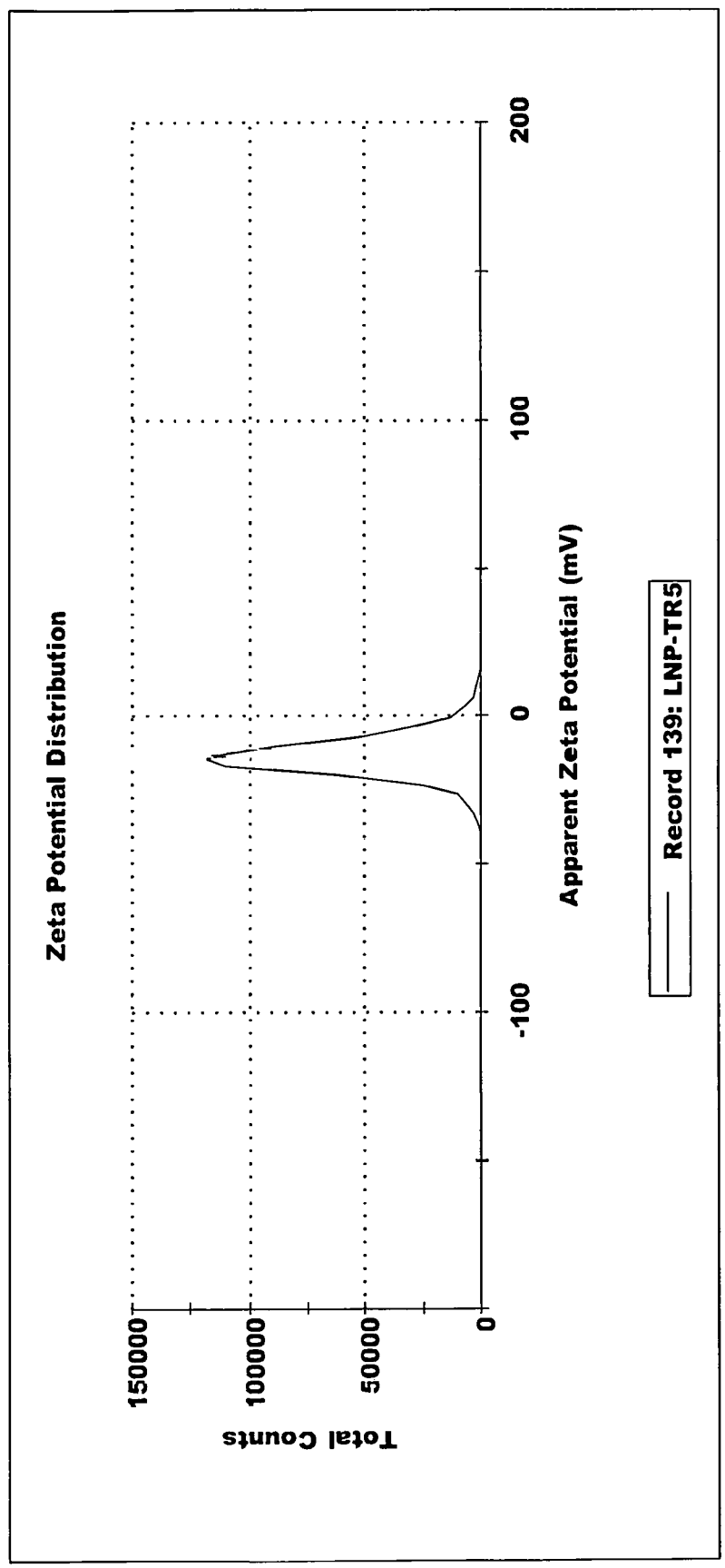
Figure 12. Characterization of LNP-TR5 Liposome (Zeta Potential)

Figure 13. Characterization of LNP-TR3 Liposome
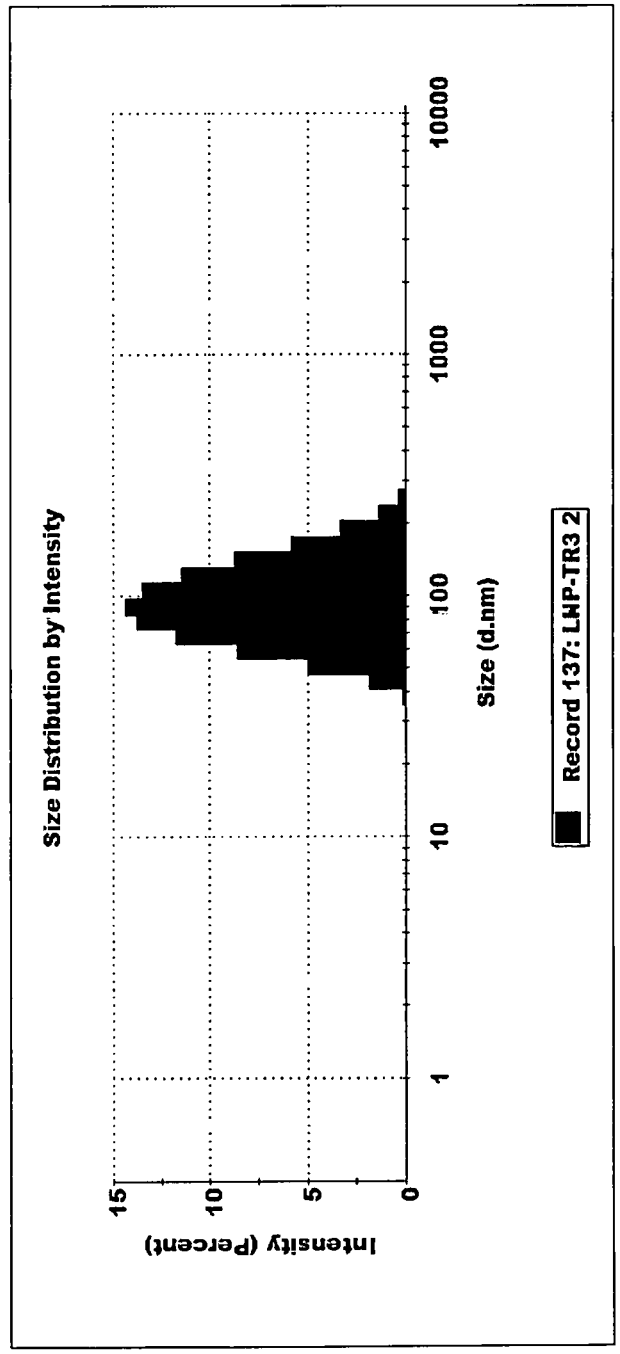

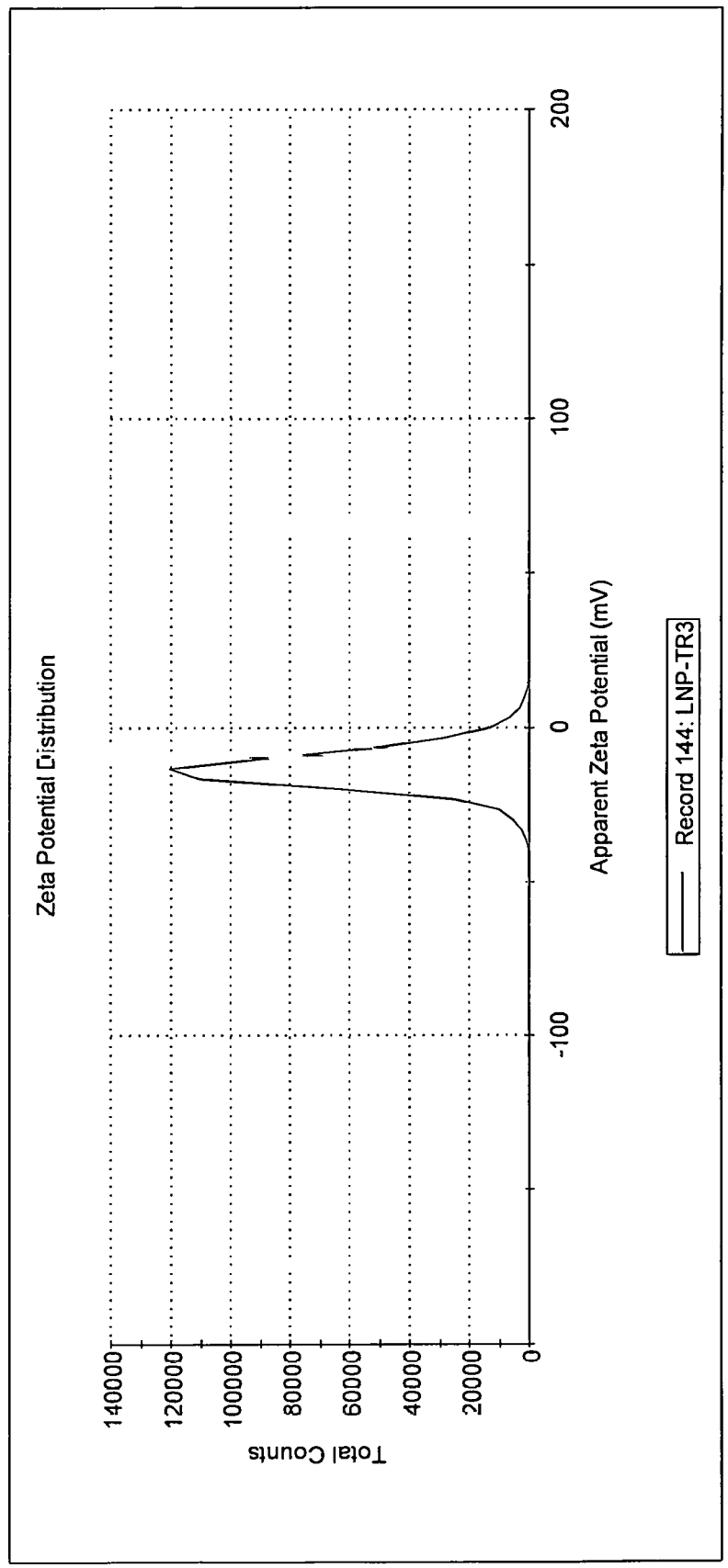
Figure 14. Characterization of LNP-TR3 Liposome (Zeta Potential)

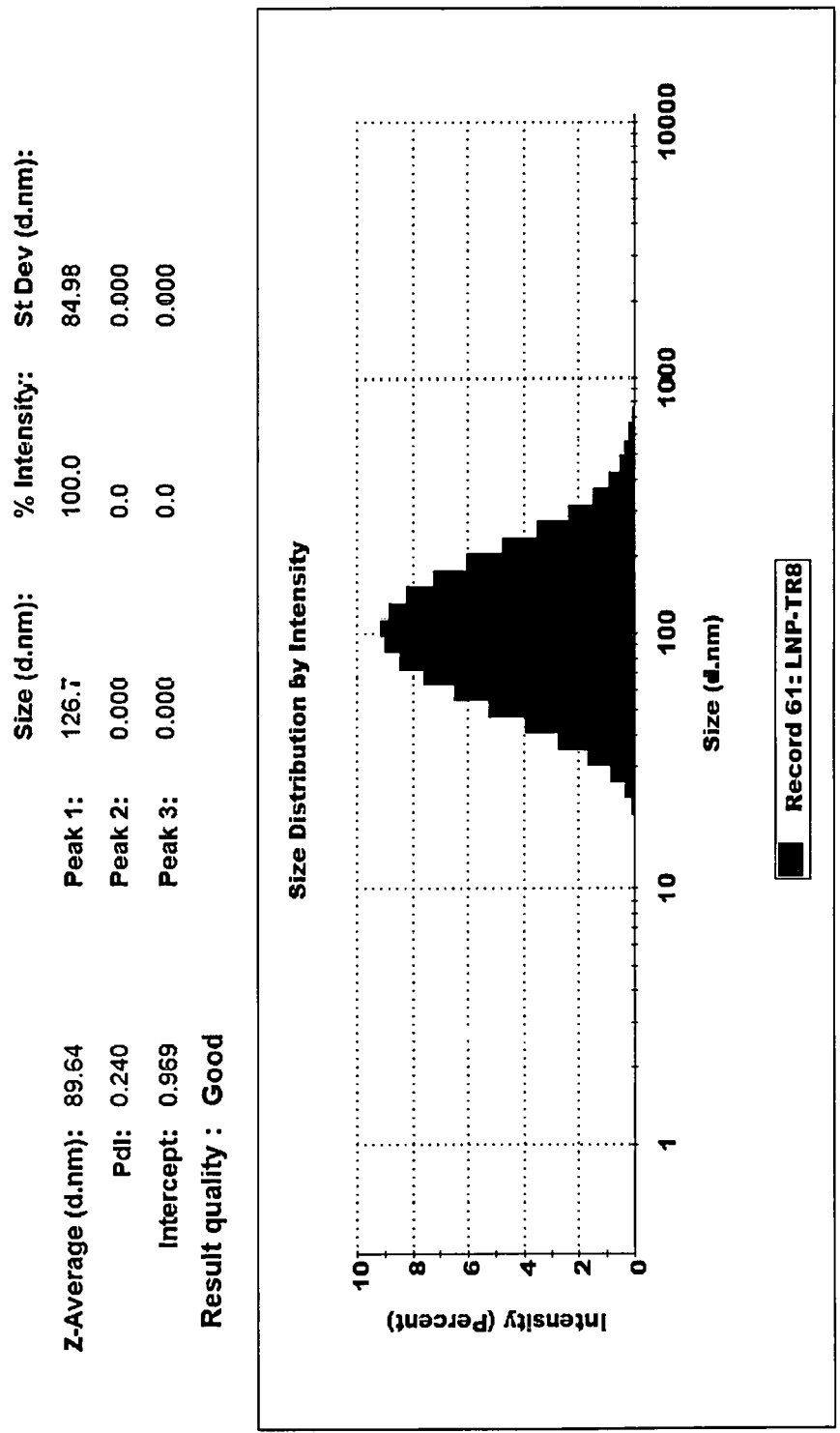
Figure 15. Characterization of LNP-TR8 Liposome

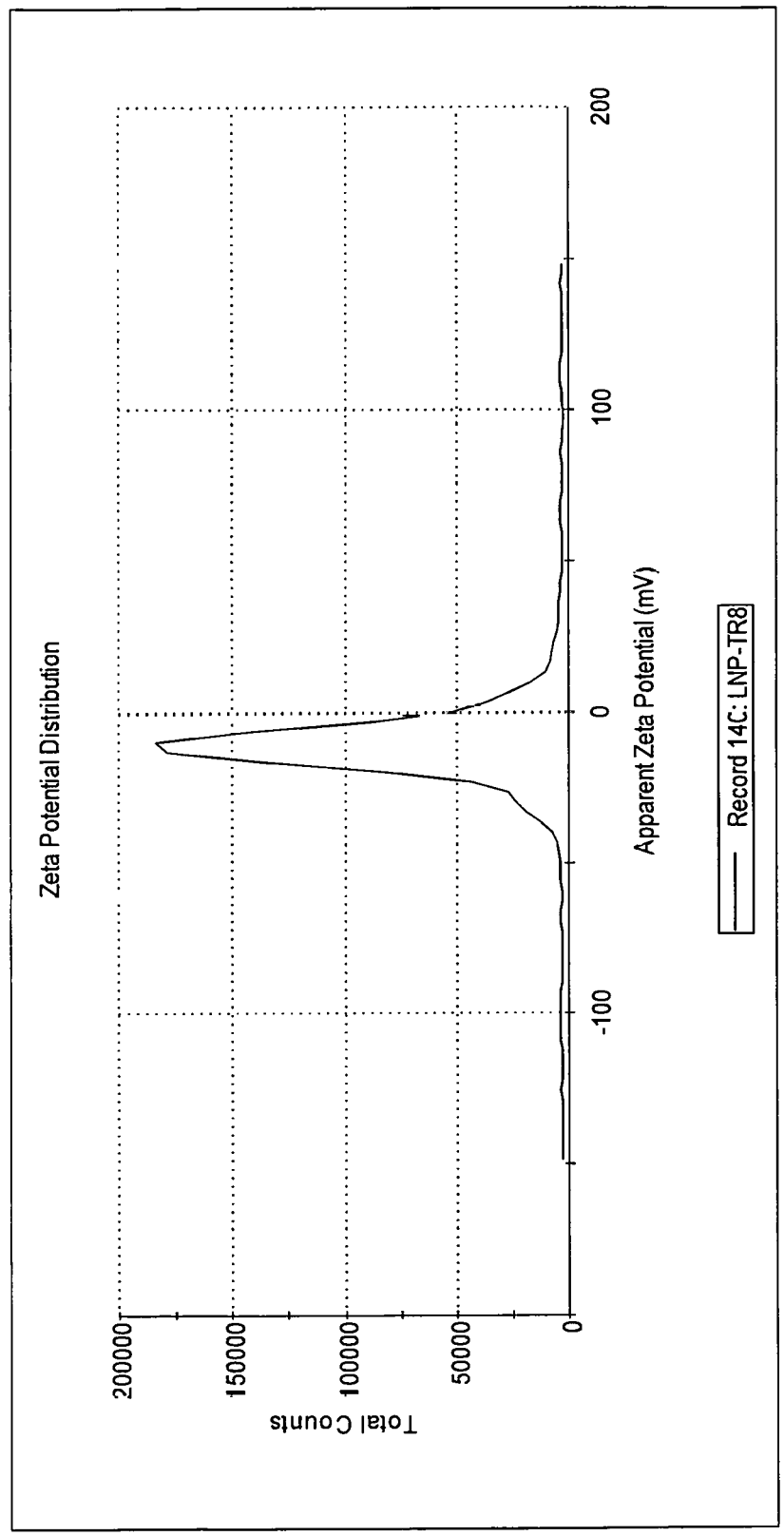
Figure 16. Characterization of LNP-TR8 Liposome (Zeta Potential)

Figure 17. Characterization of LNP-ID3-TR8 Liposome
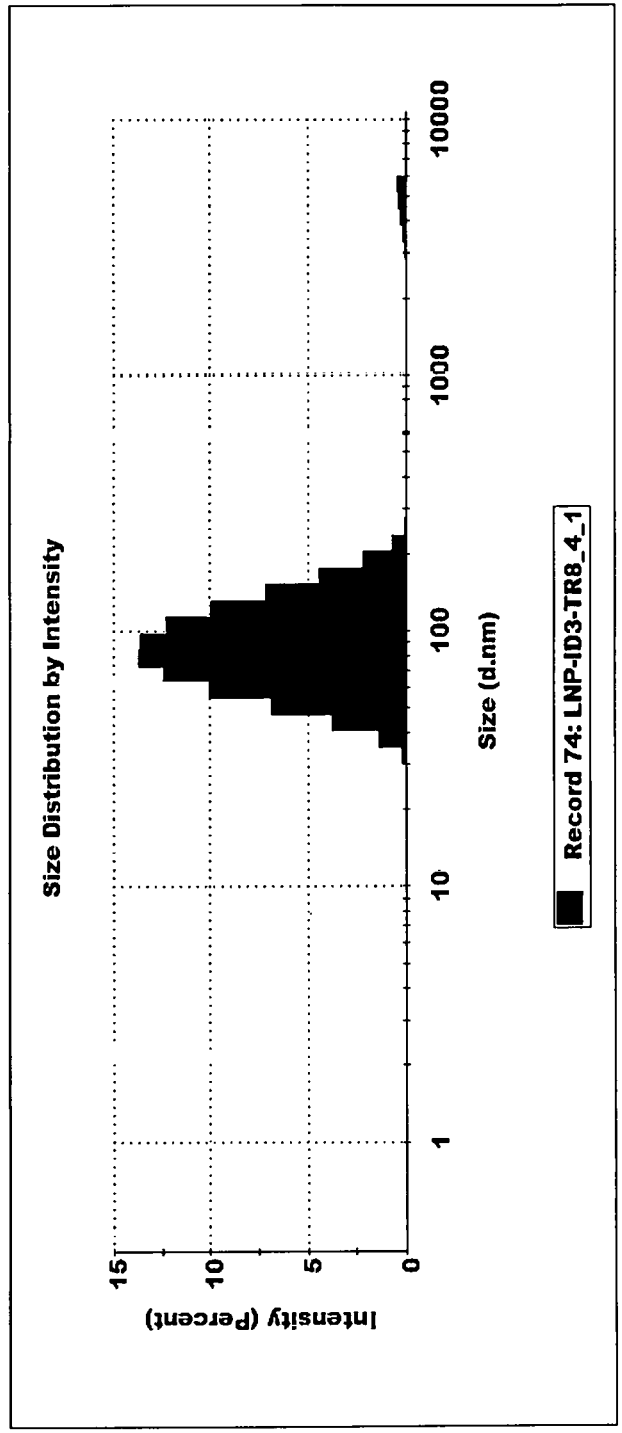

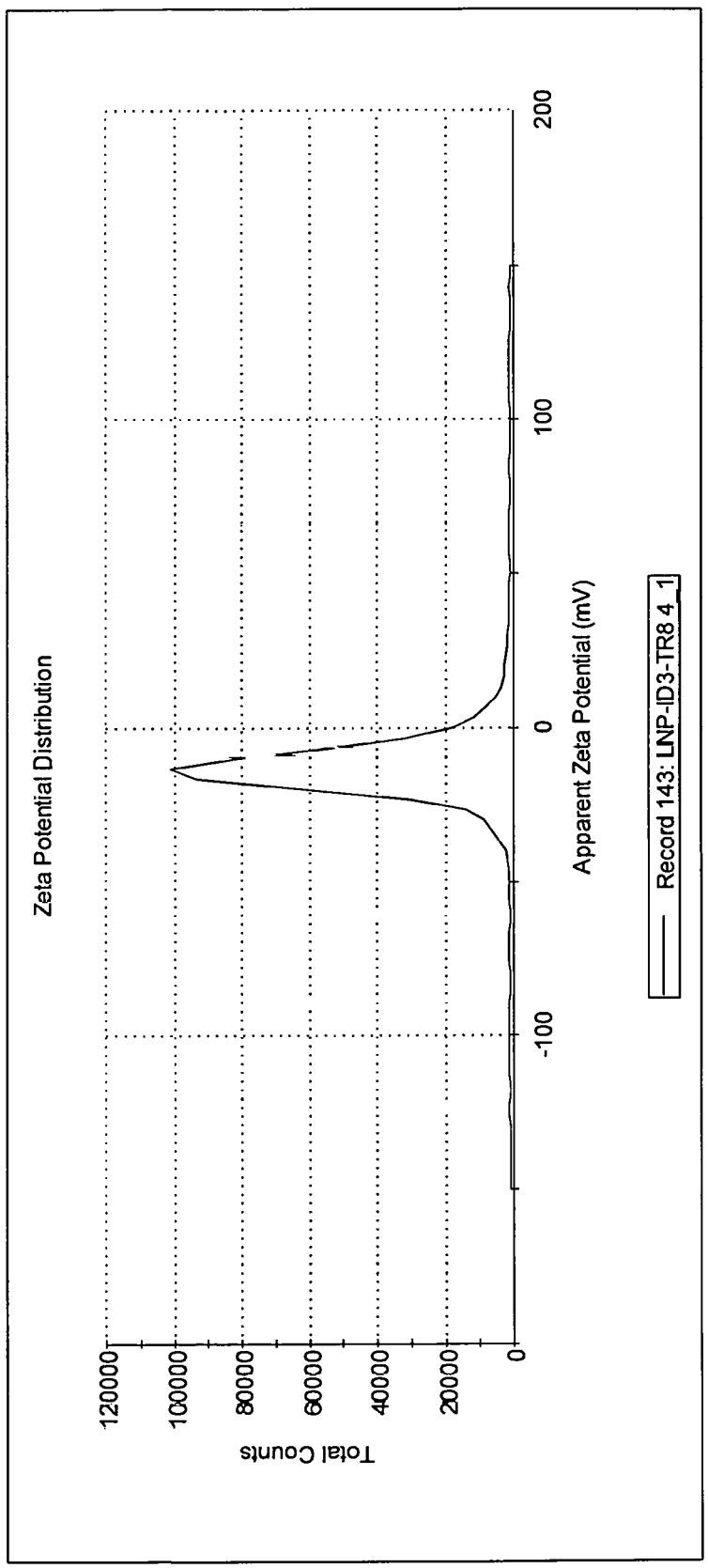
Figure 18. Characterization of LNP-ID3-TR8 Liposome (Zeta Potential)

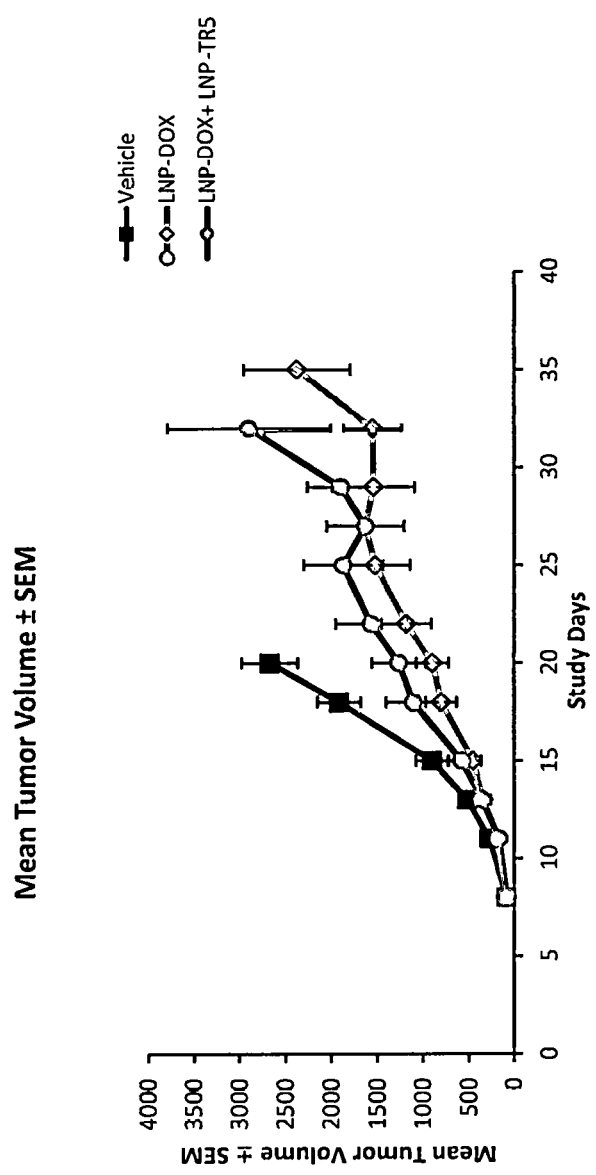
Figure 19. Tumor Inhibition of LNP-TR5 in Combination with LNP-DOX in B16F10 Cancer Cells

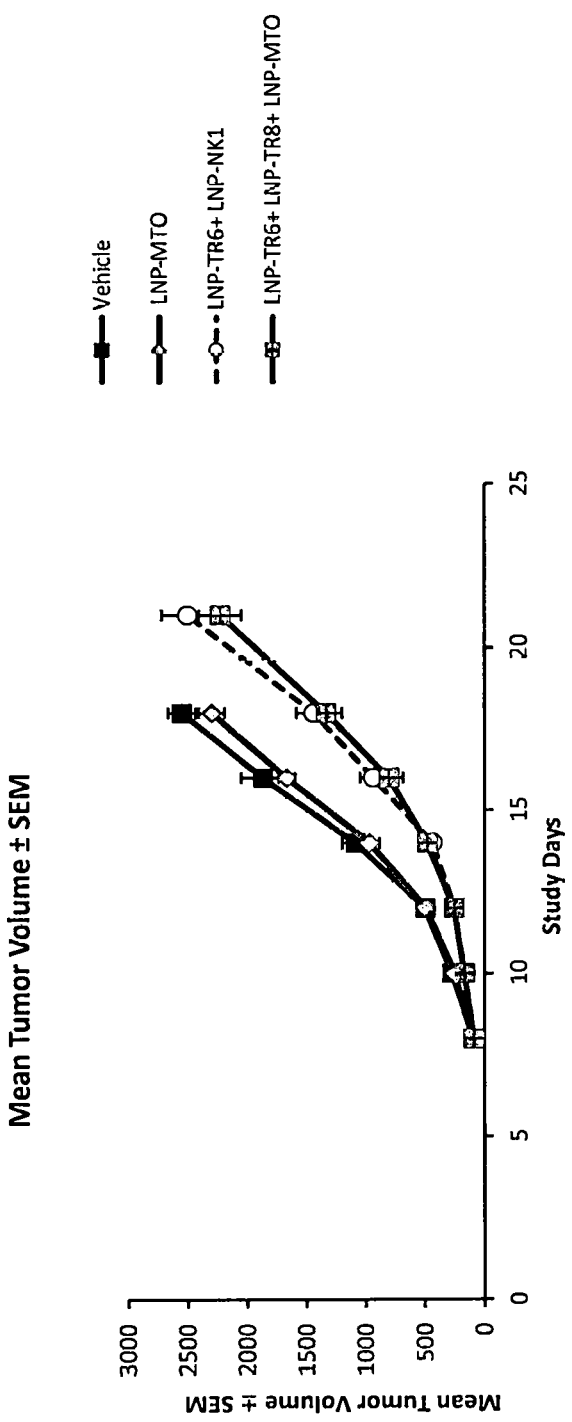
Figure 20. Tumor Inhibition of LNP-TR6 in Combination with LNP-NK1 and LNP-TR6 in Combination with LNP-TR8 and LNP-MTO in B16F10 Cancer Cells

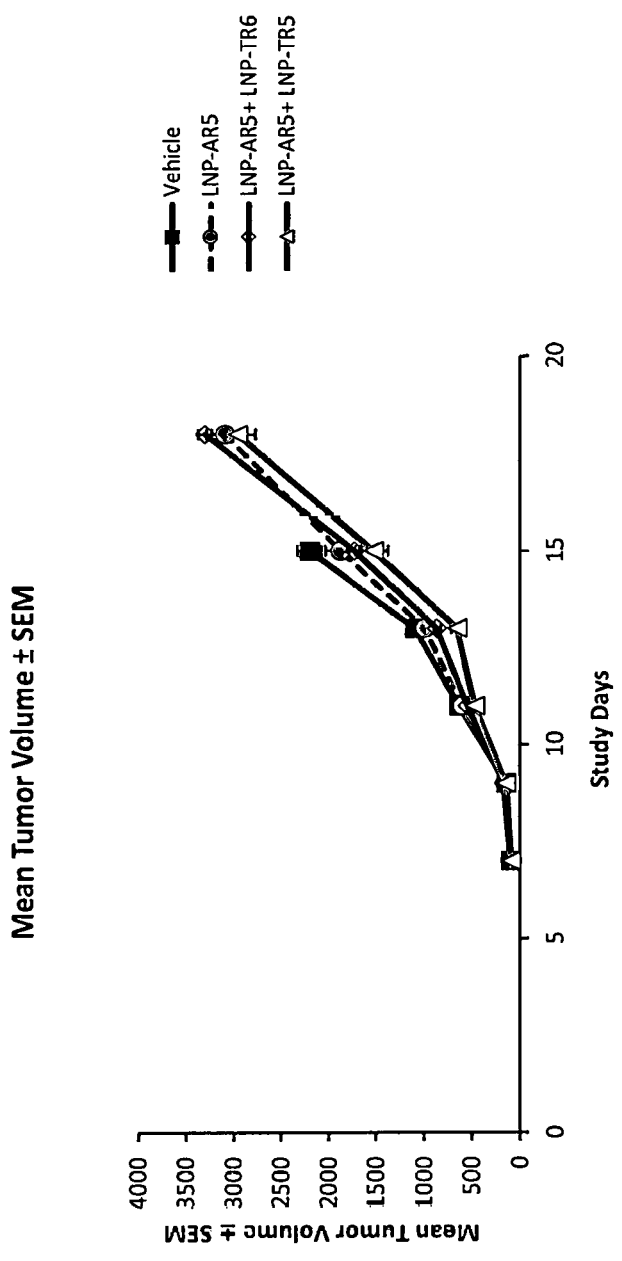
Figure 21. Tumor Inhibition of LNP-TR5 and LNP-TR6 in Combination with LNP-AR5 in B16F10 Cancer Cells

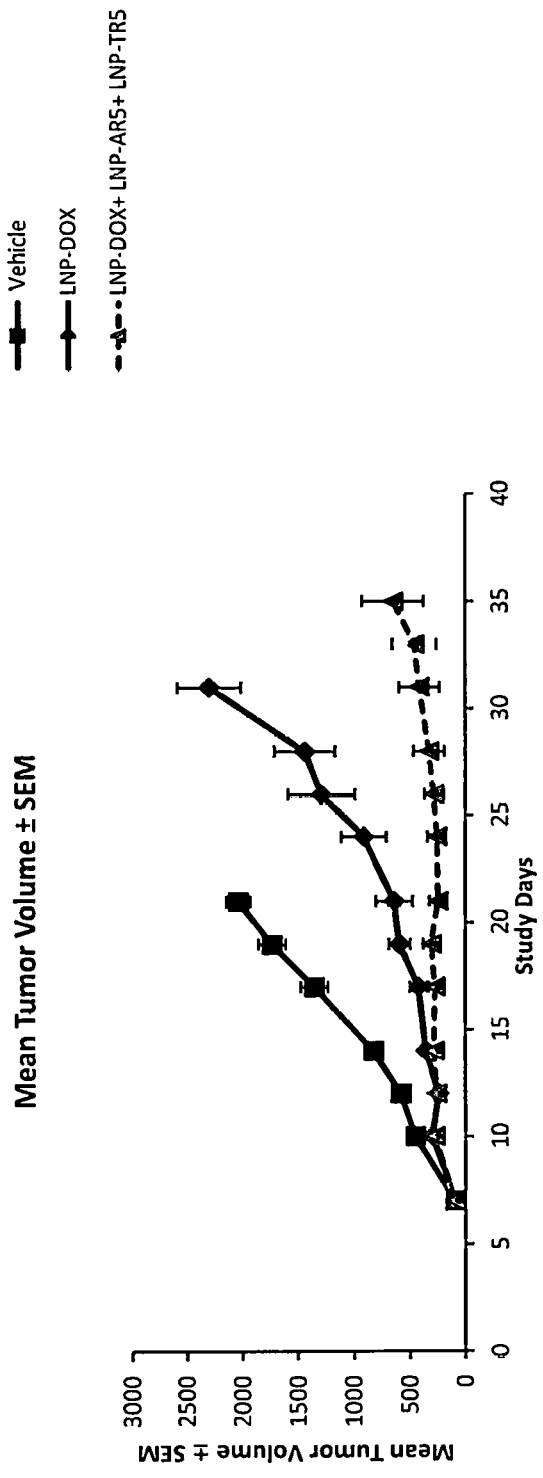
Figure 22. Tumor Inhibition of LNP-TR5 in Combination with LNP-AR5 and LNP-DOX in EMT6 Cancer Cells

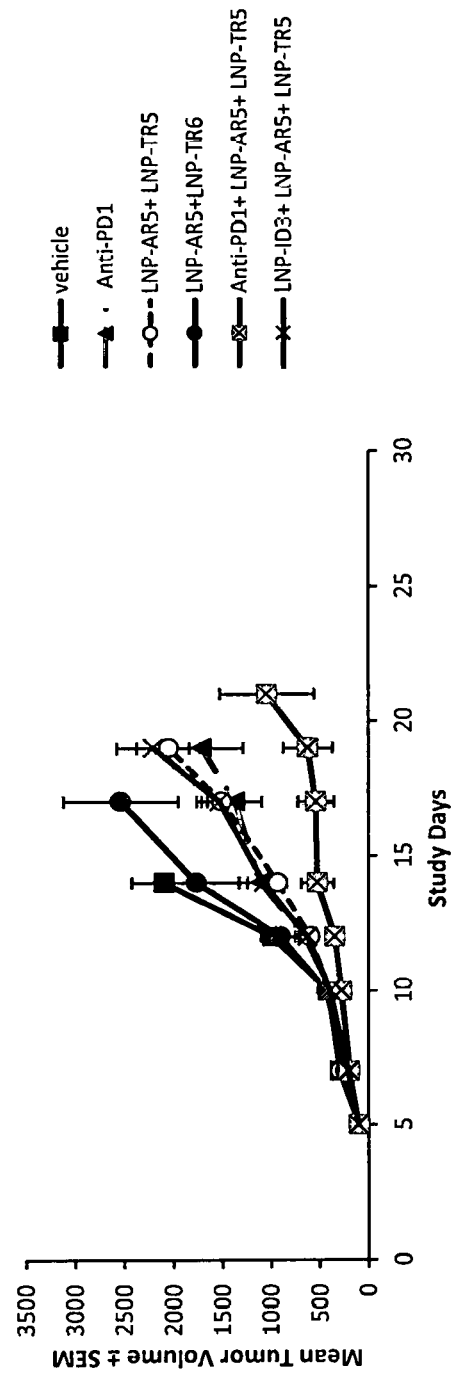
Figure 23. Tumor Inhibition Studies of LNP-TR5 and LNP-TR6 in Multiple Combination(s) in H22 Cancer Cells

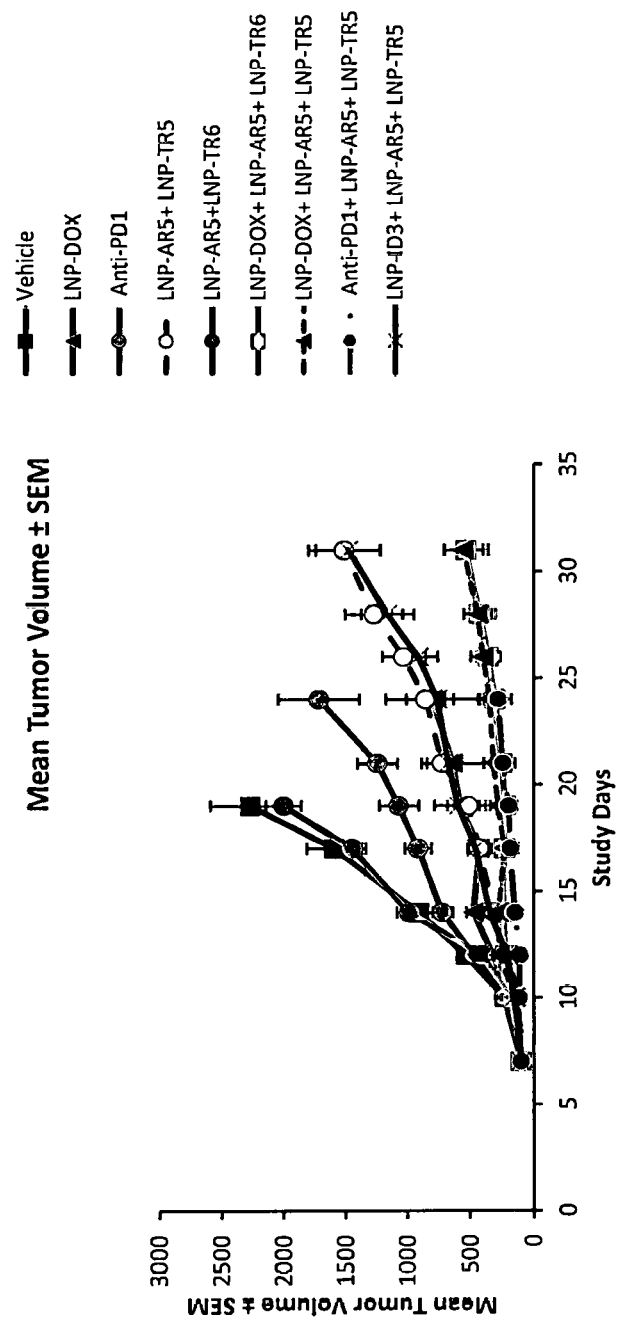
Figure 24. Tumor Inhibition Studies of LNP-TR5 and LNP-TR6 in Multiple Combination(s) in Colorectal Cancer

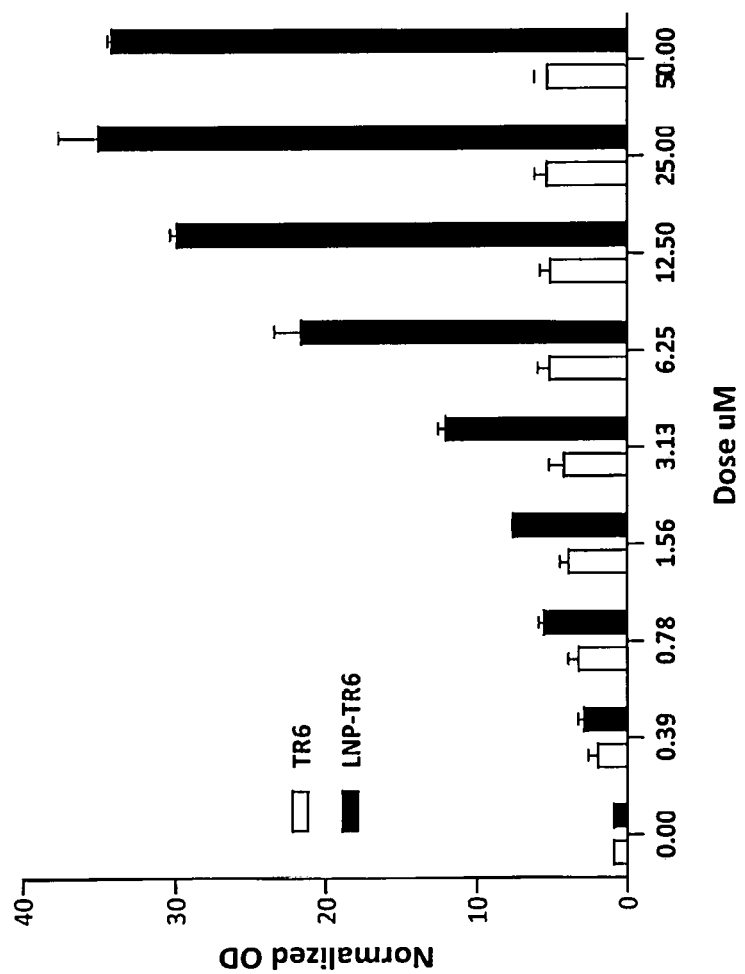
Figure 25. *In Vitro* Validation of TR6 Prodrug in Liposome Form Mechanism of Action

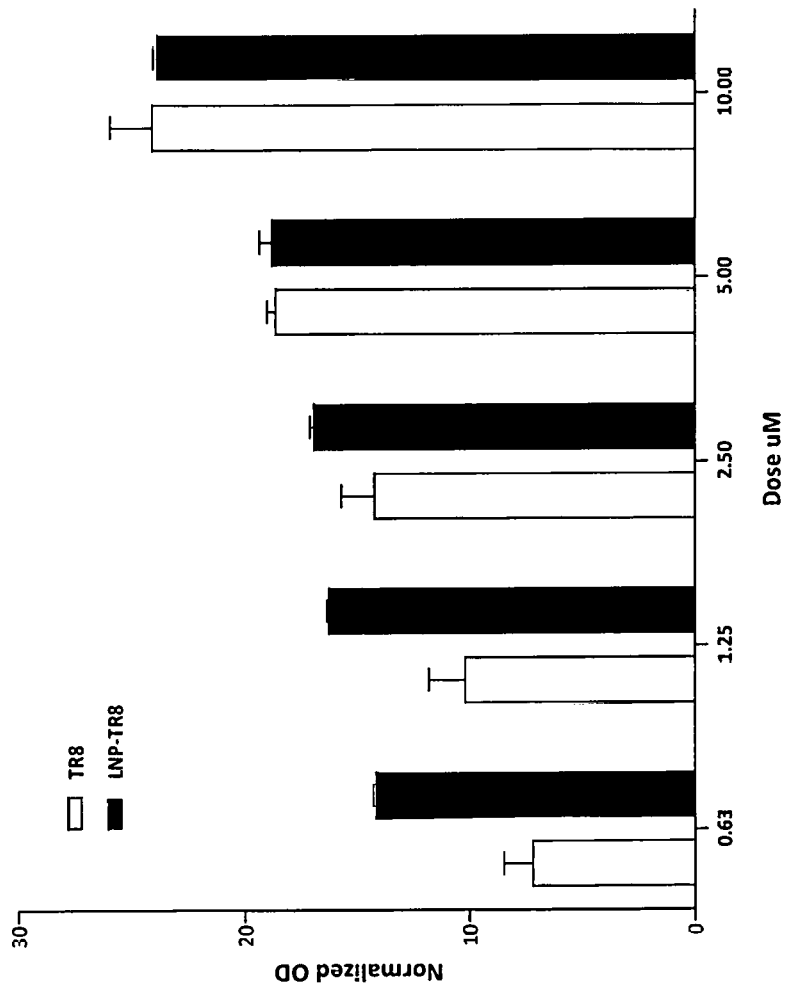
Figure 26. *In Vitro* Validation of TR8 in Liposome Form Mechanism of Action

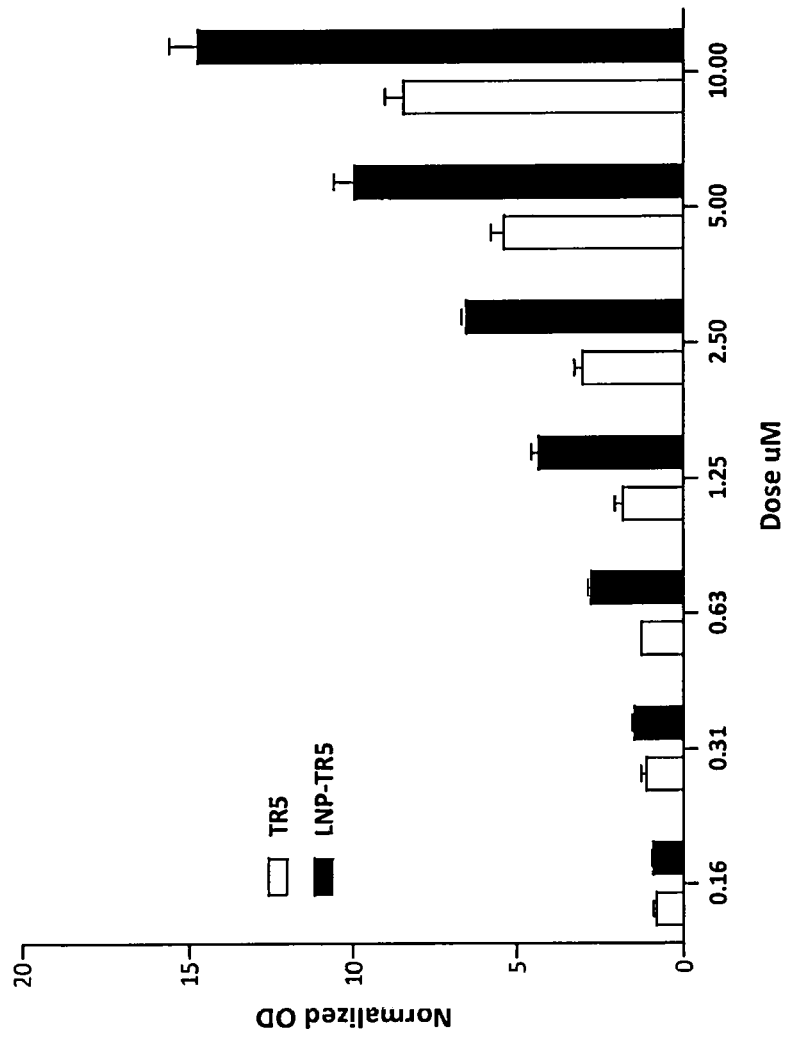
Figure 27. *In Vitro* Validation of TR5 in Liposome Form Mechanism of Action.

Figure 28. *In Vitro* Validation of TR3 in Liposome Form Mechanism of Action.
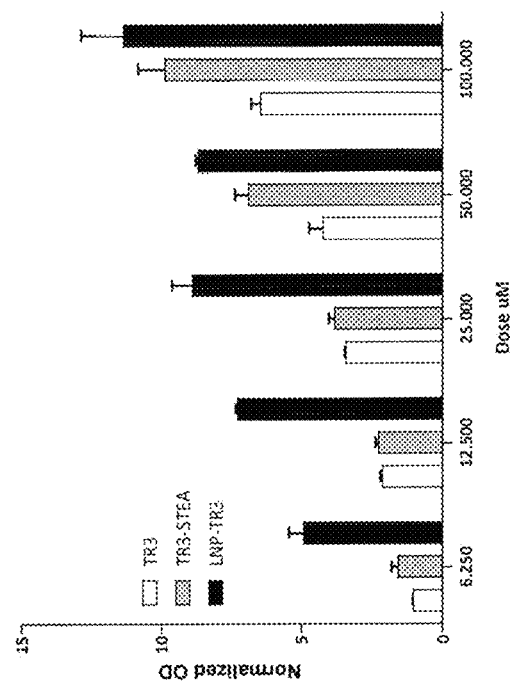
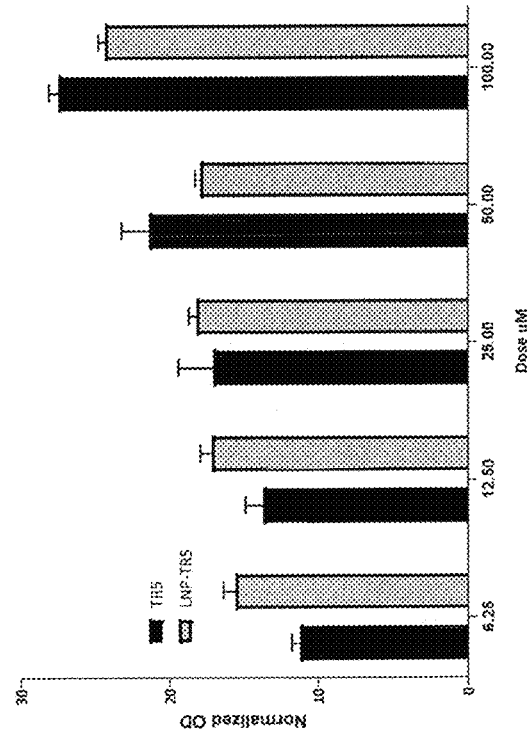

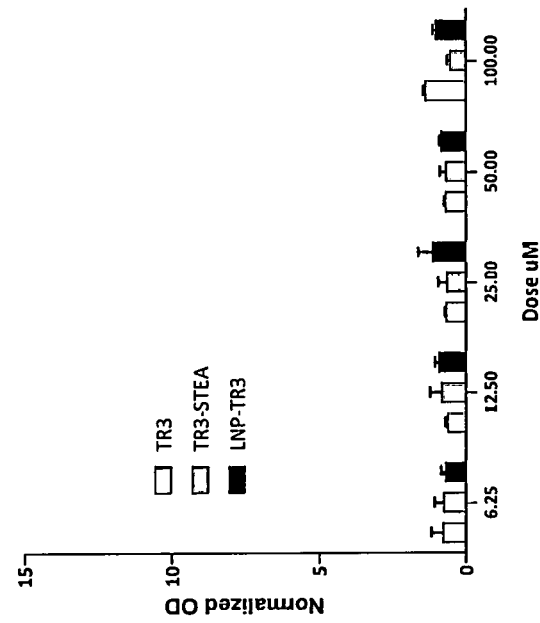
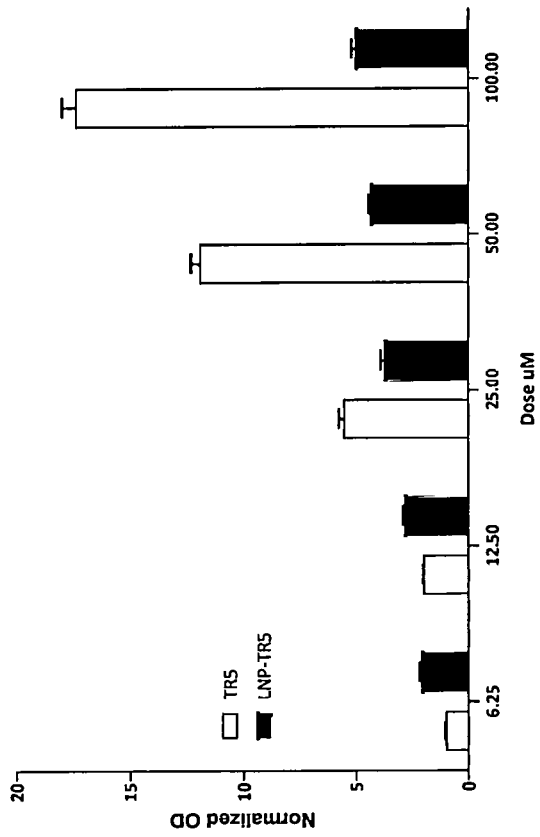
Figure 29. *In Vitro* Validation of TR3 in Liposome Form Mechanism of Action.

FORMULATED AND/OR CO-FORMULATED LIPOSOME COMPOSITIONS CONTAINING TOLL-LIKE RECEPTOR ("TLR") AGONIST PRODRUGS USEFUL IN THE TREATMENT OF CANCER AND METHODS THEREOF

CROSS-REFERENCE TO RELATED APPLICATIONS

This application claims priority to U.S. Provisional Patent Application No. 62/974,746 filed 20 Dec. 2019, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to prodrug compositions that inhibit toll-like receptor(s) ("TLR") after release of the active inhibitor from the prodrug and nanoformulations comprising such prodrugs. Specifically, the invention relates to prodrug compositions which are formulated within a nanocarrier (e.g., a liposome) and used as a vehicle for cancer therapy in humans. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasis to sites distant from the primary tumor and with very few exceptions, metastatic disease tatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

Toll-Like Receptors ("TLRs") are a family of ten (10) identified pattern recognition receptors that respond to pathogen associated molecular patterns (PAMPs) and self-derived damage-associated molecule patterns (DAMPs). The TLRs then activate downstream pathways that initiate an innate immune response by producing inflammatory cytokines, type I interferon (IFN), and other mediators.

The TLR class of proteins are single, membrane-spanning, receptors usually expressed on sentinel cells such as macrophages and dendritic cells that recognize conserved molecules derived from microbes. Once these microbes have breach physical barriers (e.g., skin, or intestinal tract mucosa) they are recognized by TLRs, which then activate immune cell responses.

Upon activation, TLRs recruit adapter proteins (i.e., proteins that mediate other protein-protein interactions) within the cytosol of the immune cell in order to propagate the antigen-induced signal transduction pathway. These recruited proteins are then responsible for the subsequent activation of other downstream proteins, including protein kinases (IKKi, IRAK1, IRAK4, and TBK1) that further amplify the signal and ultimately lead to the upregulation or suppression of genes that orchestrate inflammatory responses and other transcriptional events.

Within the TLR family, several members are worth noting. TLR1 and TLR2 ("TLR 1/2") are cell surface receptors that form heterodimers which recognize bacterial antigens such as lipoproteins as well as DAMPs such as HMGB1, heat shock proteins, and proteoglycans. TLR1/2 are expressed in pre-dendritic cells, macrophage, and NK cells where they mediate the innate response to PAMPS and DAMPS, upregulating inflammatory cytokines and enhancing antigen processing. TLR1/2 agonists, such as PAM3CSK4, can also enhance adaptive immunity as they have been shown to abrogate the immune suppressive effects of Treg cells.

Additionally, TLR4 is a cell surface receptor for various bacterial and viral components, most notably Lipopolysaccharide (LPS). LPS, also known as endotoxin, is a cell wall component of Gram-negative bacteria. LPS has been shown as a natural adjuvant for specific immune responses, especially antigen (Ag)-specific antibody and T cell responses. The toxicity associated with LPS has precluded its use as an effective and safe vaccine adjuvant. However, the monophosphorylated lipid A (MPLA), a metabolic product of LPS, has been found to maintain many of the immunostimulatory functions of LPS, but is significantly less toxic than its parent. Accordingly, MPLA works well as a safe and effective vaccine adjuvant. Lipid A structural features known to account for the maintenance of adjuvant properties and the loss of toxicity include the number of phosphate groups, as well as the number, type, and location of fatty acid residues. Synthetic MPLA, as well as a number of functional analogs, have been produced and characterized as immune stimulating adjuvants. A number of these have been used clinically as adjuvants in vaccine cocktails including in conjunction with tumor antigens to illicit anti-tumor immunity.

In addition, TLR4 is also a receptor for High Mobility Group Box 1 (HMGB1), a protein secreted by tumor cells upon immunogenic cell-death that enhances anti-tumor immunity by recruitment of dendritic cells and stimulation of antigen processing and secretion of inflammatory cytokines by antigen presenting cells (APCs). Accordingly, co-delivery of a TLR4 agonist with an ICD-inducing chemotherapy to a tumor enhances the anti-tumor immunity initiated by the ICD-chemotherapeutic.

Additionally, a prodrug is a medication or compound that, after administration, is metabolized (i.e., converted within the body) into a pharmacologically active drug. Instead of administering a drug directly, a corresponding prodrug is used instead to improve how a medicine is absorbed, distributed, metabolized, and/or excreted. Prodrugs are often designed to improve bioavailability when a drug itself is poorly absorbed from the gastrointestinal tract, for example. A prodrug may be used to improve how selectively the drug interacts with cells or processes that are not its intended target. This reduces adverse or unintended effects of a drug, especially important in treatments like chemotherapy, which can have severe unintended and undesirable side effects. Prodrugs can thus be viewed as drugs containing specialized non-toxic protective groups used in a transient manner to alter or to eliminate undesirable properties in the parent molecule.

Finally, a nanocarrier is a nanomaterial being used as a transport for another substance, such as a drug. There are many different types of nanocarriers. For example, nanocarriers include polymer conjugates, polymeric nanoparticles, lipid-based carriers, and dendrimers to name a few. Different types of nanomaterial(s) being used in nanocarriers allows for hydrophobic and hydrophilic drugs to be delivered throughout the body. Since the human body contains mostly water, the ability to deliver hydrophobic drugs effectively in humans is a major therapeutic benefit of nanocarriers. Nanocarriers show promise in the drug delivery process because they can deliver drugs to site-specific targets, allowing drugs to be delivered in certain organs or cells but not in others. Site-specificity is a major therapeutic benefit since it prevents drugs from being delivered to the wrong places. Additionally, nanocarriers show specific promise for use in chemotherapy because they can help decrease the adverse, broader-scale toxicity of chemotherapy on healthy, fast growing cells around the body. Since chemotherapy drugs can be extremely toxic to human cells, it is important that they are delivered to the tumor without being released into other parts of the body.

From the aforementioned, it will be readily apparent to those skilled in the art that a new treatment paradigm is needed in the treatment of cancers and other immunological diseases. By using novel prodrugs in conjunction with modern nanocarrier modalities, a new disease treatment can be achieved with the overall goal of more effective treatment(s), reduced side effects, and greater therapeutic utility in the treatment of cancers, especially the treatment of cancers in solid tumors.

Given the current deficiencies associated with cancer treatment, it is an object of the present invention to provide new and improved methods of treating cancer(s), immunological disorders, and other diseases utilizing prodrugs encapsulated within a nanocarrier.

In the present disclosure, use of TLR agonists in conjunction with ICD-inducing chemotherapeutics to illicit an immune response directly against the actual patient's tumor cells in situ (i.e., without the need to introduce a tumor antigen or to remove tumor cells for ex vivo treatment). These synergistic functional agents are packaged into a single nano-carrier vehicle ensuring co-delivery and enhanced tumor selectivity of the combination therapy.

SUMMARY OF THE INVENTION

The invention provides for TLR inhibitor prodrug ("TLR Prodrug") compositions comprising a TLR inhibitor agent, a lipid, and a biologically cleavable linker. In certain embodiments, nanocarriers comprising TLR Prodrug(s) are formulated for use as a delivery modality to treat human diseases such as cancer, including solid tumor cancers as well as other immunological disorders. In certain embodiments, the nanocarriers comprise a lipid-bilayer capable of being incorporated into a drug delivery vehicle (i.e., a liposome). In a further preferred embodiment, the liposome comprises cholesterol hemisuccinate ("CHEMS"). In a further preferred embodiment, the liposome of the invention comprises Stearic Acid.

In a further embodiment, the invention comprises methods of delivering a TLR inhibitor to a tumor comprising (i) synthesizing a TLR prodrug; (ii) formulating a TLR prodrug of the invention in a nanocarrier of the invention; and (iii) administering the nanocarrier to a patient.

In another embodiment, the invention comprises methods of delivering a TLR inhibitor with one or more additional immune modulating agent to a tumor comprising (i) synthesizing a TLR prodrug; (ii) co-formulating a TLR prodrug of the invention in a nanocarrier with one or more additional immune modulating agents of the invention; and (iii) administering the nanocarrier to a patient.

In another embodiment, the immune modulating agents comprise agonists of other TLRs, immunogenic-cell death (ICD) inducing chemotherapeutics, PD-1/PD-L1 antagonists, IDO antagonists, STING agonists, CTLA4 inhibitors, iNKT cell agonists, and/or prodrugs thereof.

In another embodiment, the present disclosure teaches methods of synthesizing TLR prodrugs.

In another embodiment, the present disclosure teaches methods of formulating TLR prodrugs within nanocarriers, including but not limited to liposomes.

In another embodiment, the present disclosure teaches methods of treating cancer(s), immunological disorders and other diseases in humans using nanocarriers of the present disclosure.

BRIEF DESCRIPTION OF THE FIGURES

FIG. 1. General Chemical Synthesis for TR5(B).
FIG. 2. General Chemical Synthesis for TR6.
FIG. 3. TLR Inhibitor Prodrug Synthesis Schema with Carboxylic Acid Functionality.
FIG. 4. TLR Inhibitor Prodrug Synthesis Schema with Alcohol Functionality.
FIG. 5. TLR Inhibitor Prodrug Synthesis Schema with Secondary Amine, Amide, or Aniline Functionality.
FIG. 6. Chemical Synthesis for TR6 Prodrug Intermediate.
FIG. 7. Chemical Synthesis for TR6 Prodrug Comprising CHEMS.
FIG. 8. Chemical Synthesis for TR3.
FIG. 9. Characterization of LNP-TR6 Liposome.
FIG. 10. Characterization of LNP-TR6 Liposome (Zeta Potential).
FIG. 11. Characterization of LNP-TR5 Liposome.
FIG. 12. Characterization of LNP-TR5 Liposome (Zeta Potential).
FIG. 13. Characterization of LNP-TR3 Liposome.
FIG. 14. Characterization of LNP-TR3 Liposome (Zeta Potential).
FIG. 15. Characterization of LNP-TR8 Liposome.

FIG. 16. Characterization of LNP-TR8 Liposome (Zeta Potential).

FIG. 17. Characterization of LNP-ID3-TR8 Liposome.

FIG. 18. Characterization of LNP-ID3-TR8 Liposome (Zeta Potential).

FIG. 19. Tumor Inhibition of LNP-TR5 in Combination with LNP-DOX in B16F10 Cancer Cells.

FIG. 20. Tumor Inhibition of LNP-TR6 in Combination with LNP-NK1 and LNP-TR6 in Combination with LNP-TR8 and LNP-MTO in B16F10 Cancer Cells.

FIG. 21. Tumor Inhibition of LNP-TR5 and LNP-TR6 in Combination with LNP-AR5 in B16F10 Cancer Cells.

FIG. 22. Tumor Inhibition of LNP-TR5 in Combination with LNP-AR5 and LNP-DOX in EMT6 Cancer Cells.

FIG. 23. Tumor Inhibition Studies of LNP-TR5 and LNP-TR6 in Multiple Combination(s) in H22 Cancer Cells.

FIG. 24. Tumor Inhibition Studies of LNP-TR5 and LNP-TR6 in Multiple Combination(s) in Colorectal Cancer.

FIG. 25. In Vitro Validation of TR6 Prodrug in Liposome Form Mechanism of Action.

FIG. 26. In Vitro Validation of TR8 in Liposome Form Mechanism of Action.

FIG. 27. In Vitro Validation of TR5 in Liposome Form Mechanism of Action.

FIG. 28. In Vitro Validation of TR3 in Liposome Form Mechanism of Action. 28(A). Raw-Blue™ Incubated with TR5 and LNP-TR5. 28(B). Raw-Blue™ Incubated with TR3, TR3+Stearic Acid, and LNP-TR3.

FIG. 29. In Vitro Validation of TR3 in Liposome Form Mechanism of Action. 29(A). HEK-Blue TLR8 Incubated with TR5 and LNP-TR5. 29(B). HEK-Blue TLR8 Incubated with TR3, TR3+Stearic Acid, and LNP-TR3 Untreated Group.

DETAILED DESCRIPTION OF THE INVENTION

Outline of Sections
I.) Definitions
II.) Prodrugs
III.) Drug Moieties
IV.) Lipids
V.) Linkage Unit(s) ("LU")
VI.) Nanocarriers
VII.) Liposomes
VIII.) Pharmaceutical Formulation
IX.) Combination Therapy
X.) Methods of Delivering Liposomes Comprising Prodrugs to a Cell
XI.) Methods of Treating Cancer(s) and Other Immunological Disorder(s)
XII.) KITS/Articles of Manufacture

I.) Definitions

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub combinations of A, B, C, and D.

Numerical ranges recited herein by endpoints include all numbers and fractions subsumed within that range (e.g., 1 to 5 includes, but is not limited to, 1, 1.5, 2, 2.75, 3, 3.90, 4, and 5).

As used herein, the phrase "consisting essentially of" limits the scope of a claim to the specified materials or steps, plus those that do not materially affect the basic and novel characteristic(s) of the claimed subject matter.

The terms "advanced cancer", "locally advanced cancer", "advanced disease" and "locally advanced disease" mean cancers that have extended through the relevant tissue capsule and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease and these patients have substantially less favorable outcomes compared to patients having clinically localized (organ-confined) cancer.

As used herein the term "alkyl" can refer to $C_1$-$C_{20}$ inclusive, linear (i.e., "straight-chain"), branched, or cyclic, saturated, or at least partially and in some cases unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl, or propyl, is attached to a linear alkyl chain. "Lower alkyl" refers to an alkyl group having 1 to about 8 carbon atoms (i.e., a $C_1$-$C_8$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_1$-$C_8$ straight-chain alkyls. In other embodiments, "alkyl" refers, in particular, to $Ci_{-8}$branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered aromatic and heteroaromatic rings. The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc.) in the backbone of a ring structure. Nitrogen-containing heteroaryl moieties include, but are not limited to, pyridine, imidazole, benzimidazole, pyrazole, pyrazine, triazine, pyrimidine, and the like.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. More traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched, or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyi"), wherein the nitrogen substituent is alkyl as previously described. Exemplary alkylene groups include methylene (—$CH_2$—); ethylene (—$CH_2$—$CH_2$—); propylene (—$(CH_2)3$-); cyclohexylene (—$C_6H_{10}$—); —CH=CH—CH=CH—; —CH=CH—$CH_2$—; —$(CH_2)_q$—N(R)—$(CH_2)_n$—, wherein each of q is an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (-0-$CH_2$-0-); and ethylenedioxyl (-0-$(CH_2)_2$-0-). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

A "bioreactive nanomaterial" refers to an engineered biomaterial that induces or catalyzes a biological response. In certain embodiments the nanomaterial induces a response by virtue of one or more properties selected from the group consisting of composition, size, shape, aspect ratio, dissolution, electronic, redox, surface display, surface coating, hydrophobic, hydrophilic, an atomically thin nanosheet, or functionalized surface groups" to catalyze the biological response at various nano/bio interfaces. In certain embodiments the bioreactive nanomaterial has the ability to inhibit TLR-1 biological responses in cells (e.g., in tumor cells) and/or as well as activating the innate immune system through delivery of "danger signal" and adjuvant effects.

"Bulk" (a.k.a. Drug Substance) means the drug substance or the drug product which has not been filled into final containers for distribution. Final formulated bulk generally refers to drug product which is formulated and being stored or held prior to filling. Drug substance may be stored or held as "bulk" or "concentrated bulk" prior to formulation into drug product.

The terms "carboxylate" and "carboxylic acid" can refer to the groups —C(=O)O$^-$ and —C(=O)OH, respectively. The term "carboxyl" can also refer to the —C(=O)OH group.

The terms "conjugate" and "conjugated" as used herein can refer to the attachment (e.g., the covalent attachment) of two or more components (e.g., chemical compounds, polymers, biomolecule, particles, etc.) to one another. In some embodiments, a conjugate can comprise monovalent moieties derived from two different chemical compounds covalently linked via a bivalent linker moiety (e.g., an optionally substituted alkylene or arylene). In some embodiments, the linker can contain one or more biodegradable bond, such that one or more bonds in the linker can be broken when the prodrug is exposed to a particular physiological environment or enzyme (for example, esterases).

The term "compound" refers to and encompasses the chemical compound (e.g. a prodrug) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

"Drug product" means a final formulation that contains an active drug ingredient (i.e., liposomes containing TLR inhibitor prodrugs) generally, but not necessarily, in association with inactive ingredients. The term also includes a finished dosage form that does not contain an active ingredient but is intended to be used as a placebo.

The term "disulfide" can refer to the —S—S— group.

The term "empty vesicle" means an unloaded lipid vesicle by itself.

The term "ester" as used herein means a chemical compound derived from acid (organic or inorganic) in which at least one —OH hydroxyl group is replaced by an —O-alkyl (alkoxy) or O-Aryl (aryloxy) group.

The term "esterase" as used herein is a hydrolase enzyme that splits esters into an acid and an alcohol.

"Excipient" means an inactive substance used as a carrier for the active ingredients in a drug such as vaccines. Excipients are also sometimes used to bulk up formulations with very potent active ingredients, to allow for convenient and accurate dosage. Examples of excipients include but are not limited to, antiadherents, binders, coatings, disintegrants, fillers, dilutants, flavors, colors, lubricants, and preservatives.

The terms "halo", "halide", or "halogen" as used herein refer to fluoro, chloro, bromo, and iodo groups.

The terms "hydroxyl" and "hydroxy" refer to the —OH group.

The terms "inhibit" or "inhibition of" as used herein means to reduce by a measurable amount, or to prevent entirely.

The terms "individual" or "patient," as used in the context of this disclosure can be used interchangeably.

As used herein, the term "ligand" refers generally to a species, such as a molecule or ion, which interacts, e.g., binds, in some way with another species. See MARTELL, A. E., and HANCOCK, R. P., Metal Complexes in Aqueous Solutions, Plenum: New York (1996), which is incorporated herein by reference in its entirety.

The term "lipid" as used herein refers to a class of naturally occurring (organic) compounds that are insoluble in polar solvents. In the context of the disclosure, a lipid refers to conventional lipids, phospholipids, cholesterol, chemically functionalized lipids for attachment of PEG and ligands, etc.

The term "lipid bilayer" or "LB" refers to any double layer of oriented amphipathic lipid molecules in which the hydrocarbon tails face inward to form a continuous non-polar phase.

The term(s) "liposome" or "lipid vesicle" or "vesicle" are used interchangeably to refer to an aqueous compartment enclosed by a lipid bilayer, as being conventionally defined (see, STRYER (1981) Biochemistry, 2d Edition, W. H. Freeman & Co., p. 213).

The term "mammal" refers to any organism classified as a mammal, including mice, rats, rabbits, dogs, cats, cows, horses, and humans. In one embodiment of the invention, the mammal is a mouse. In another embodiment of the invention, the mammal is a human.

The terms "mercapto" or "thiol" refer to the —SH group.

The terms "metastatic cancer" and "metastatic disease" mean cancers that have spread to regional lymph nodes or to distant sites and are meant to include stage D disease under the AUA system and stage T×N×M+ under the TNM system.

The terms "nanocarrier", "nanoparticle, and "nanoparticle drug carrier" are used interchangeably and refer to a nanostructure having an aqueous, solid, or polymeric interior core. In certain embodiments the nanocarrier comprises a lipid bilayer encasing (or surrounding or enveloping) the porous particle core. In certain embodiments the nanocarrier is a liposome, lipid nanoparticle ("LNP") or a solid-lipid nanoparticle ("SLNP").

The terms "nanoscale particle," "nanomaterial," "nanocarrier", and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

The term "nanovesicle" refers to a "lipid vesicle" having a diameter (or population of vesicles having a mean diameter) ranging from about 20 nm, or from about 30 nm, or from about 40 nm, or from about 50 nm up to about 500 nm, or up to about 400 nm, or up to about 300 nm, or up to about 200 nm, or tip to about it 150 nm, or up to about 100 nm, or up to about 80 nm. In certain embodiments a nanovesicle has a diameter ranging from about 40 nm up to about 80 nm, or from about 50 nm up to about 70 nm.

"Pharmaceutically acceptable" refers to a non-toxic, inert, and/or composition that is physiologically compatible with humans or other mammals.

"Pharmaceutical formulation" means the process in which different chemical substances are combined to a pure drug substance to produce a final drug product.

The term "phosphonate" refers to the —P(=O)(OR)$_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the —OP(=O)(OR')$_2$ group, where R' is H or a negative charge.

The term "prodrug" means a medication or compound that, after administration, is metabolized into a pharmacologically active drug. For the purposes of this disclosure, a prodrug of the invention comprises three (3) components: (i) a drug moiety; (ii) a lipid moiety; and (iii) a linkage unit ("LU").

The term "TLR prodrug" means a prodrug of the inventions wherein the drug moiety comprises a TLR inhibitor.

The term "pyrolipid" refers to a conjugate of a lipid and a porphyrin, porphyrin derivative, or porphyrin analog. In some embodiments, the pyrolipid can comprise a lipid conjugate wherein a porphyrin or a derivative or analog thereof is covalently attached to a lipid side chain. See, for example U.S. Patent Application Publication No. 2014/0127763.

As used herein, the terms "specific", "specifically binds" and "binds specifically" refer to the selective binding of nanocarrier of the invention to the target TLR-1.

The term "supported lipid bilayer" means a lipid bilayer enclosing a porous particle core. This definition as set forth in the disclosure is denoted because the lipid bilayer is located on the surface and supported by a porous particle core. In certain embodiments, the lipid bilayer can have a thickness ranging from about 6 nm to about 7 nm which includes a 3-4 nm thickness of the hydrophobic core, plus the hydrated hydrophilic head group layers (each about 0.9 nm) plus two partially hydrated regions of about 0.3 nm each. In various embodiments, the lipid bilayer surrounding the liposome comprises a continuous bilayer or substantially continuous bilayer that effectively envelops and seals the TLR Inhibitor.

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively, As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "therapeutically effective amount" refers to the amount of active prodrug, nano-encapsulated prodrug, or pharmaceutical agent that elicits the biological or medicinal response in a tissue, system, animal, individual or human.

The term "unsupported lipid bilayer" means an uncoated lipid bilayer in a lipid vesicle or liposome.

II.) Prodrugs

As shown in the present disclosure and for the purposes of this invention, a suitable prodrug is formed by conjugating a drug moiety of the invention (See, section entitled Drug Moieties) to a lipid moiety of the invention (See, section entitled Lipids) via an LU (See, section entitled Linkage Units) of the present disclosure. For the purposes of this disclosure, formation of a TLR prodrug can utilize several strategies. (See, for example, FIG. 3, FIG. 4, and FIG. 5).

Accordingly, in some embodiments, the prodrug is a drug-lipid moiety comprising a TLR inhibitor of the disclosure.

In a further embodiment, the prodrug is a drug-lipid moiety comprising a TLR inhibitor of the disclosure, wherein the TLR inhibitor inhibits TLR1/2.

In a further embodiment, the prodrug is a drug-lipid moiety comprising a TLR inhibitor of the disclosure, wherein the TLR inhibitor inhibits TLR4.

In a further embodiment, the prodrug is a drug-lipid moiety comprising a TLR inhibitor of the disclosure, wherein the TLR inhibitor inhibits TLR8.

In a further embodiment, the prodrug is a drug-lipid moiety comprising a TLR inhibitor of the disclosure, wherein the TLR inhibitor inhibits TLR7/8.

In a further embodiment, the prodrug is a drug-lipid moiety comprising a TLR inhibitor of the disclosure, wherein the TLR inhibitor inhibits TLR1/2, and wherein the prodrug comprises a prodrug from Formula I.

In a further embodiment, the prodrug is a drug-lipid moiety comprising a TLR inhibitor of the disclosure, wherein the TLR inhibitor inhibits TLR7.

In a further embodiment, the prodrug is a drug-lipid moiety comprising a TLR inhibitor of the disclosure, wherein the TLR inhibitor inhibits TLR7, and wherein the prodrug comprises a prodrug from Formula II.

In one embodiment, the prodrug comprises the following chemical structure denoted Formula I:

FORMULA I

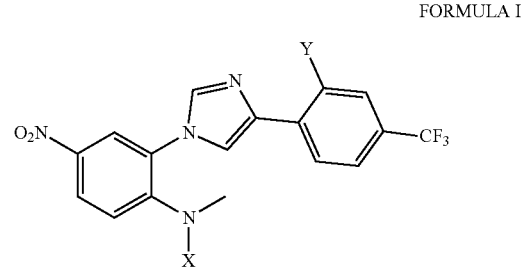

Wherein, in exemplary embodiments of FORMULA I:
X=

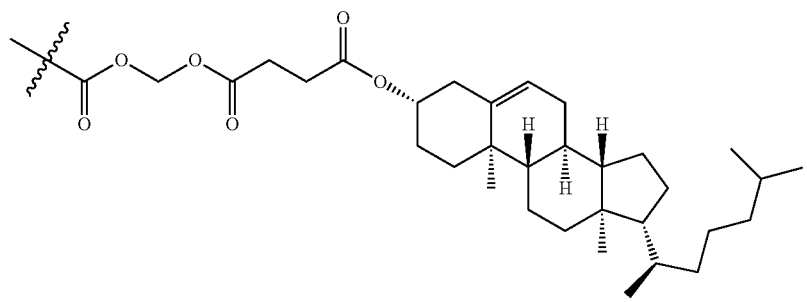

-continued

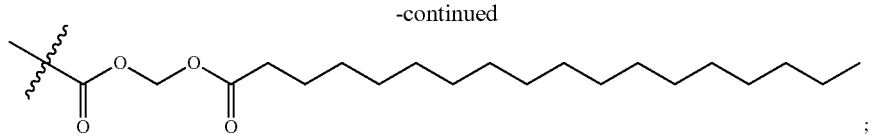

and
Y=H, OH;
Or
X=H; and
Y=CHEMS or Stearic Acid or CHEMS+Linker or Stearic Acid+Linker In a further embodiment, the prodrug comprises the following chemical structure denoted Formula II:

FORMULA II

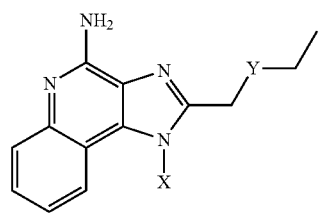

Wherein, in exemplary embodiments of FORMULA II:
X=

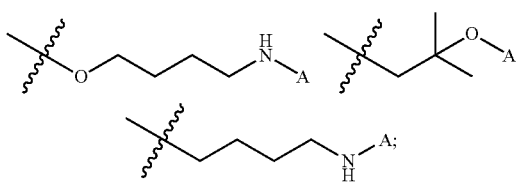

Y=CH$_2$, O, NH; and

A =

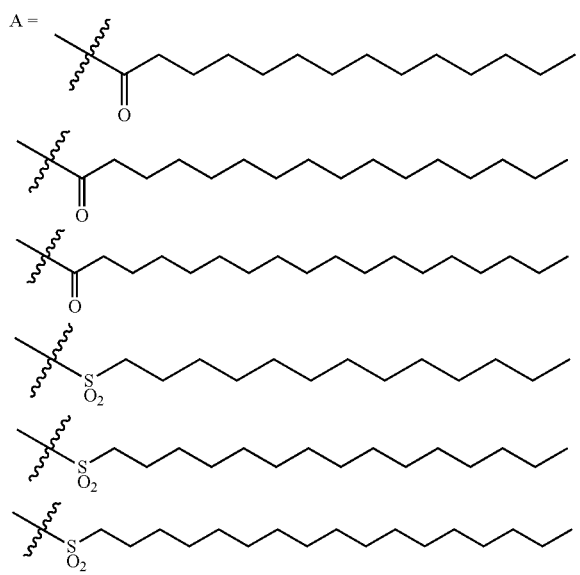

-continued

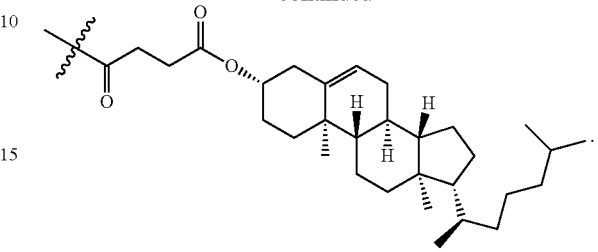

Thus, in one embodiment, the prodrug is a drug-lipid moiety comprising a TLR inhibitor of FORMULA I.

Thus, in one embodiment, the prodrug is a drug-lipid moiety comprising a TLR inhibitor of FORMULA II.

In one embodiment, the prodrug is a drug-lipid moiety comprising a TLR inhibitor set forth in FIG. 1.

In one embodiment, the prodrug is a drug-lipid moiety comprising a TLR inhibitor set forth in FIG. 2.

In one embodiment, the prodrug is a drug-lipid moiety comprising a TLR inhibitor set forth in FIG. 7.

In one embodiment, the prodrug is a drug-lipid moiety comprising a TLR inhibitor set forth in FIG. 8.

In a further embodiment, the TLR prodrug is a drug-lipid moiety comprising a lipid of the disclosure.

In a further embodiment, the TLR prodrug is a drug-lipid moiety whereby the lipid is CHEMS.

In a further embodiment, the TLR prodrug is a drug-lipid moiety whereby the lipid is Stearic Acid.

In a further embodiment, the TLR prodrug is a drug-lipid moiety comprising a LU of the disclosure.

In a further embodiment, the TLR prodrug is a drug-lipid moiety whereby the LU is a hydromethylcarbamate linker.

In a further embodiment, the prodrug is a drug-lipid moiety comprising a TLR inhibitor of the invention, wherein the TLR inhibitor comprises the chemical composition(s) TR6 and/or TR6(A).

In a further embodiment, the prodrug is a drug-lipid moiety comprising a TLR inhibitor of the invention, wherein the TLR inhibitor comprises TR6 and/or TR6(A) and further comprises CHEMS.

In a further embodiment, the prodrug is a drug-lipid moiety comprising a TLR inhibitor of the invention, wherein the TLR inhibitor comprises TR6 and/or TR6(A) and further comprises Stearic Acid.

In a further embodiment, the prodrug is a drug-lipid moiety comprising a TLR inhibitor of the invention, wherein the TLR inhibitor comprises the chemical composition(s) TR3, TR5, TR5(A) and/or TR5(B).

In a further embodiment, the prodrug is a drug-lipid moiety comprising a TLR inhibitor of the invention, wherein the TLR inhibitor comprises TR3, TR5, TR5(A) and/or TR5(B) and further comprises CHEMS.

In a further embodiment, the prodrug is a drug-lipid moiety comprising a TLR inhibitor of the invention, wherein the TLR inhibitor comprises TR3, TR5, TR5(A) and/or TR5(B) and further comprises Stearic Acid.

In a further embodiment, the prodrug is a drug-lipid moiety comprising a TLR inhibitor of the invention, wherein the TLR inhibitor comprises TR6 and further comprises CHEMS and whereby the LU is a hydromethylcarbamate linker.

In a further embodiment, the prodrug is a drug-lipid moiety comprising a TLR inhibitor of the invention, wherein the TLR inhibitor comprises TR6 and further comprises Stearic Acid and whereby the LU is a hydromethylcarbamate linker.

In a further embodiment, the prodrug is a drug-lipid moiety comprising a TLR inhibitor of the inventions, wherein the TLR inhibitor comprises TR6 and further comprises Stearic Acid having the following structure:

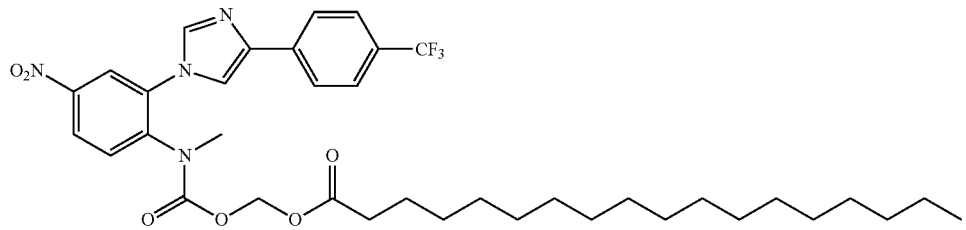 [SMILES: CCCCCCCCCCCCCCCCCC(=O)OCOC(=O)N(C)c1ccc([N+](=O)[O-])cc1-n1cnc(-c2ccc(C(F)(F)F)cc2)c1]

In a further embodiment, the prodrug is a drug-lipid moiety comprising a TLR inhibitor, wherein the TLR inhibitor inhibits TLR1/2, of the invention(s), and wherein the TLR inhibitor comprises TR6 and further comprises Stearic Acid having the following structure.

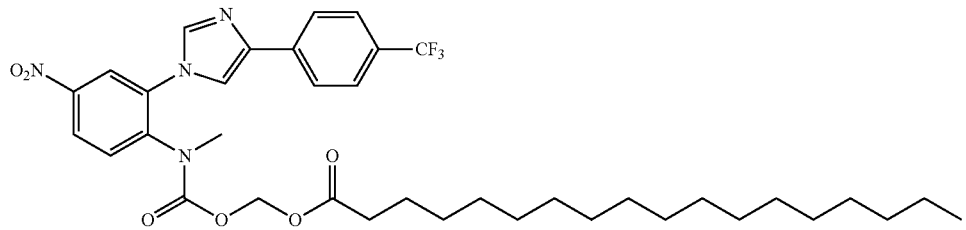 [SMILES: CCCCCCCCCCCCCCCCCC(=O)OCOC(=O)N(C)c1ccc([N+](=O)[O-])cc1-n1cnc(-c2ccc(C(F)(F)F)cc2)c1]

In a further embodiment, the prodrug is a drug-lipid moiety comprising a TLR inhibitor of the invention, wherein the TLR inhibitor comprises TR5, TR5(A) and/or TR5(B) and further comprises CHEMS and whereby the LU is a hydromethylcarbamate linker.

In a further embodiment, the prodrug is a drug-lipid moiety comprising a TLR inhibitor of the invention, wherein the TLR inhibitor comprises TR5, TR5(A) and/or TR5(B) and further comprises Stearic Acid and whereby the LU is a hydromethylcarbamate linker.

In a further embodiment, the prodrug is a drug-lipid moiety comprising a TLR inhibitor of the inventions, wherein the TLR inhibitor comprises TR5(B) and further comprises Stearic Acid having the following structure:

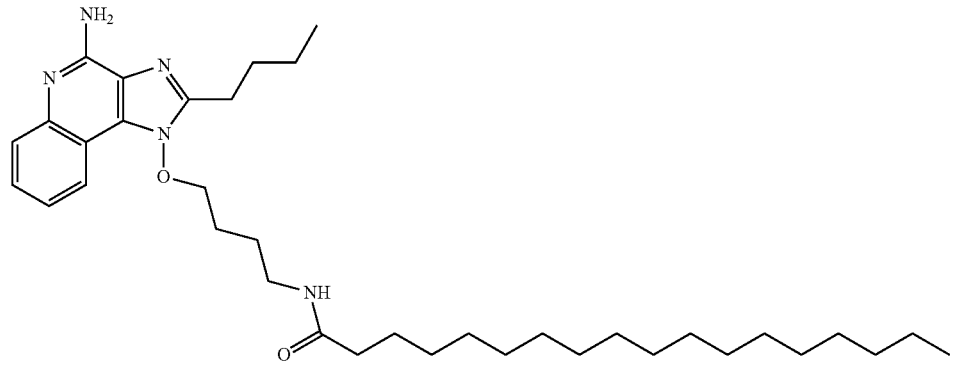 [SMILES: CCCCCCCCCCCCCCCCCC(=O)NCCCCOn1c(CCCC)nc2c(N)nc3ccccc3c21]

In a further embodiment, the prodrug is a drug-lipid moiety comprising a TLR inhibitor, wherein the TLR inhibitor inhibits TLR7, of the invention(s), and wherein the TLR inhibitor comprises TR5(B) and further comprises Stearic Acid having the following structure:

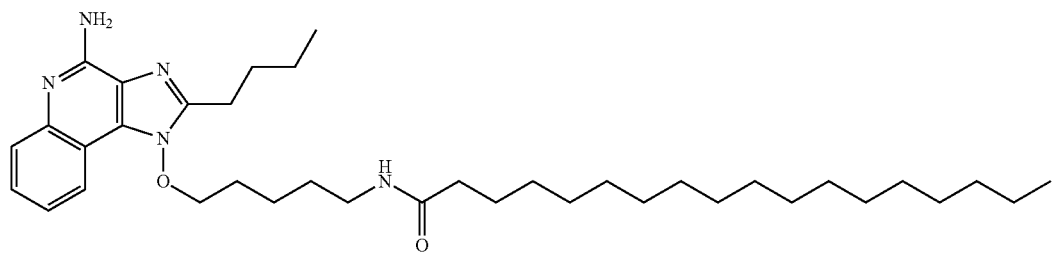 [SMILES: CCCCCCCCCCCCCCCCCC(=O)NCCCCCOn1c(CCCC)nc2c(N)nc3ccccc3c21]

In a further embodiment, the prodrug is a drug-lipid moiety comprising an TLR inhibitor of the inventions, wherein the TLR inhibitor comprises TR6 and further comprises CHEMS having the following structure:

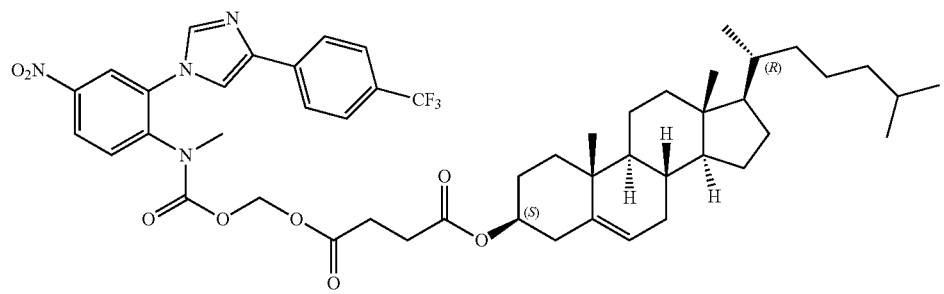

In one embodiment, the prodrug is a drug-lipid moiety comprising a TLR inhibitor set forth in FIG. 7.

In a further embodiment, the prodrug is a drug-lipid moiety comprising a TLR inhibitor of the invention. wherein the TLR inhibitor comprises the chemical composition(s) TR3

In a further embodiment, the prodrug is a drug-lipid moiety comprising a TLR inhibitor of the invention, wherein the TLR inhibitor comprises TR3 and further comprises CHEMS.

In a further embodiment, the prodrug is a drug-lipid moiety comprising a TLR inhibitor of the invention, wherein the TLR inhibitor comprises TR3 and further comprises Stearic Acid.

In a further embodiment, the prodrug is a drug-lipid moiety comprising a TLR inhibitor of the invention, wherein the TLR inhibitor comprises TR3 and further comprises CHEMS and whereby the LU is a hydromethylcarbamate linker.

In a further embodiment, the prodrug is a drug-lipid moiety comprising a TLR inhibitor of the invention, wherein the TLR inhibitor comprises TR3 and further comprises Stearic Acid and whereby the LU is a hydromethylcarbamate linker.

In a further embodiment, the prodrug is a drug-lipid moiety comprising an TLR inhibitor of the inventions, wherein the TLR inhibitor comprises TR3 having the following structure:

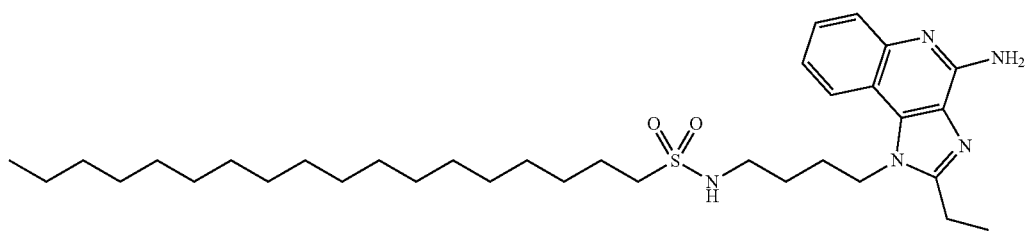 [SMILES: CCCCCCCCCCCCCCCCCCS(=O)(=O)NCCCCn1c(CC)nc2c(N)nc3ccccc3c21]

In additional embodiments of the disclosure the subject matter provides a TLR inhibitor prodrug comprising a lipid-conjugated therapeutic agent parent drug. In some embodiments, the prodrug comprises: (a) a monovalent drug moiety, (b) a monovalent lipid moiety, and (c) a bivalent linker moiety comprising a linkage unit that will degrade in vivo, such as a disulfide bond, wherein the monovalent drug moiety and the monovalent lipid moiety are linked (e.g., covalently linked) through the linker. The monovalent drug moiety and the monovalent lipid moieties can be monovalent derivatives of a chemical compound and a lipid, respectively. For instance, the monovalent derivative can be a deprotonated derivative of a chemical compound or lipid that comprises a hydroxyl, thiol, amino, or carboxylic acid group.

In further embodiments of the disclosure the subject matter provides a TLR inhibitor prodrug comprising a lipid-conjugated therapeutic agent parent drug. In some embodiments, the prodrug comprises: (a) a bivalent drug moiety, (b) a bivalent lipid moiety, and (c) a bivalent linker moiety comprising a linkage that will degrade in vivo, wherein the bivalent drug moiety and the bivalent lipid moiety are linked (e.g., covalently linked) through the linker. The bivalent drug moiety and the bivalent lipid moieties can be bivalent derivatives of a chemical compound and a lipid, respectively. For instance, the bivalent derivative can be a deprotonated derivative of a chemical compound or lipid that comprises a hydroxyl, thiol, amino, or carboxylic acid group.

One of ordinary skill in the art will appreciate and be enabled to make variations and modifications to the disclosed embodiment without altering the function and purpose of the invention disclosed herein. Such variations and modifications are intended within the scope of the present disclosure.

III.) Drug Moieties

Another aspect of the invention provides for novel TLR prodrug compound(s) with the following formula(s) denoted TR3, TR5, TR5(A), TR6, and TR6(A).

One of skill in the art will appreciate that a compound is useful as a TLR inhibitor (e.g., inhibits TLR, for example TLR1/2, TLR4, TLR7, TLR8 and/or TLR7/8). By way of brief background, TLR-1 (CD281) recognizes pathogen-associated molecular pattern with a specificity for gram-positive bacteria. TLR-1 is found on the epithelial cell layer that lines the small and large intestine and is an important player in the management of the gut microbiota and detection of pathogens. It is also found on the surface of macrophages and neutrophils. TLR1 recognizes peptidoglycan and (triacyl) lipopeptides in concert with TLR2 (as a heterodimer) and has been clearly shown to interact with TLR2. See, FARHAT, et. al., J. Leukoc. Biol. 83(3): 692-701 (2007) and JIN, et. al., Cell. 130(6): 1071-1082 (2007).

TLR2 (CD282) is a protein that in humans is encoded by the TLR2 gene. TLR2 is a membrane protein which is expressed on the surface of certain cells and recognizes foreign substances and passes on appropriate signals to the cells of the immune system. TLR2 is expressed most abundantly in peripheral blood leukocytes and mediates host response to Gram-positive bacteria and yeast via stimulation of NF-κB. See, BARRELLO, et. al., Int. J. Immun. & Pharm. 24(3): 549-556 (2011). TLR2 resides on the plasma membrane where it responds to lipid-containing PAMPs such as lipoteichoic acid and di- and tri-acylated cysteine-containing lipopeptides. It does this by forming dimeric complexes with either TLR 1 or TLR6 on the plasma membrane. See, BOTOS, et. al., Structure 19(4): 447-459 (2011).

TLR4 (CD284) is another member of the TLR family. Its activation leads to an intracellular signaling pathway NF-κB and inflammatory cytokine production which is responsible for activating the innate immune system. It is most well-known for recognizing lipopolysaccharide (LPS), a component present in many Gram-negative bacteria (e.g., *Neisseria* spp.) and select Gram-positive bacteria. Its ligands also include several viral proteins, polysaccharide, and a variety of endogenous proteins such as low-density lipoprotein, beta-defensins, and heat shock protein. See, BRUBAKER, et. al., Annual Rev. of Immun. 33:257-290 (2015). TLR4 signaling responds to signals by forming a complex using an extracellular leucine-rich repeat domain (LRR) and an intracellular toll/interleukin-1 receptor (TIR) domain. LPS stimulation induces a series of interactions with several accessory proteins which form the TLR4 complex on the cell surface. LPS recognition is initiated by an LPS binding to an LBP protein. The conformational changes of the TLR4 induce the recruitment of intracellular adaptor proteins containing the TIR domain which is necessary to activate the downstream signaling pathway. LU, et. al., Cytokine 42(2): 145-151 (2008). TLR4 is capable of activating MAPK and NF-κB pathways, implicating possible direct role of cell-autonomous TLR4 signaling in regulation of carcinogenesis, in particular, through increased proliferation of tumor cells, apoptosis inhibition and metastasis.

TLR7 is another member of the TLR family. TLR7 recognizes single-stranded RNA in endosomes, which is a common feature of viral genomes which are internalized by macrophages and dendritic cells. TLR7 recognizes single-stranded RNA of viruses such as HIV and HCV. See, HEIL, et. al., Science 303(5663): 1526-1529 (2004). TLR7 can recognize GU-rich single-stranded RNA. Id. However, the presence of GU-rich sequences in the single-stranded RNA is not sufficient to stimulate TLR7. TLR7 has been shown to play a significant role in the pathogenesis of autoimmune disorders such as Systemic Lupus Erythematosus (SLE) as well as in the regulation of antiviral immunity. In addition, due to their ability to induce robust production of anti-cancer cytokines such as interleukin-12, TLR7 agonists have been investigated for cancer immunotherapy.

Based on the foregoing, the present disclosure describes a class of TLR inhibitors.

In one embodiment, the class of TLR inhibitors inhibit TLR1/2.

In one embodiment, the class of TLR inhibitors inhibit TLR7.

In one embodiment, a drug moiety of the disclosure comprises a compound with the following chemical structure (denoted TR6):

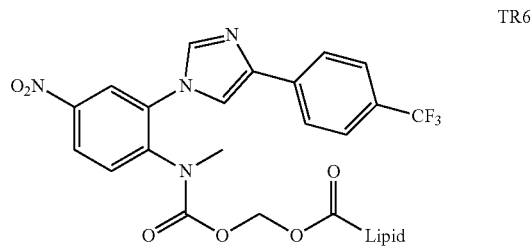

In an alternative embodiment, a drug moiety of the disclosure comprises a compound with the following chemical structure (denoted TR6(A)):

TR6(A)

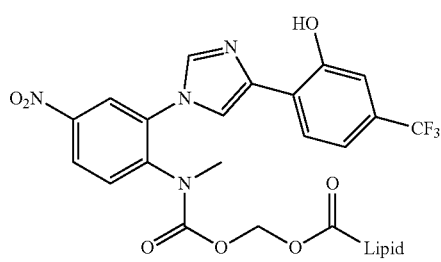

In one embodiment, a drug moiety of the disclosure comprises a compound with the following chemical structure (denoted TR5):

TR5

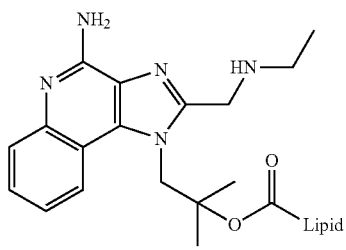

In an alternative embodiment, a drug moiety of the disclosure comprises a compound with the following chemical structure (denoted TR5(A)):

TR5(A)

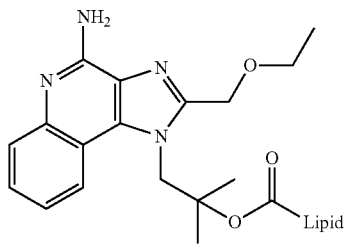

In one embodiment, a drug moiety of the disclosure comprises a compound with the following chemical structure(s) (denoted TR3):

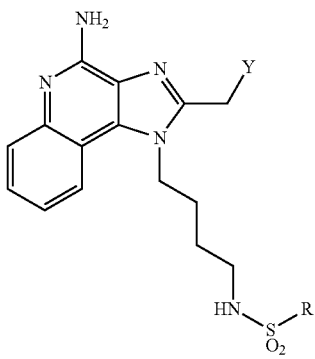

Wherein Y=$CH_3$, n-Pr, OEt, or NHEt; and

Wherein R=Saturated C12-C24 alkyl.

One of ordinary skill in the art will appreciate and be enabled to make variations and modifications to the disclosed embodiment without altering the function and purpose of the invention disclosed herein. Such variations and modifications are intended within the scope of the present disclosure.

IV.) Lipids

Generally speaking, and for the purposes of this disclosure, the term "lipid" is used in its broadest sense and comprises several sub-categories of lipids, including but not limited to, phospholipids/fatty acids. As it is appreciated by one of skill in the art, a phospholipid represents a class of lipids that are a major component of all cell membranes. Phospholipids can form lipid bilayers because of their amphiphilic characteristic. The structure of the phospholipid molecule generally consists of two hydrophobic fatty acid "tails" and a hydrophilic "head" consisting of a phosphate group that can be modified with simple organic molecules such as choline, ethanolamine, or serine. These two components are usually joined together by a glycerol molecule. A representative list of phospholipids/fatty acid(s) of the invention are set forth in Table III.

By way of brief background, at the most fundamental level, the properties of a liposome depend upon the subtle physicochemical interactions among the various lipid species in its composition. Individual lipids can be combined to form a myriad of superstructures including bilayers, and bilayer properties can be tuned to modulate drug release and membrane stability. In a simplified bilayer model acyl chain length dictates bilayer thickness and phase transition temperature (Tm), acyl chain saturation controls bilayer fluidity, and headgroup interactions impact inter- and intra-lipid molecular forces. Liposome behavior can be adjusted by incorporating synthetic lipids such as lipid prodrugs, fusogenic lipids and functionalizable lipids into the bilayer. See, KOHLI, et. al., J. Control Release, 0: pp. 274-287 (Sep. 28, 2014).

In one embodiment of the present disclosure, a TLR prodrug comprises a monovalent lipid moiety.

In one embodiment, a TLR prodrug comprises a bivalent lipid moiety.

In one embodiment, the lipid comprises a cholesterol with the following chemical structure:

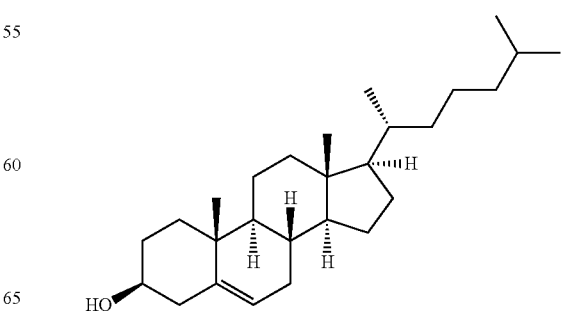

In one embodiment, the lipid comprises a DPPG with the following chemical structure:

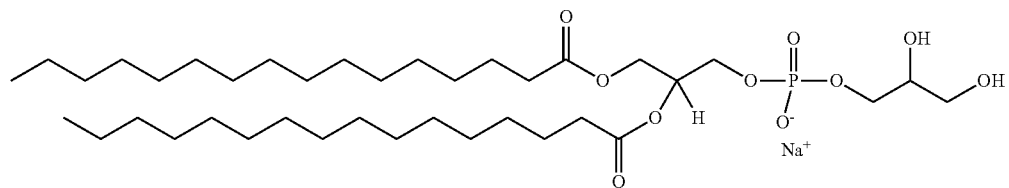 [SMILES: CCCCCCCCCCCCCCCC(=O)OCC(COP(=O)([O-])OCC(O)CO)OC(=O)CCCCCCCCCCCCCCC ; [Na+]]

In one embodiment, the lipid comprises a DMPG with the following chemical structure:

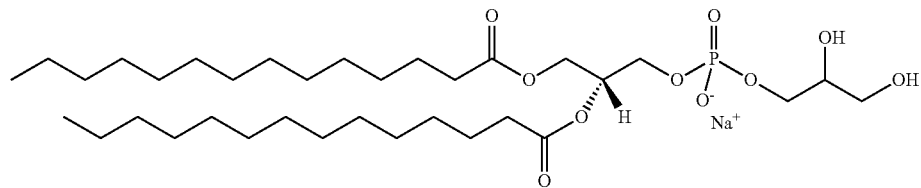 [SMILES: CCCCCCCCCCCCCC(=O)OC[C@H](COP(=O)([O-])OCC(O)CO)OC(=O)CCCCCCCCCCCCC ; [Na+]]

In one embodiment, the lipid comprises a Lyso PC with the following chemical structure:

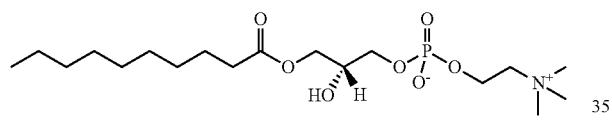

In one embodiment, the lipid comprises a (Δ9-Cis) PG.

In one embodiment, the lipid comprises a Soy Lyso PC with the following chemical structure:

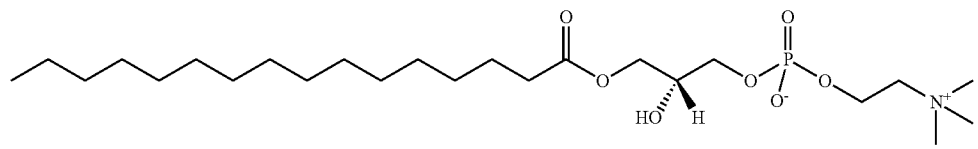 [SMILES: CCCCCCCCCCCCCCCC(=O)OC[C@@H](O)COP(=O)([O-])OCC[N+](C)(C)C]

In one embodiment, the lipid comprises a PG with the following chemical structure:

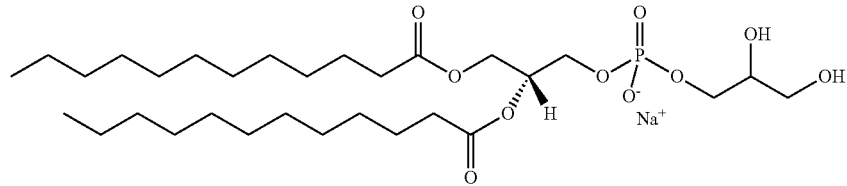 [SMILES: CCCCCCCCCCCC(=O)OC[C@H](COP(=O)([O-])OCC(O)CO)OC(=O)CCCCCCCCCCC ; [Na+]]

In one embodiment, the lipid comprises a C16 PEG2000 Ceramde with the following chemical structure:

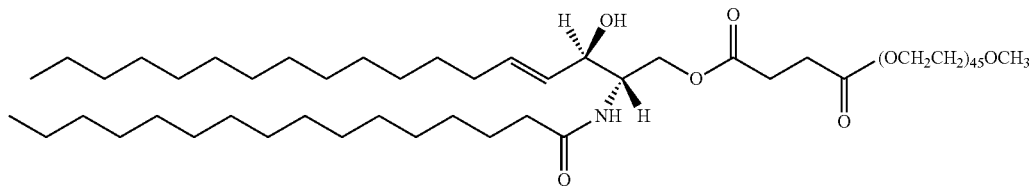

In one embodiment, the lipid comprises a cholesterol hemisuccinate ("CHEMS") with the following chemical structure:

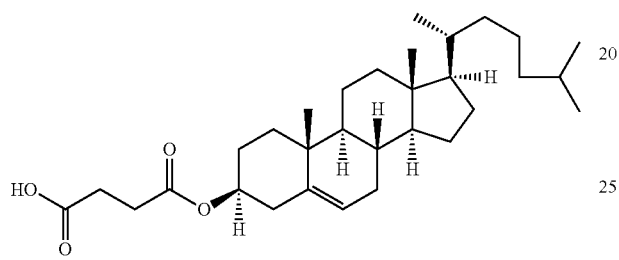

In one embodiment, the lipid comprises a class of lipids having the following chemical structure denoted Formula III

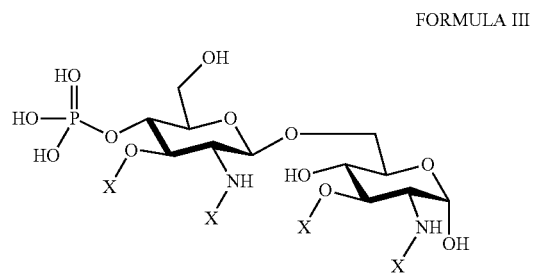

FORMULA III

Wherein, in exemplary embodiments of FORMULA III:

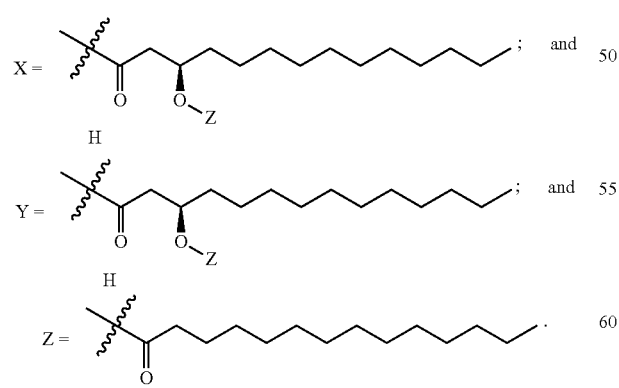

In one embodiment, a lipid moiety of the disclosure comprises a compound with the following chemical structure (denoted TR8):

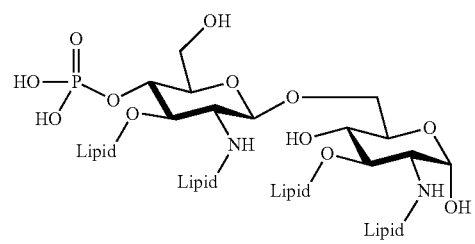

TR8

See, GIGG J., et. al., Carb. Res, 141(1); pp. 91-97 (1985).

In one embodiment, the lipid comprises a class of lipids having the following chemical structure denoted Formula IV:

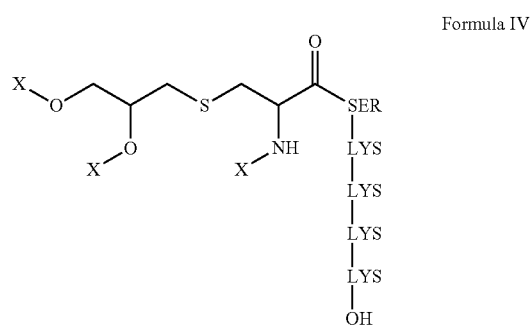

Formula IV

Wherein, in exemplary embodiments of FORMULA IV:

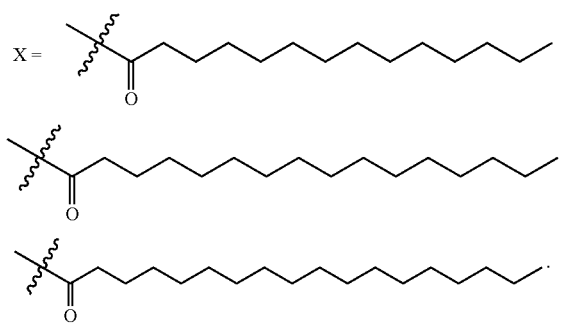

In one embodiment, a lipid moiety of the disclosure comprises a compound with the following chemical structure (denoted TR11):

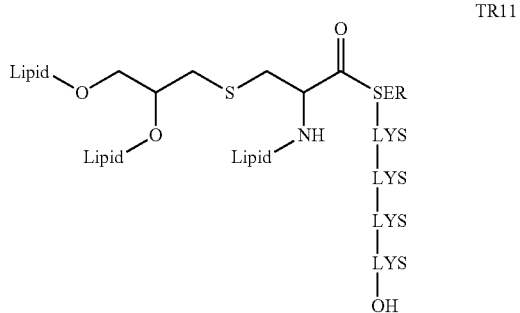

See, KAUR, et. al., RSC Advances 8, pp. 9587-9686 (2018).

In a further embodiment, a lipid moiety of the disclosure comprises a class of invariant natural killer T (iNKT) cells.

In a further embodiment, a lipid moiety of the disclosure comprises Alpha-galactosylceramide (α-GalCer).

By way of reference, a further list of the chemical formulas and abbreviation(s) of the lipids disclosed herein is set forth in Table I.

In an additional embodiment, the lipid comprises a phospholipid/fatty acid disclosed herein and set forth in Table Ill.

In a further embodiment, the lipid comprises a Stearic acid.

In addition, the TLR prodrugs and/or liposome(s) of the disclosure may comprise one or more helper lipids which are also referred to herein as "helper lipid components". The helper lipid components are preferably selected from the group comprising phospholipids and steroids. Phospholipids are preferably di- and monoester of the phosphoric acid. Preferred members of the phospholipids are phosphoglycerides and sphingolipids. Steroids, as used herein, are naturally occurring and synthetic compounds based on the partially hydrogenated cyclopenta[a]phenanthrene. Preferably, the steroids contain 21 to 30 C atoms. A particularly preferred steroid is cholesterol.

It is to be noted that although not wishing to be bound by any theory, due to the particular mol percentages of the helper lipid(s) contained in the lipid compositions according to the present invention, which helper lipid can be either a PEG-free helper lipid or in particular a PEG-containing helper lipid, surprising effects can be realized, more particularly if the content of any of this kind of helper lipid is contained within the concentration range specified herein.

In a further aspect of the present invention, lipid compositions which are preferably present as lipoplexes or liposomes, preferably show a neutral or overall anionic charge. The anionic lipid is preferably any neutral or anionic lipid described herein. The lipid composition comprises in a preferred embodiment any helper lipid or helper lipid combination as well as any TLR inhibitor as described herein. In a further embodiment the composition according to the present invention containing nucleic acid(s) forms lipoplexes. In a preferred embodiment the term lipoplexes as used herein refers to a composition composed of neutral or anionic lipid, neutral helper lipid and TLR inhibitor of the invention. For reference into the usage of helper lipids in the art, see, by way of example, U.S. Patent Application Publication 2011/0178164; OJEDA, et. al., Int. J. of Pharmaceutics (March 2016); DABKOWSKA, et. al., J. R. Soc. Interface 9, pp. 548-561 (2012); and MOCHIZUKI, et. al., Biochimica et. Biophysica Acta, 1828, pp. 412-418 (2013).

In a preferred embodiment, the helper lipids of the invention comprise the helper lipids set forth in Table II.

In one embodiment, a TLR prodrug comprises a lipid of the invention, wherein the lipid is CHEMS and wherein the drug moiety is TR6.

In one embodiment, a TLR prodrug comprises a lipid of the invention, wherein the lipid is CHEMS and wherein the drug moiety is TR6, further comprising a LU and wherein the LU is a hydromethylcarbamate linker.

In one embodiment, a TLR prodrug comprises a lipid of the invention, wherein the lipid is CHEMS and wherein the drug moiety is TR6, further comprising a LU and wherein the LU is a hydromethylcarbamate linker, further comprising a helper lipid component, wherein the helper lipid component comprises a helper lipid of Table II.

In one embodiment, a TLR prodrug comprises a lipid of the invention, wherein the lipid is CHEMS and wherein the drug moiety is TR6 and wherein the CHEMS is monovalent.

In one embodiment, a TLR prodrug comprises a lipid of the invention, wherein the lipid is Stearic Acid and wherein the drug moiety is TR6.

In one embodiment, a TLR prodrug comprises a lipid of the invention, wherein the lipid is Stearic Acid and wherein the drug moiety is TR6 and wherein the Stearic Acid is monovalent.

In one embodiment, a TLR prodrug comprises a lipid of the invention, wherein the lipid is Stearic Acid and wherein the drug moiety is TR6, further comprising a LU and wherein the LU is a hydromethylcarbamate linker.

In one embodiment, a TLR prodrug comprises a lipid of the invention, wherein the lipid is Stearic Acid and wherein the chemical composition is TR6, further comprising a LU and wherein the LU is a hydromethylcarbamate linker, further comprising a helper lipid component, wherein the helper lipid component comprises a helper lipid of Table II.

In one embodiment, a TLR prodrug comprises a lipid of the invention, wherein the lipid is CHEMS and wherein the drug moiety is TR5(B).

In one embodiment, a TLR prodrug comprises a lipid of the invention, wherein the lipid is CHEMS and wherein the drug moiety is TR5(B), further comprising a LU and wherein the LU is a hydromethylcarbamate linker.

In one embodiment, a TLR prodrug comprises a lipid of the invention, wherein the lipid is CHEMS and wherein the drug moiety is TR5(B), further comprising a LU and wherein the LU is a hydromethylcarbamate linker, further comprising a helper lipid component, wherein the helper lipid component comprises a helper lipid of Table II.

In one embodiment, a TLR prodrug comprises a lipid of the invention, wherein the lipid is CHEMS and wherein the drug moiety is TR5(B) and wherein the CHEMS is monovalent.

In one embodiment, a TLR prodrug comprises a lipid of the invention, wherein the lipid is Stearic Acid and wherein the drug moiety is TR5(B).

In one embodiment, a TLR prodrug comprises a lipid of the invention, wherein the lipid is Stearic Acid and wherein the drug moiety is TR5(B) and wherein the Stearic Acid is monovalent.

In one embodiment, a TLR prodrug comprises a lipid of the invention, wherein the lipid is Stearic Acid and wherein the drug moiety is TR5(B), further comprising a LU and wherein the LU is a hydromethylcarbamate linker.

In one embodiment, a TLR prodrug comprises a lipid of the invention, wherein the lipid is Stearic Acid and wherein the chemical composition is TR5(B), further comprising a LU and wherein the LU is a hydromethylcarbamate linker, further comprising a helper lipid component, wherein the helper lipid component comprises a helper lipid of Table II.

In one embodiment, a TLR prodrug comprises a lipid of the invention, wherein the lipid is CHEMS and wherein the drug moiety is TR3.

In one embodiment, a TLR prodrug comprises a lipid of the invention, wherein the lipid is CHEMS and wherein the drug moiety is TR3, further comprising a LU and wherein the LU is a hydromethylcarbamate linker.

In one embodiment, a TLR prodrug comprises a lipid of the invention, wherein the lipid is CHEMS and wherein the drug moiety is TR3, further comprising a LU and wherein the LU is a hydromethylcarbamate linker, further comprising a helper lipid component, wherein the helper lipid component comprises a helper lipid of Table II.

In one embodiment, a TLR prodrug comprises a lipid of the invention, wherein the lipid is CHEMS and wherein the drug moiety is TR3 and wherein the CHEMS is monovalent.

In one embodiment, a TLR prodrug comprises a lipid of the invention, wherein the lipid is Stearic Acid and wherein the drug moiety is TR3.

In one embodiment, a TLR prodrug comprises a lipid of the invention, wherein the lipid is Stearic Acid and wherein the drug moiety is TR3 and wherein the Stearic Acid is monovalent.

In one embodiment, a TLR prodrug comprises a lipid of the invention, wherein the lipid is Stearic Acid and wherein the drug moiety is TR3, further comprising a LU and wherein the LU is a hydromethylcarbamate linker.

In one embodiment, a TLR prodrug comprises a lipid of the invention, wherein the lipid is Stearic Acid and wherein the chemical composition is TR3, further comprising a LU and wherein the LU is a hydromethylcarbamate linker, further comprising a helper lipid component, wherein the helper lipid component comprises a helper lipid of Table II.

One of ordinary skill in the art will appreciate and be enabled to make variations and modifications to the disclosed embodiment without altering the function and purpose of the invention disclosed herein. Such variations and modifications are intended within the scope of the present disclosure.

V.) Linkage Unit(s) ("LU")

In some embodiments, the presently disclosed subject matter provides prodrugs comprising drug-lipid conjugates that include biodegradable linkages, such as esters, thioesters, and other linkers known in the art.

Exemplary embodiments of ester chemistry are set forth herein:

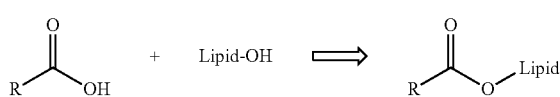

In some embodiments, the prodrug is a drug-lipid conjugate, whereby the drug-lipid conjugate is cleaved by an esterase.

In one embodiment, a prodrug of the invention comprises a LU via a secondary amine, amide, or aniline using the following schema:

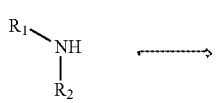

Secondary Amine, amide, or aniline

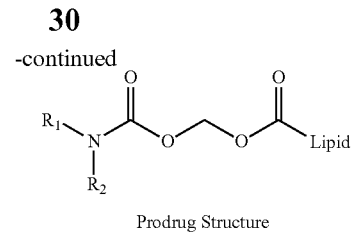

Prodrug Structure

An exemplary synthesis is as follows:

Synthesis

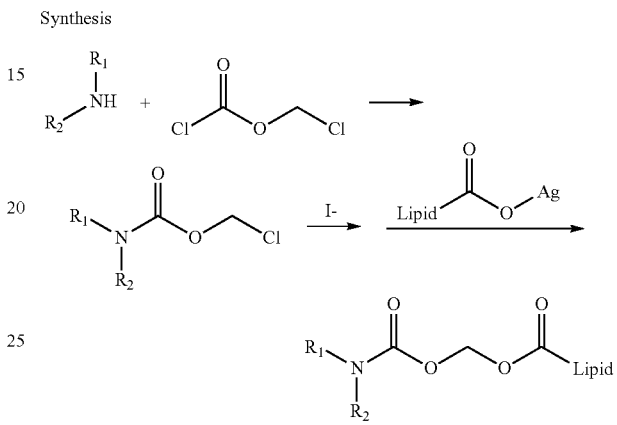

Cleavage of the prodrug structure comprising a secondary amine, amide, or aniline is obtained via esterase hydrolysis of the secondary amine, amide, or aniline prodrug under the following exemplary synthesis:

Esterase Hydrolysis of Secondary Amine/Amide/Aniline Prodrug

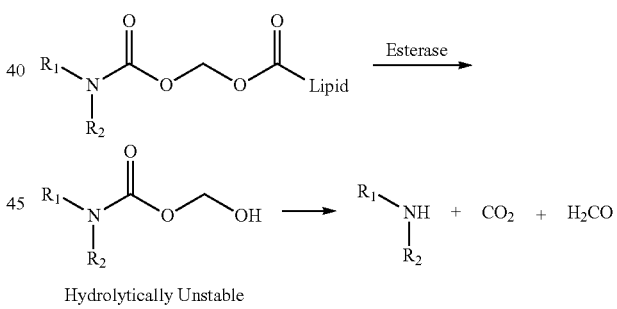

Hydrolytically Unstable

Wherein:

$R_1$ and $R_2$ can be and molecule which connects a N via a C.

In one embodiment, the secondary amide nitrogen of the TR6 drug moiety is conjugated to CHEMS via a hydromethylcarbamate linker.

In one embodiment, the secondary amide nitrogen of the TR6(A) drug moiety is conjugated to CHEMS via a hydromethylcarbamate linker.

In one embodiment, the secondary amide nitrogen of the TR5 drug moiety is conjugated to CHEMS via a hydromethylcarbamate linker.

In one embodiment, the secondary amide nitrogen of the TR5(A) drug moiety is conjugated to CHEMS via a hydromethylcarbamate linker.

In one embodiment, the secondary amide nitrogen of the TR5(B) drug moiety is conjugated to CHEMS via a hydromethylcarbamate linker.

One of ordinary skill in the art will appreciate and be enabled to make variations and modifications to the disclosed embodiment without altering the function and purpose of the invention disclosed herein. Such variations and modifications are intended within the scope of the present disclosure.

VI.) Nanocarrier(s)

Generally speaking, and for the purposes of this disclosure nanocarrier(s) are within the scope of the invention. A nanocarrier is nanomaterial being used as a transport module for another substance, such as a drug. Commonly used nanocarriers include micelles, polymers, carbon-based materials, liposomes, and other substances. Because of their small size, nanocarriers can deliver drugs to otherwise inaccessible sites around the body. Nanocarriers can include polymer conjugates, polymeric nanoparticles, lipid-based carriers, dendrimers, carbon nanotubes, and gold nanoparticles. Lipid-based carriers include both liposomes and micelles.

In addition, nanocarriers are useful in the drug delivery process because they can deliver drugs to site-specific targets, allowing drugs to be delivered in certain organs or cells but not in others. Site-specificity poses a major therapeutic benefit since it prevents drugs from being delivered to the wrong places. In addition. nanocarriers show promise for use in chemotherapy because they can help decrease the adverse, broader-scale toxicity of chemotherapy on healthy, fast growing cells around the body. Since chemotherapy drugs can be extremely toxic to human cells, it is important that they are delivered to the tumor without being released into other parts of the body.

Generally speaking, there are four (4) methods in which nanocarriers can deliver drugs and they include passive targeting, active targeting, pH specificity, and temperature specificity.

Passive targeting refers to a nanocarrier's ability to travel down a tumor's vascular system, become trapped, and accumulate in the tumor. This accumulation is caused by the enhanced permeability and retention effect. The leaky vasculature of a tumor is the network of blood vessels that form in a tumor, which contain many small pores. These pores allow nanocarriers in, but also contain many bends that allow the nanocarriers to become trapped. As more nanocarriers become trapped, the drug accumulates at the tumor site. This accumulation causes large doses of the drug to be delivered directly to the tumor site.

Active targeting involves the incorporation of targeting modules such as ligands or antibodies on the surface of nanocarriers that are specific to certain types of cells around the body. Generally, nanocarriers have a high surface-area to volume ratio allowing for multiple ligands to be incorporated on their surfaces.

Additionally, certain nanocarriers will only release the drugs they contain in specific pH ranges. pH specificity also allows nanocarriers to deliver drugs directly to a tumor site. This is due to the fact that tumors are generally more acidic than normal human cells, with a pH around 6.8. Normal tissue has a pH of around 7.4. Thus, nanocarriers that only release drugs at certain pH ranges can therefore be used to release the drug only within acidic tumor environments. High acidic environments cause the drug to be released due to the acidic environment degrading the structure of the nanocarrier. Generally, these nanocarriers will not release drugs in neutral or basic environments, effectively targeting the acidic environments of tumors while leaving normal body cells untouched. This pH sensitivity can also be induced in micelle systems by adding copolymer chains to micelles that have been determined to act in a pH independent manor. See, WU, et al., Biomaterials, 34(4): 1213-1222 (2012). These micelle-polymer complexes also help to prevent cancer cells from developing multi-drug resistance. The low pH environment triggers a quick release of the micelle polymers, causing a majority of the drug to be released at once, rather than gradually like other drug treatments.

Additionally, some nanocarriers have also been shown to deliver drugs more effectively at certain temperatures. Since tumor temperatures are generally higher than temperatures throughout the rest of the body, around 40° C., this temperature gradient helps act as safeguard for tumor-specific site delivery. See, REZAEI, et. al., Polymer, 53(16): 3185-3197 (2012).

As disclosed herein, lipid-based nanocarriers, such as liposomes are within the scope of this invention. Lipid-based nanoparticles (LBNPs or LNPs) such as liposomes, solid lipid nanoparticles (SLN) and nanostructured lipid carriers (NLC) can transport hydrophobic and hydrophilic molecules, display exceptionally low or no toxicity, and increase the time of drug action by means of a prolonged half-life and a controlled release of the drug. Lipid nanoparticles can include chemical modifications to avoid the detection by the immune system (gangliosides or polyethylene glycol (PEG)) or to improve the solubility of the drug. In addition, they can be prepared in formulations sensitive to the pH in order to promote drug release in an acid environment and can also be associated with small molecules or antibodies that recognize tumor cells or their receptors (such as folic acid (FoA)). Nanodrugs can also be used in combination with other therapeutic strategies to improve the response of patients. See, GARCIA-PINEL, et. al., Nanomaterials 9(639) (2019).

In various embodiments silicasome drug carriers described herein comprise a porous silica (or other material) nanoparticle (e.g., a silica body having a surface and defining a plurality of pores that are suitable to receive molecules therein) coated with a lipid bilayer. The fact that the nanoparticle is referred to as a silica nanoparticle does not preclude materials other than silica from also being incorporated within the silica nanoparticle. In some embodiments, the silica nanoparticle may be substantially spherical with a plurality of pore openings through the surface providing access to the pores. However, in various embodiments the silica nanoparticle can have shapes other than substantially spherical shapes. Thus, for example, in certain embodiments the silica nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface of defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments the pores are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm.

In other embodiments, the pore diameters are between 1.5 and 2.5 nm. Silica nanoparticles having other pore sizes may be prepared, for example, by using different surfactants or swelling agents during the preparation of the silica nanoparticles. In various embodiments the nanoparticles can include particles as large (e.g., average or median diameter (or another characteristic dimension) as about 1000 nm. However, in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticles range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm.

In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization techniques known in the art. Further examples of mesoporous silica nanoparticles include, but are not limited to, MCM-41, MCM-48, and SBA-15. See, KATIYARE, et. al., J. Chromotog. 1122(1-2): 13-20 (2006).

Methods of making porous silica nanoparticles are well known to those of skill in the art. In certain embodiments mesoporous silica nanoparticle are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (See, e.g., TREWYN et al. (2007) Chem. Eng. J. 137(1): 23-29).

In certain embodiments mesoporous particles can also be synthesized using a simple sol-gel method (See, e.g., NANDIYANTO, et al. (2009) Microporous and Mesoporous Mat. 120(3): 447-453). In certain embodiments tetraethyl orthosilicate can also be used with an additional polymer monomer as a template. In certain embodiments 3-mercaptopropyl)trimethoxysilane (MPTMS) is used instead of TEOS.

In certain embodiments the mesoporous silica nanoparticles are cores are synthesized by a modification of the sol/gel procedure described by MENG et. al. (2015) ACS Nemo, 9(4): 3540-3557.

While the methods described herein have been demonstrated with respect to porous silica nanoparticles (e.g., mesoporous silica), it will be recognized by those skilled in the art that similar methods can be used with other porous nanoparticles. Numerous other mesoporous materials that can be used in drug delivery nanoparticles are known to those of skill in the art. For example, in certain embodiments mesoporous carbon nanoparticles could be utilized.

Mesoporous carbon nanoparticles are well known to those of skill in the art (See, e.g., HUANG et. al. (2016) Carbon, 101: 135-142; ZHU et. al. (2014) Asian J. Pharm. Sci., 9(2): 82-91; and the like).

Similarly, in certain embodiments, mesoporous polymeric particles can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by MENG, et. al. (2006) Chem. Mat. 6(18): 4447-4464.

The nanoparticles described herein are illustrative and non-limiting. Using the teachings provided herein numerous other lipid bilayer coated nanoparticles will be available to one of skill in the art.

In one embodiment, the invention teaches nanocarriers which comprise TLR prodrugs.

In one embodiment, the invention teaches nanocarriers which comprise TLR prodrugs, wherein the TLR prodrug comprises TR3.

In one embodiment, the invention teaches nanocarriers which comprise TLR prodrugs, wherein the TLR prodrug comprises TR6.

In one embodiment, the invention teaches nanocarriers which comprise TLR prodrugs, wherein the TLR prodrug comprises TR5.

In one embodiment, the invention teaches a nanocarrier comprising a liposome, wherein the lipid comprises CHEMS.

In one embodiment, the invention teaches a nanocarrier comprising a liposome, wherein the lipid comprises Stearic Acid.

In one embodiment, the invention teaches a nanocarrier comprising a liposome, wherein the lipid comprises CHEMS and whereby the liposome further comprises a TLR prodrug.

In one embodiment, the invention teaches a nanocarrier comprising a liposome, wherein the lipid comprises CHEMS and whereby the liposome further comprises TR6.

In one embodiment, the invention teaches a nanocarrier comprising a liposome, wherein the lipid comprises CHEMS and whereby the liposome further comprises TR3.

In one embodiment, the invention teaches a nanocarrier comprising a liposome, wherein the lipid comprises CHEMS and whereby the liposome further comprises TR5.

In one embodiment, the invention teaches a nanocarrier comprising a liposome, wherein the lipid comprises CHEMS and whereby the liposome further comprises TR5 (B).

In one embodiment, the invention teaches a nanocarrier comprising a liposome, wherein the lipid comprises Stearic Acid and whereby the liposome further comprises a TLR inhibitor.

In one embodiment, the invention teaches a nanocarrier comprising a liposome, wherein the lipid comprises Stearic Acid and whereby the liposome further comprises TR3.

In one embodiment, the invention teaches a nanocarrier comprising a liposome, wherein the lipid comprises Stearic Acid and whereby the liposome further comprises TR6.

In one embodiment, the invention teaches a nanocarrier comprising a liposome, wherein the lipid comprises Stearic Acid and whereby the liposome further comprises TR5(B).

In one embodiment, the invention teaches nanocarriers which comprise TLR lipid moieties.

In one embodiment, the invention teaches a nanocarrier comprising a TLR lipid moiety, whereby the lipid moiety further comprises TR8.

In one embodiment, the invention teaches a nanocarrier comprising a TLR lipid moiety, whereby the lipid moiety further comprises TR11.

In one embodiment, the invention teaches a nanocarrier comprising a TLR lipid moiety, whereby the lipid moiety further comprises Alpha-galactosylceramide ($\alpha$-GalCer).

The scope of the disclosure teaches three (3) non-limiting possible treatment modalities using the formulated prodrugs of the invention. See, PCT Patent Publication No. WO2018/213631.

The first treatment modality involves combination of a TLR prodrug in combination with another therapeutic (e.g., another formulated prodrug which inhibits TLR (e.g., TLR1/2, TLR4, TLR7, TLR8, and/or TLR7/8), a chemotherapy agent (such as an ICD-inducing chemotherapy), etc.) into a single liposome that allows systemic (or local) biodistribution and drug delivery to tumor sites. The dual-delivery approach achieved synergistic enhancement of adaptive and innate immunity, leading to a significant improvement in animal survival. In certain embodiments the nanocarrier comprises a vesicle (i.e., a lipid bilayer enclosing a fluid).

A second treatment modality Involves local delivery to a tumor or peri-tumoral region, of an agent that inhibits TLR in combination with a lipid (e.g., a liposome) that comprises an inhibitor of TLR (e.g., TLR1/2, TLR4, TLR7, TLR8, and/or TLR7/8). It is demonstrated that such local delivery of a TLR inhibitor in combination with a TLR prodrug induces cytotoxic tumor killing, and tumor shrinkage at the local site. These adaptive immune responses are accompanied by boosting of the innate immune system, as reflected by CRT expression, as well as the activation of a DC population, particularly well-suited for generating cytotoxic T cell responses.

A third treatment modality involves vaccination utilizing dying cancer cells {e.g., KPC cells) in which inhibition of TLR is induced ex vivo. It is discovered that such vaccination can generate a systemic immune response that can interfere with tumor growth at a remote site as well as allowing adoptive transfer to non-immune animals. One of skill in the art will appreciate and be enabled to perform methods the treatment modalities provided herein.

VII.) Liposomes

In one aspect, the presently disclosed subject matter is based on an approach for providing a prodrug of the disclosure (See, section entitled Prodrugs) suitable for incorporation into a nanocarrier comprising lipid coating layers to provide enhanced delivery of the corresponding prodrugs and for providing combination therapies including the prodrugs. The advantages for using prodrugs of the invention include the facilitation of controlled formulation into an LNP of the disclosure (e.g., a liposome). This allows the prodrug to be maintained in an inactive form during systemic circulation, which allows the liposome to release the active agent after engulfment by a cell, for example within a tumor.

In certain embodiments one or more TLR prodrugs (e.g., any one or more of the TLR prodrugs inhibitors taught in Formula I or Formula II, and/or TR3, TR5, TR5(A), TR5(B), TR6, TR6(A)) (See, section entitled "Prodrugs") are formulated a lipid moiety that forms a vesicle (e.g., a liposome) structure in aqueous solution or that can form a component of a lipid bilayer comprising a liposome.

In certain embodiments one or more TLR Lipid Moieties (e.g., any one or more of the TLR lipid moieties taught in Formula III or Formula IV, and/or TR8, TR11) (See, section entitled "Lipids") are formulated and/or co-formulated within a vesicle (e.g., a liposome) structure in aqueous solution or that can form a component of a lipid bilayer comprising a liposome.

The liposomes can be used directly or provided as components in a combined formulation (e.g., in combination with another drug moiety, or lipid moiety, or therapeutic modality as disclosed herein).

In certain embodiments, the liposome that is formulated with the TLR prodrug comprises a lipid, PHGP, vitamin E, cholesterol, and/or a fatty acid.

In certain embodiments, the liposome that is formulated comprises a lipid moiety comprising TR8.

In certain embodiments, the liposome that is formulated comprises a lipid moiety comprising TR11.

In certain embodiments, the liposome that is formulated comprises a lipid moiety comprising Formula III.

In certain embodiments, the liposome that is formulated comprises a lipid moiety comprising Formula IV.

In certain embodiments, the liposome that is formulated comprises a lipid moiety comprising Alpha-galactosylceramide ($\alpha$-GalCer).

In one embodiment, the liposome comprises cholesterol.

In one embodiment, the liposome comprises DPPG.

In one embodiment, the liposome comprises DMPG.

In one embodiment, the liposome Lyso PC.

In one embodiment, the liposome ($\Delta$9-Cis) PG.

In one embodiment, the liposome comprises Soy Lyso PC.

In one embodiment, the liposome comprises PG.

In one embodiment, the liposome comprises PA-PEG3-mannose.

In one embodiment, the liposome comprises C16 PEG2000 Ceramide.

In one embodiment, the liposome comprises MPLA.

In one embodiment, the liposome comprises 3-Deacly MPLA.

In one embodiment, the liposome comprises CHEMS.

In one embodiment, the liposome comprises Stearic Acid.

In one embodiment, the liposome comprises a phospholipid set forth in Table Ill.

In one embodiment, the liposome comprises TR6 and further comprises CHEMS and further comprises a LU wherein said LU is a hydromethylcarbamate linker.

In one embodiment, the liposome comprises TR6 and further comprises Stearic Acid and further comprises a LU wherein said LU is a hydromethylcarbamate linker.

In one embodiment, the liposome comprises TR6 and further comprises CHEMS and further comprises a LU wherein said LU is a hydromethylcarbamate linker and further comprises a helper lipid set forth in Table II.

In one embodiment, the liposome comprises TR6 and further comprises a Stearic Acid and further comprises a LU wherein said LU is a hydromethylcarbamate linker and further comprises a helper lipid set forth in Table II.

In one embodiment, the liposome comprises TR5.

In one embodiment, the liposome comprises TR5 and further comprises CHEMS and further comprises a LU wherein said LU is a hydromethylcarbamate linker.

In one embodiment, the liposome comprises TR5 and further comprises Stearic Acid and further comprises a LU wherein said LU Is a hydromethylcarbamate linker.

In one embodiment, the liposome comprises TR5 and further comprises CHEMS and further comprises a LU wherein said LU is a hydromethylcarbamate linker and further comprises a helper lipid set forth in Table II.

In one embodiment, the liposome comprises TR5 and further comprises a Stearic Acid and further comprises a LU wherein said LU is a hydromethylcarbamate linker and further comprises a helper lipid set forth in Table II.

In one embodiment, the liposome comprises TR5(B) and further comprises CHEMS and further comprises a LU wherein said LU is a hydromethylcarbamate linker.

In one embodiment, the liposome comprises TR5(B) and further comprises Stearic Acid and further comprises a LU wherein said LU is a hydromethylcarbamate linker.

In one embodiment, the liposome comprises TR5(B) and further comprises CHEMS and further comprises a LU wherein said LU is a hydromethylcarbamate linker and further comprises a helper lipid set forth in Table II.

In one embodiment, the liposome comprises TR5(B) and further comprises a Stearic Acid and further comprises a LU wherein said LU is a hydromethylcarbamate linker and further comprises a helper lipid set forth in Table II.

In one embodiment, the liposome comprises TR3 and further comprises CHEMS and further comprises a LU wherein said LU is a hydromethylcarbamate linker.

In one embodiment, the liposome comprises TR3 and further comprises Stearic Acid and further comprises a LU wherein said LU is a hydromethylcarbamate linker.

In one embodiment, the liposome comprises TR3 and further comprises CHEMS and further comprises a LU wherein said LU is a hydromethylcarbamate linker and further comprises a helper lipid set forth in Table II.

In one embodiment, the liposome comprises TR3 and further comprises a Stearic Acid and further comprises a LU wherein said LU is a hydromethylcarbamate linker and further comprises a helper lipid set forth in Table II.

In one embodiment, the liposome of the disclosure comprises a TLR prodrug co-formulated with one or more additional immune modulating agents, whereby the immune modulating agents includes, but is not limited to, immunogenic-cell death inducing chemotherapeutics, IDO antagonists, sting agonists, CTLA4 inhibitors, PD-1 inhibitors, and/or prodrugs thereof.

In one embodiment, the liposome of the disclosure comprises a TLR prodrug co-formulated with one or more additional immune modulating agents, whereby the immune modulating agents includes, but is not limited to, neurokinin 1 (NK1) antagonists, and/or prodrugs thereof.

In one embodiment, the liposome of the disclosure comprises a TLR prodrug co-formulated with one or more additional immune modulating agents, whereby the immune modulating agents includes, but is not limited to, A2aR antagonists, and/or prodrugs thereof.

In a preferred embodiment, the liposome comprises a TLR prodrug co-formulated with an ICD-inducing Chemotherapeutic.

In a preferred embodiment, the liposome comprises a TLR prodrug co-formulated with an ICD-inducing Chemotherapeutic selected from the list: doxorubicin (DOX), mitoxantrone (MTO), Oxaliplatin (OXA), Cyclophosphamide (CP), Bortezomib, Carfilzimib, or Paclitaxel.

In a preferred embodiment, the liposome comprises a TLR prodrug co-formulated with a Toll Receptor TLR agonist/Prodrug.

In a preferred embodiment, the liposome comprises a TLR prodrug co-formulated with Toll Receptor (TLR) agonist/Prodrug selected from the list: Resiquimod (R848), Gardiquimod, 852A, DSR 6434, Telratolimod, CU-T12-9, monophosphoryl Lipid A (MPLA), 3D(6-acyl)-PHAD®, SMU127, Pam3CSK4, or 3D-PHAD®.

In a preferred embodiment, the liposome comprises a TLR prodrug co-formulated with an PD-1 inhibitor/Prodrug.

In a preferred embodiment, the liposome comprises a TLR prodrug co-formulated with an PD-1 inhibitor/Prodrug, selected from the list: AUNP12, CA-170, or BMS-986189 or prodrugs thereof.

In a preferred embodiment, the liposome comprises a TLR prodrug co-formulated with doxorubicin (DOX).

In a preferred embodiment, the liposome comprises a TLR prodrug co-formulated with mitoxantrone (MTO).

In a preferred embodiment, the liposome comprises a TLR prodrug co-formulated with doxorubicin (DOX) and an PD-1 prodrug.

In a preferred embodiment, the liposome comprises a TLR prodrug co-formulated with mitoxantrone (MTO) and a PD-1 prodrug.

In a preferred embodiment, the liposome comprises a TLR prodrug co-formulated with doxorubicin (DOX) and an IDO antagonist/prodrug.

In a preferred embodiment, the liposome comprises a TLR prodrug co-formulated with mitoxantrone (MTO) and an IDO antagonist/prodrug.

In a preferred embodiment, the liposome comprises a TLR prodrug co-formulated with doxorubicin (DOX) and a PD-1 prodrug and an IDO antagonist/prodrug.

In a preferred embodiment, the liposome comprises a TLR prodrug co-formulated with mitoxantrone (MTO) and a PD-1 prodrug and an IDO antagonist/prodrug.

In a preferred embodiment, the liposome comprises a TLR prodrug co-formulated with an IDO antagonist/prodrug.

In a preferred embodiment, the liposome comprises a TLR prodrug co-formulated with an IDO antagonist/prodrug.

In a preferred embodiment, the liposome comprises a TLR prodrug co-formulated with an IDO antagonist/prodrug and a PD-1 prodrug, In a preferred embodiment, the liposome comprises a TLR prodrug co-formulated with an IDO antagonist/prodrug and a PD-1 prodrug.

In a preferred embodiment, the liposome comprises TR6 co-formulated with doxorubicin (DOX).

In a preferred embodiment, the liposome comprises TR6 co-formulated with mitoxantrone (MTO).

In a preferred embodiment, the liposome comprises TR6 co-formulated with doxorubicin (DOX) and/or an IDO prodrug and/or an IDO antagonist/prodrug.

In a preferred embodiment, the liposome comprises TR6 co-formulated with mitoxantrone (MTO) and/or an IDO prodrug and/or an IDO antagonist/prodrug.

In a preferred embodiment, the liposome comprises TR6 co-formulated with NK1.

In a preferred embodiment, the liposome comprises TR6 co-formulated with MTO and TR8.

In a preferred embodiment, the liposome comprises TR6 co-formulated with DOX and a A2aR prodrug.

In a preferred embodiment, the liposome comprises TR5 co-formulated with DOX

In a preferred embodiment, the liposome comprises TR5 co-formulated with a A2aR prodrug.

In a preferred embodiment, the liposome comprises TR5 co-formulated with DOX and a A2aR prodrug.

In a preferred embodiment, the liposome comprises TR5 co-formulated with an A2aR prodrug and an anti-PD1 antibody.

In a preferred embodiment, the liposome comprises TR5 co-formulated with an A2aR prodrug and an IDO prodrug.

In a preferred embodiment, the liposome comprises TR5 (B) co-formulated with doxorubicin (DOX).

In a preferred embodiment, the liposome comprises TR5 (B) co-formulated with mitoxantrone (MTO).

In a preferred embodiment, the liposome comprises TR5 (B) co-formulated with doxorubicin (DOX) and/or an IDO prodrug and/or an IDO antagonist/prodrug.

In a preferred embodiment, the liposome comprises TR5 (B) co-formulated with mitoxantrone (MTO) and/or an IDO prodrug and/or an IDO antagonist/prodrug.

In a preferred embodiment, the liposome comprises TR8 co-formulated with doxorubicin (DOX).

In a preferred embodiment, the liposome comprises TR8 co-formulated with mitoxantrone (MTO).

In a preferred embodiment, the liposome comprises TR8 co-formulated with doxorubicin (DOX) and/or a TLR prodrug and/or an IDO antagonist/prodrug.

In a preferred embodiment, the liposome comprises TR8 co-formulated with mitoxantrone (MTO) and/or a TLR prodrug and/or an IDO antagonist/prodrug.

In a preferred embodiment, the liposome comprises TR11 co-formulated with doxorubicin (DOX).

In a preferred embodiment, the liposome comprises TR11 co-formulated with mitoxantrone (MTO).

In a preferred embodiment, the liposome comprises TR11 co-formulated with doxorubicin (DOX) and/or a TLR prodrug and/or an IDO antagonist/prodrug.

In a preferred embodiment, the liposome comprises TR11 co-formulated with mitoxantrone (MTO) and/or a TLR prodrug and/or an IDO antagonist/prodrug.

In another preferred embodiment, the liposome comprises a solid-lipid nanoparticle (SLNP) comprising a liposome which comprises a TLR prodrug.

One of skill in the art will appreciate and understand that solubility is one of most common problems faced by the artisan in the drug development process. Chemical conjugation of a drug/anti-cancer agents via lipid molecules (i.e., lipid-based prodrugs) provides a platform to solve the problem of formulating the drugs in an aqueous suspension. The major advantages of delivering drug(s) with lipid conjugation (lipid-based prodrugs) lies on its ability to improve pharmacokinetics/half-life and targeted delivery.

With suitable selection of lipid molecules, lipid-based prodrug(s) can be integrated/formulated in a liposomal formulation using techniques known in the art, which has many more advantages over conventional drug delivery system. (KOHLI, et. al., J. Control Release, 0: pp 274-287 (Sep. 28, 2014); and GARCIA-PINEL, et. al., Nanomaterials 9:638 (2019). The advantage of combining lipid-prodrug with liposomes is twofold: (i) liposomes containing lipid-prodrug not only increase the solubility of the drug/prodrug itself, but (ii) also have the ability to encapsulate multiple drugs (both hydrophilic and lipophilic) (see, section entitled nanocarriers).

For the purposes of this disclosure, the major advantage of liposome formulations are as follows:
  i) biocompatibility/biodegradability and no general toxicity of the liposome's formulations;
  ii) flexibility and manipulation of size and surface charge depending on the required purpose. Liposome formulation(s), for the purposes of this disclosure, can have a size range of 40-150 nm in diameter and a surface charge in the range of −40 to +40 mV; and
  iii) Liposomes of the invention have either a single or multiple lipid-prodrugs as the constituent lipid portion of the liposome(s). Additionally, multiple drugs (e.g., that work in different mechanism of action) and with different solubility profile (hydrophilic or lipophilic) can be formulated (either in the lipid bilayers or in the hydrophilic core) in these liposomes.

As one of ordinary skill in the art will appreciate, all methods of making liposomes involve four (4) basic stages:
  (i) Drying down lipids from organic solvent;
  (ii) Dispersing the lipid in aqueous solution;
  (iii) Purifying the resultant liposome; and
  (iv) Analyzing the final product.

See, AKBARZADEH, et. al., Nanoscale Research Letters, 8:102 (2013).

Another aspect of the invention discloses liposomal encapsulation technology (LET) which is a delivery technique used to transmit drugs. LET is a method of generating sub-microscopic foams called liposomes, which encapsulate numerous materials. These 'liposomes' form a barrier around their contents, which is resistant to enzymes in the mouth and stomach, alkaline solutions, digestive juices, bile salts, and intestinal flora that are generated in the human body, as well as free radicals. The contents of the liposomes are, therefore, protected from oxidation and degradation, This protective phospholipid shield or barrier remains undamaged until the contents of the liposome are delivered to the exact target gland, organ, or system where the contents will be utilized (See, section entitled nanocarriers).

In one embodiment, liposome(s) of the disclosure are synthesized using a plurality of different ratios of TLR prodrugs, TLR lipid moieties, lipids, and/or lipid-prodrugs. As disclosed herein, the TLR prodrugs may comprise helper lipids as disclosed herein (See, for example Table II).

In one embodiment, liposome(s) of the disclosure are synthesized using a plurality of different ratios of TLR prodrugs, TLR lipid moieties, lipids, and/or lipid-prodrugs. As disclosed herein, the TLR prodrugs may further comprise DSPE-PEGs.

In a preferred embodiment, the liposomes of the invention comprise a composition having the following ratio(s):

| Constituent of the Liposome | Amount (% w/w) |
| --- | --- |
| Lipid 1 (lipid-prodrug) | 5-60 |
| Lipid 2 (lipid-prodrug) | 0-60 |
| Helper lipids | 0-50 |
| DSPEG-PEG 2000 | 2-5 |

In a further preferred embodiment, the liposomes of the invention comprise a composition having the following ratio(s):

| Constituent of the Liposome | Amount (% w/w) |
| --- | --- |
| Lipid 1 (lipid-prodrug) | 5-60 |
| Helper lipids | 0-50 |
| DSPEG-PEG 2000 | 2-5 |

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises TR5 and CHEMS.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises TR5 and Stearic Acid.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises TR6 and CHEMS.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises TR6 and Stearic Acid.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises TR3 and Stearic Acid.

One of ordinary skill in the art will appreciate and be enabled to make variations and modifications to the disclosed embodiment without altering the function and purpose of the invention disclosed herein. Such variations and modifications are intended within the scope of the present disclosure.

VIII.) Pharmaceutical Formulation

As used herein, the term "drug" is synonymous with "pharmaceutical". In certain embodiments, the liposome of the disclosure is fabricated to an encapsulated dosage form to and given to a patient for the treatment of disease.

Generally speaking, pharmaceutical formulation is the process in which different chemical substances are combined to a pure drug substance to produce a final drug product. Formulation studies involve developing a preparation of the drug which is both stable and acceptable to the patient. For orally taken drugs, this usually involves incorporating the drug into a tablet or a capsule. It is important to appreciate that a dosage form contains a variety of other substances apart from the drug itself, and studies have to be carried out to ensure that the drug is compatible with these other substances.

An excipient is an inactive substance used as a carrier for the active ingredients of a drug product, in this case a liposome comprising a TLR prodrug. In addition, excipients can be used to aid the process by which a drug product is manufactured. The active substance is then dissolved or mixed with an excipient. Excipients are also sometimes used to bulk up formulations with very potent active ingredients, to allow for convenient and accurate dosage. Once the active ingredient has been purified, it cannot stay in purified form for an extended amount of time. In many cases it will denature, fall out of solution, or stick to the sides of the container.

To stabilize the active ingredient, excipients are added to ensure that the active ingredient stays active and is stable for a long enough period of time that the shelf-life of the product makes it competitive with other products and safe for the end-user. Examples of excipients include but are not limited to, anti-adherents, binders, coatings, disintegrants, fillers, diluents, flavors, colors, lubricants, and preservatives. The final formulation comprises and active ingredient and excipients which are then enclosed in the pharmaceutical dosage form.

Pre-formulation involves the characterization of a drug's physical, chemical, and mechanical properties in order to choose what other ingredients should be used in the preparation. Formulation studies then consider such factors as stability, particle size, polymorphism, pH, and solubility, as all of these can Influence bioavailability and hence the activity of a drug. The drug must be combined with inactive additives by a method which ensures that the quantity of drug present is consistent in each dosage unit (e.g., each vial). The dosage should have a uniform appearance.

It is unlikely that these studies will be complete by the time clinical trials commence. This means that simple preparations are developed initially for use in phase I clinical trials. These typically consist of vials, hand-filled capsules containing a small amount of the drug and a diluent. Proof of the long-term stability of these formulations is not required, as they will be used (tested) in a matter of days. However, long-term stability is critical in supply chain management since the time the final formulation is packaged until it reaches the patient can be several months or years. Consideration has to be given to what is called the drug load (i.e., the ratio of the active drug to the total contents of the dose). A low drug load may cause homogeneity problems. A high drug load may pose flow problems or require large capsules if the compound has a low bulk density. By the time phase III clinical trials are reached, the formulation of the drug should have been developed to be close to the preparation that will ultimately be used in the market.

A knowledge of stability is essential by this stage, and conditions must have been developed to ensure that the drug is stable in the preparation. If the drug proves unstable, it will invalidate the results from clinical trials since it would be impossible to know what the administered dose actually was. Stability studies are carried out to test whether temperature, humidity. oxidation, or photolysis (ultraviolet light or visible light) have any effect, and the preparation is analyzed to see if any degradation products have been formed. It is also important to check whether there are any unwanted interactions between the preparation and the container. If a plastic container is used, tests are carried out to see whether any of the ingredients become adsorbed on to the plastic, and whether any plasticizers, lubricants, pigments, or stabilizers leach out of the plastic into the preparation. Even the adhesives for the container label need to be tested, to ensure they do not leach through the plastic container into the preparation. The way a drug is formulated can avoid some of the problems associated with oral administration. Drugs are normally taken orally as tablets or capsules. The drug (active substance) itself needs to be soluble in aqueous solution at a controlled rate. Such factors as particle size and crystal form can significantly affect dissolution. Fast dissolution is not always ideal. For example, slow dissolution rates can prolong the duration of action or avoid initial high plasma levels.

In some embodiments, the nanocarrier (e.g., a liposome comprising a TLR prodrug) and/or the liposome comprising a TLR prodrug and co-formulated with an immune modulating agent are administered alone or in a mixture with a physiologically-acceptable carrier (such as physiological saline or phosphate buffer) selected in accordance with the route of administration and standard pharmaceutical practice. For example, when used as an injectable, the nanocarriers can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, 5% glucose and the like, including glycoproteins for enhanced stability, such as albumin, lipoprotein, globulin, etc. In compositions comprising saline or other salt-containing carriers, the carrier is preferably added following nanocarrier formation. Thus, after the nanocarrier is formed and loaded with suitable drug(s), the nanocarrier can be diluted into pharmaceutically acceptable carriers such as normal saline. Similarly, the TLR prodrug liposomes can be introduced into carriers that facilitate suspension of the nanomaterials (e.g., emulsions, dilutions, etc.).

The pharmaceutical compositions may be sterilized by conventional, well-known sterilization techniques. The resulting aqueous solutions, suspensions, dispersions, emulsions, etc., may be packaged for use or filtered under aseptic conditions. In certain embodiments the drug delivery nanocarriers (e.g., LB-coated nanoparticles) are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damage on storage. Lipophilic free-radical quenchers, such as alpha-tocopherol and water-soluble iron-specific chelators, such as ferrioxamine, are suitable and contemplated herein. The concentration of nanocarrier (e.g., liposome comprising TLR prodrugs) in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, nanocarriers composed of irritating lipids may be diluted to low concentrations to lessen inflammation at the site of administration. The amount of nanocarriers administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

One of skill in the art will appreciate that exact dosages will vary depending upon such factors as the particular TLR prodrugs and any co-formulated immune modulating agents and the desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases described herein the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the nanocarrier(s) can be approximately equal to that employed for the free drug. However as noted above, the nanocarriers described herein can significantly reduce the toxicity of the drug(s) administered thereby and significantly increase a therapeutic window. Accordingly, in some cases dosages in excess of those prescribed for the free drug(s) will be utilized.

One of ordinary skill in the art will appreciate and be enabled to make variations and modifications to the disclosed embodiment without altering the function and purpose of the invention disclosed herein. Such variations and modifications are intended within the scope of the present disclosure.

IX.) Combination Therapy

As the skilled artisan will appreciate and understand, cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Thus, the liposomes comprising TLR prodrugs of the present disclosure can be used in combination with one or more other enzyme/protein/receptor inhibitors or one or more therapies for the treatment of diseases, such as cancer or infections. Examples of diseases and indications treatable with combination therapies include those set forth in the present disclosure. Examples of cancers include, but are not limited to, solid tumors and liquid tumors, such as blood cancers. Examples of infections include viral infections, bacterial infections, fungus infections or parasite infections.

For example, the liposomes comprising TLR prodrugs of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, PI3K (alpha, beta, gamma, delta), CSF1R, KIT, FLK-II, KDR/FLK-1, FLK-4, flt-1, FGFR1, FGFR2, FGFR3, FGFR4, c-Met, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In further embodiments, the liposomes comprising TLR prodrugs of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), a TLR inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, olaparib, niraparib, veliparib, or talazoparib, an arginase inhibitor (INCB01158), a PD-1 inhibitor, a PD-1/L-1 inhibitor, a PD-1/L-2 inhibitor, and an adenosine receptor antagonist or combinations thereof.

In further embodiments, the liposomes comprising TLR prodrugs of the present disclosure can be combined with one or more activator of invariant natural killer T (iNKT) cells including but not limited to, α-galactosylceramida (α-Gal-Cer) and analogs thereof including, C8 Galactosyl(a) Ceramide, C16 Galactosyl(a) Ceramide, and C24:1 Galactosyl (a) Ceramide (Avanti Polar Lipids, Alabaster, Ala.).

Additionally, the liposomes comprising TLR prodrugs of the present disclosure can further be used in combination with other methods of treating cancers, for example by chemotherapy, irradiation therapy, tumor-targeted therapy, adjuvant therapy, immunotherapy or surgery.

Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like.

The liposomes comprising TLR prodrugs can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalTLRmide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalTLRmide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1/L2, or antibodies to cytokines (IL-10, TGF-.beta., etc.).

Examples of antibodies to PD-1 and/or PD-L1/L2 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

In addition, liposomes comprising TLR prodrugs of the present disclosure can be used in combination with one or more immune checkpoint inhibitors for the treatment of diseases, such as cancer or infections. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2.

In some embodiments, the immune checkpoint molecule is a stimulatory checkpoint molecule selected from CD27, CD28, CD40, ICOS, OX40, GITR and CD137. In further embodiments, the immune checkpoint molecule is an inhibitory checkpoint molecule selected from A2AR, B7-H3, B7-H4, BTLA, CTLA-4, TLR, KIR, LAG3, PD-1, TIM3, and VISTA. In further embodiments, the liposomes comprising TLR prodrugs provided herein can be used in combination with one or more agents selected from KIR inhibitors, TIGIT inhibitors, LAIR1 inhibitors, CD160 inhibitors, 2B4 inhibitors and TGFR beta inhibitors.

X.) Methods of Delivering Liposomes Comprising TLR Prodrugs to a Cell Expressing Toll-Like Receptor ("TLR")

As it is known in the art, a wide variety of compositions and methods for using prodrugs and/or liposomes to kill tumor cells are known in the art. In the context of cancers, typical methods entail administering to a mammal having a tumor, a biologically effective amount of a TLR prodrug of the disclosure, and/or a liposome of the disclosure comprising a TLR prodrug.

A typical embodiment is a method of delivering a therapeutic agent to a cell expressing TLR1/2, TLR4, TLR7, TLR8, and/or TLR7/8, comprising forming a TLR prodrug by conjugating a drug moiety of the disclosure with a lipid of the disclosure via a Linkage Unit, and exposing the cell to the TLR prodrug.

In one embodiment, the TLR prodrug comprises a drug moiety of Formula I and CHEMS conjugated via a LU comprising a hydromethylcarbamate linker.

In one embodiment, the TLR prodrug comprises a drug moiety of Formula I and Stearic Acid conjugated via a LU comprising a hydromethylcarbamate linker.

In one embodiment, the TLR prodrug comprises a drug moiety of Formula II and CHEMS conjugated via a LU comprising a hydromethylcarbamate linker.

In one embodiment, the TLR prodrug comprises a drug moiety of Formula II and Stearic Acid conjugated via a LU comprising a hydromethylcarbamate linker.

In one embodiment, the TLR prodrug comprises TR3 and CHEMS conjugated via a LU comprising a hydromethylcarbamate linker.

In one embodiment, the TLR prodrug comprises TR3 and Stearic Acid conjugated via a LU comprising a hydromethylcarbamate linker.

In one embodiment, the TLR prodrug comprises TR6 and CHEMS conjugated via a LU comprising a hydromethylcarbamate linker.

In one embodiment, the TLR prodrug comprises TR6 and Stearic Acid conjugated via a LU comprising a hydromethylcarbamate linker.

In one embodiment, the TLR prodrug comprises TR5(B) and CHEMS conjugated via a LU comprising a hydromethylcarbamate linker.

In one embodiment, the TLR prodrug comprises TR5(B) and Stearic Acid conjugated via a LU comprising a hydromethylcarbamate linker.

Another illustrative embodiment is a method of treating an individual suspected of suffering from metastasized cancer, comprising a step of administering parenterally to said individual a pharmaceutical composition comprising a therapeutically effective amount of a TLR prodrug produced by conjugating a drug moiety with a lipid of the disclosure via a Linkage Unit, and exposing the cell to the TLR prodrug.

In one embodiment, the TLR prodrug comprises a drug moiety of Formula I and CHEMS conjugated via a LU comprising a hydromethylcarbamate linker.

In one embodiment, the TLR prodrug comprises a drug moiety of Formula I and Stearic Acid conjugated via a LU comprising a hydromethylcarbamate linker.

In one embodiment, the TLR prodrug comprises a drug moiety of Formula II and CHEMS conjugated via a LU comprising a hydromethylcarbamate linker.

In one embodiment, the TLR prodrug comprises a drug moiety of Formula II and Stearic Acid conjugated via a LU comprising a hydromethylcarbamate linker.

In one embodiment, the TLR prodrug comprises TR3 and CHEMS conjugated via a LU comprising a hydromethylcarbamate linker.

In one embodiment, the TLR prodrug comprises TR3 and Stearic Acid conjugated via a LU comprising a hydromethylcarbamate linker.

In one embodiment, the TLR prodrug comprises TR6 and CHEMS conjugated via a LU comprising a hydromethylcarbamate linker.

In one embodiment, the TLR prodrug comprises TR6 and Stearic Acid conjugated via a LU comprising a hydromethylcarbamate linker.

In one embodiment, the TLR prodrug comprises TR5(B) and CHEMS conjugated via a LU comprising a hydromethylcarbamate linker.

In one embodiment, the TLR prodrug comprises TR5(B) and Stearic Acid conjugated via a LU comprising a hydromethylcarbamate TLR prodrugs, liposomes, and co-formulated liposomes of the present disclosure inhibit the activity of TLR protein/protein interaction and, thus, are useful in treating diseases and disorders associated with activity of TLR and the diseases and disorders.

In further embodiments of the disclosure, the TLR prodrugs, liposomes, or pharmaceutically acceptable salts or stereoisomers thereof, are useful for therapeutic administration to enhance, stimulate and/or increase immunity in cancer, chronic infection, or sepsis, including enhancement of response to vaccination.

In further embodiments, the present disclosure provides a method for inhibiting the TLR (e.g., TLR1/2, TLR4, TLR7, TLR8, and/or TLR7/8) T-cell function. The method includes administering to an individual or a patient a TLR prodrug, liposomes, and/or of any of the formulas as described herein (e.g., TR3, TR6, TR6(A), TR5, TR5(A) and/or TR5(B)), or of a TLR prodrug, liposomes, and nano-encapsulated TLR inhibitor prodrugs as recited in any of the claims and described herein, or a pharmaceutically acceptable salt or a stereoisomer thereof. The TLR prodrug, liposomes, and nano-encapsulated TLR inhibitor prodrugs of the present disclosure can be used alone, in combination with other agents or therapies or as an adjuvant or neoadjuvant for the treatment of diseases or disorders, including cancer and other diseases. For the uses and methods described herein, any of the TLR prodrugs, liposomes, and nano-encapsulated TLR prodrugs of the disclosure, including any of the embodiments thereof, may be used.

In addition, The TLR prodrugs, liposomes, and nano-encapsulated TLR inhibitor prodrugs of the present disclosure inhibit the TLR function, resulting In a TLR pathway blockade.

In further embodiments, the present disclosure provides treatment of an individual or a patient in vivo using TLR prodrugs, liposomes, and nano-encapsulated TLR inhibitor prodrug or a salt or stereoisomer thereof such that growth of cancerous tumors is inhibited.

TLR prodrugs, liposomes, and nano-encapsulated TLR inhibitor prodrugs, or of any of the formulas as described herein (e.g., TR3, TR6, TR6(A), TR5, TR5(A) and/or TR5(B)), or TLR prodrugs, liposomes, and nano-encapsulated TLR inhibitor prodrugs as recited in any of the claims and described herein, or a salt or stereoisomer thereof, can be used to inhibit the growth of cancerous tumors.

In the alternative, TLR prodrugs, liposomes, and nano-encapsulated TLR prodrugs of the disclosure, or of any of the formulas as described herein, or a compound as recited in any of the claims and described herein (e.g., TR3, TR6, TR6(A), TR5, TR5(A) and/or TR5(B)), or a salt or stereoisomer thereof, can be used in conjunction with other agents or standard cancer treatments, as described in this disclosure.

In a further embodiment, the present disclosure provides a method for inhibiting growth of tumor cells in vitro. The method includes contacting the tumor cells in vitro with TLR prodrugs, liposomes, and nano-encapsulated TLR inhibitor prodrugs of the disclosure, or of any of the formulas as described herein (e.g., TR3, TR6, TR6(A), TR5, TR5(A) and/or TR5(B)), or of a TLR prodrug, liposomes, and nano-encapsulated TLR inhibitor prodrugs as recited in any of the claims and described herein, or of a salt or stereoisomer thereof.

In a further embodiment, the present disclosure provides a method for inhibiting growth of tumor cells in a patient. The method includes contacting the tumor cells with TLR prodrugs, liposomes, and nano-encapsulated TLR inhibitor prodrugs of the disclosure, or of any of the formulas as described herein (e.g., TR3, TR6, TR6(A), TR5, TR5(A) and/or TR5(B)), or of a TLR prodrug, liposomes, and nano-encapsulated TLR inhibitor prodrugs as recited in any of the claims and described herein, or of a salt or stereoisomer thereof.

XI.) Methods of Treating Cancer(s) and Other Immunological Disorder(s)

Another embodiment of the present disclosure is a method for treating cancer. The method comprises administering to a patient, a therapeutically effective amount of a liposome comprising a TLR prodrug (i.e., TR3, TR6, TR6(A), TR5, TR5(A) and/or TR5(B)) herein, a compound as recited in any of the claims and described herein, or a salt thereof. Examples of cancers include those whose growth may be inhibited using TLR inhibitors of the disclosure and TLR prodrugs of the disclosure and cancers typically responsive to immunotherapy.

In some embodiments, the present disclosure provides a method of enhancing, stimulating and/or increasing the immune response in a patient. The method includes administering to the patient a therapeutically effective amount of a TLR prodrug and/or a liposome comprising the same (i.e., TR3, TR6, TR6(A), TR5, TR5(A) and/or TR5(B)), a compound or composition as recited in any of the claims and described herein, or a salt thereof.

Non-limiting examples of cancers that are treatable using the liposomes comprising TLR prodrugs, TLR prodrugs and co-formulated liposomes of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express TLR.

In some embodiments, cancers treatable with liposomes, or TLR prodrugs of the present disclosure include melanoma (e.g., metastatic malignant melanoma), renal cancer (e.g., clear cell carcinoma), prostate cancer (e.g., hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability ($MSI^{high}$). Additionally, the disclosure includes refractory or recurrent malignancies whose growth may be inhibited using the liposomes, or TLR prodrugs or co-formulated liposomes of the disclosure.

In additional embodiments, cancers that are treatable using the formulated and/or co-formulated liposomes or TLR prodrugs of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In further embodiments, cancers that are treatable using the formulated and/or co-formulated liposomes or TLR prodrugs of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In addition, in some embodiments, the formulated and/or co-formulated liposomes, or TLR prodrugs of the present disclosure can be used to treat sickle cell disease and sickle cell anemia.

Furthermore, in some embodiments, diseases and indications that are treatable using the formulated and/or co-formulated liposomes, or TLR prodrugs of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Additionally, TLR and/or kynurenine pathway blockade with formulated and/or co-formulated liposomes, or TLR prodrugs of the present disclosure can also be used for treating infections such as viral, bacteria, fungus, and parasite infections.

The present disclosure provides a method for treating infections such as viral infections. The method includes administering to a patient, a therapeutically effective amount of a formulated and/or co-formulated liposome or TLR prodrugs or any of the formulas as described herein (i.e., TR3, TR6, TR6(A), TR5, TR5(A) and/or TR5(B)) as recited in any of the claims and described herein, a salt thereof.

Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, Ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In addition, the present disclosure provides a method for treating bacterial infections. The method includes administering to a patient, a therapeutically effective amount of a formulated and/or co-formulated liposome or TLR prodrugs, or any of the formulas as described herein (i.e., TR3, TR6, TR6(A), TR5, TR5(A) and/or TR5(B)) as recited in any of the claims and described herein, or a salt thereof.

Examples of pathogenic bacteria causing infections treatable by methods of the disclosure, include but are not limited to, *chlamydia, rickettsia* bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

In addition, the present disclosure provides a method for treating fungus infections. The method includes administering to a patient, a therapeutically effective amount of a formulated and/or co-formulated liposome or TLR prodrugs, or any of the formulas as described herein (i.e., TR3, TR6, TR6(A), TR5, TR5(A) and/or TR5(B)) as recited in any of the claims and described herein, or a salt thereof.

Examples of pathogenic fungi causing infections treatable by methods of the disclosure, include but are not limited to, *Candida* (*albicans, krusei, glabrata, tropicalis*, etc.), *Cryptococcus neoformans, Aspergillus* (*fumigatus, Niger*, etc.), Genus *Mucorales* (*Mucor, absldia, rhizophus*), *Sporothrix schenkii, Blastomyces dermatitidis, Paracoccidioides brasiliensis, Coccidioides immitis* and *Histoplasma capsulatum*.

Additionally, the present disclosure provides a method for treating parasite infections. The method includes administering to a patient, a therapeutically effective amount of a formulated and/or co-formulated liposome or TLR prodrugs, or any of the formulas as described herein (i.e., TR3, TR6, TR6(A), TR5, TR5(A) and/or TR5(B)) as recited in any of the claims and described herein, or a salt thereof.

Examples of pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In a further set of embodiments that are within the scope of this disclosure, the formulated and/or co-formulated liposomes, or TLR prodrugs, or any of the formulas as described herein (i.e., TR3, TR6, TR6(A), TR5, TR5(A) and/or TR5 (B)) are useful in preventing or reducing the risk of developing any of the diseases referred to in this disclosure; e.g., preventing or reducing the risk of developing a disease, condition or disorder in an individual who may be predisposed to the disease, condition or disorder but does not yet experience or display the pathology or symptomatology of the disease.

XII.) Kits/Articles of Manufacture

For use in the laboratory, prognostic, prophylactic, diagnostic, and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a formulated and/or co-formulated liposome that is or can be detectably labeled and/or is loaded with a TLR prodrug of the disclosure. Kits can comprise a container comprising a drug unit. The kit can include all or part of the formulated and/or co-formulated liposomes and/or a TLR prodrug.

The kit of the invention will typically comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic, or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as formulated and/or co-formulated liposomes and/or TLR prodrugs are within the scope of this disclosure. The article of manufacture typically comprises at least one container and at least one label. Suitable containers include, for example, bottles, vials, syringes, and test tubes. The containers can be formed from a variety of materials such as glass, metal, or plastic. The container can hold formulated and/or co-formulated liposomes loaded with TLR prodrugs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be formulated and/or co-formulated liposomes loaded with TLR prodrugs and/or TLR prodrugs as disclosed herein.

The article of manufacture can further comprise a second container comprising a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXEMPLARY EMBODIMENTS

Among the provided embodiments are:
1) A TLR prodrug composition comprising,
   (i) a drug moiety;
   (ii) a lipid moiety; and
   (iii) a linkage unit ("LU"),
   whereby the drug moiety comprises a TLR agonist and whereby the LU conjugates the drug moiety with the lipid moiety.
2) The TLR prodrug of claim 1, further comprising the chemical structure set forth in FORMULA I.
3) The TLR prodrug of claim 1, further comprising the chemical structure set forth in FORMULA II.
4) The TLR prodrug of claim 1, wherein the drug moiety comprises the chemical structure set forth as TR5.
5) The TLR prodrug of claim 1, wherein the drug moiety comprises the chemical structure set forth as TR5(A).
6) The TLR prodrug of claim 1, wherein the drug moiety comprises the chemical structure set forth as TR6.
7) The TLR prodrug of claim 1, wherein the drug moiety comprises the chemical structure set forth as TR6(A).
8) The TLR prodrug of claim 1, wherein the drug moiety comprises the chemical structure set forth as TR3.
9) The TLR prodrug of claim 1, wherein the LU is a hydromethylcarbamate linker.
10) The TLR prodrug of claim 1, wherein the lipid moiety comprises a lipid set forth in Table I.
11) The TLR prodrug of claim 1, wherein the lipid moiety comprises a lipid set forth in Table Ill.
12) The TLR prodrug of claim 1, wherein the lipid moiety comprises CHEMS.
13) The TLR prodrug of claim 1, wherein the lipid moiety comprises Stearic Acid.
14) A TLR prodrug composition comprising,
   (i) a drug moiety, whereby the drug moiety comprises TR5;
   (ii) a lipid moiety, whereby the lipid moiety comprises CHEMS; and (iii) LU, whereby the LU comprises a hydromethylcarbamate linker.

15) A TLR prodrug composition comprising,
   (i) a drug moiety, whereby the drug moiety comprises TR5;
   (ii) a lipid moiety, whereby the lipid moiety comprises Stearic Acid; and
   (iii) a LU, whereby the LU comprises a hydromethylcarbamate linker.

16) A TLR prodrug composition comprising,
   (i) a drug moiety, whereby the drug moiety comprises TR5(A);
   (ii) a lipid moiety, whereby the lipid moiety comprises CHEMS; and
   (iii) LU, whereby the LU comprises a hydromethylcarbamate linker.

17) A TLR prodrug composition comprising,
   (i) a drug moiety, whereby the drug moiety comprises TR5(A);
   (ii) a lipid moiety, whereby the lipid moiety comprises Stearic Acid; and
   (iii) a LU, whereby the LU comprises a hydromethylcarbamate linker.

18) A TLR prodrug composition comprising,
   (i) a drug moiety, whereby the drug moiety comprises TR6;
   (ii) a lipid moiety, whereby the lipid moiety comprises CHEMS; and
   (iii) LU, whereby the LU comprises a hydromethylcarbamate linker.

19) A TLR prodrug composition comprising,
   (i) a drug moiety, whereby the drug moiety comprises TR6;
   (ii) a lipid moiety, whereby the lipid moiety comprises Stearic Acid; and
   (iii) a LU, whereby the LU comprises a hydromethylcarbamate linker.

20) A TLR prodrug composition comprising,
   (i) a drug moiety, whereby the drug moiety comprises TR6(A);
   (ii) a lipid moiety, whereby the lipid moiety comprises CHEMS; and
   (iii) LU, whereby the LU comprises a hydromethylcarbamate linker.

21) A TLR prodrug composition comprising,
   (i) a drug moiety, whereby the drug moiety comprises TR6(A);
   (ii) a lipid moiety, whereby the lipid moiety comprises Stearic Acid; and
   (iii) a LU, whereby the LU comprises a hydromethylcarbamate linker.

22) A TLR prodrug composition comprising,
   (i) a drug moiety, whereby the drug moiety comprises TR3;
   (ii) a lipid moiety, whereby the lipid moiety comprises Stearic Acid; and
   (iii) a LU, whereby the LU comprises a hydromethylcarbamate linker.

23) A liposome comprising, a TLR prodrug whereby the liposome releases an active TLR inhibitor after cleavage of a LU.

24) The liposome of claim 23, wherein the LU is a hydromethylcarbamate linker.

25) The liposome of claim 23, further comprising a helper lipid, whereby the helper lipid is set forth in Table II.

26) The liposome of claim 23, wherein the TLR prodrug comprises TR3, TR5, TR5(A), and/or TR5(B).

27) The liposome of claim 23, wherein the TLR prodrug comprises TR6 and/or TR6(A).

28) The liposome of claim 23, whereby the liposome is further co-formulated with an iNTK activator.

29) The liposome of claim 28, wherein the iNKT activator is Alpha-galactosylceramide (α-GalCer).

30) The liposome of claim 23, whereby the liposome is further co-formulated with an immune modulating agent, wherein the immune modulating agent is selected from the group consisting of other TLR agonists and/or prodrugs, immunogenic-cell death inducing chemotherapeutics, IDO antagonists, STING agonists, CTLA-4 inhibitors, PD-1/PD-L1 inhibitors and/or prodrugs thereof.

31) The liposome of claim 23, whereby the liposome is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

32) The liposome of claim 23, further comprising DOX.

33) The liposome of claim 23, further comprising MTO.

34) The liposome of claim 23, further comprising DOX.

35) The liposome of claim 23, further comprising MTO.

36) A kit comprising a liposome of claim 23.

37) A kit comprising a liposome of claim 26.

38) A kit comprising a liposome of claim 27.

39) A liposome comprising, a TLR lipid moiety, wherein the TLR Lipid moiety comprises a chemical structure set forth in FORMULA Ill.

40) A liposome comprising, a TLR lipid moiety, wherein the TLR Lipid moiety comprises a chemical structure set forth in FORMULA IV.

41) The liposome of claim 39, further comprising a helper lipid, whereby the helper lipid is set forth in Table II.

42) The liposome of claim 39, further comprising a helper lipid, whereby the helper lipid is set forth in Table II.

43) The liposome of claim 38, wherein the TLR prodrug comprises TR8.

44) The liposome of claim 40, wherein the TLR prodrug comprises TR11.

45) The liposome of claim 38, whereby the liposome is further co-formulated with an iNTK activator.

46) The liposome of claim 45, wherein the iNKT activator is Alpha-galactosylceramide (α-GalCer).

47) The liposome of claim 39, whereby the liposome is further co-formulated with an iNTK activator.

48) The liposome of claim 47, wherein the iNKT activator is Alpha-galactosylceramide (α-GalCer).

49) The liposome of claim 44, whereby the liposome is further co-formulated with an iNTK activator.

50) The liposome of claim 49, wherein the iNKT activator is Alpha-galactosylceramide (α-GalCer).

51) The liposome of claim 43, whereby the liposome is further co-formulated with an iNTK activator.

52) The liposome of claim 51, wherein the iNKT activator is Alpha-galactosylceramide (α-GalCer).

53) The liposome of claim 39, whereby the liposome is further co-formulated with an immune modulating agent, wherein the immune modulating agent is selected from the group consisting of immunogenic-cell death inducing chemotherapeutics, IDO antagonists, STING agonists, CTLA-4 inhibitors, PD-1/PD-L1 inhibitors and/or prodrugs thereof.

54) The liposome of claim 39, whereby the liposome is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

55) The liposome of claim 40, whereby the liposome is further co-formulated with an immune modulating agent, wherein the immune modulating agent is selected from the group consisting of immunogenic-cell death inducing chemotherapeutics, IDO antagonists, STING agonists, CTLA-4 inhibitors, PD-1/PD-L1 inhibitors and/or prodrugs thereof.

56) The liposome of claim 40, whereby the liposome is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

57) A method of treating a subject suffering or diagnosed with cancer comprising,
    (i) administering to a subject in need of such treatment an effective amount of a liposome, wherein the liposome comprises a TLR prodrug; and
    (ii) a pharmaceutically acceptable salt thereof.

58) The method of claim 57, wherein the TLR prodrug comprises TR3, TR5, TR5(A), and/or TR5(B).

59) The method of claim 57, wherein the liposome comprises TR3, TR5, TR5(A), and/or TR5(B) further co-formulated with and ICD-inducing chemotherapeutic.

60) The method of claim 57, wherein the liposome comprises TR3, TR5, TR5(A), and/or TR5(B) further co-formulated with an immune modulating agent.

61) The method of claim 57, wherein the liposome comprises TR3, TR5, TR5(A), and/or TR5(B) further co-formulated with an iNTK activator.

62) The method of claim 58, wherein the iNTK activator is Alpha-galactosylceramide (α-GalCer).

63) A method of treating a subject suffering or diagnosed with cancer comprising,
    (i) administering to a subject in need of such treatment an effective amount of a liposome, wherein the liposome comprises a TLR prodrug; and
    (ii) a pharmaceutically acceptable salt thereof.

64) The method of claim 63, wherein the TLR prodrug comprises TR6 and/or TR6(A).

65) The method of claim 63, wherein the liposome comprises TR6 and/or TR6(A) further co-formulated with and ICD-inducing chemotherapeutic.

66) The method of claim 63, wherein the liposome comprises TR6 and/or TR6(A) further co-formulated with an immune modulating agent.

67) The method of claim 63, wherein the liposome comprises TR6 and/or TR6(A) further co-formulated with an iNTK activator.

68) The method of claim 67, wherein the iNTK activator is Alpha-galactosylceramide (α-GalCer).

69) A method of treating a subject suffering or diagnosed with cancer comprising,
    (i) administering to a subject in need of such treatment an effective amount of a liposome, wherein the liposome comprises a TLR lipid moiety; and
    (ii) a pharmaceutically acceptable salt thereof.

70) The method of claim 69, wherein the TLR lipid moiety comprises TR8.

71) The method of claim 69, wherein the liposome comprises TR8 further co-formulated with and ICD-inducing chemotherapeutic.

72) The method of claim 69, wherein the liposome comprises TR8 further co-formulated with an immune modulating agent.

73) The method of claim 69, wherein the liposome comprises TR8 further co-formulated with an iNTK activator.

74) The method of claim 73, wherein the iNTK activator is Alpha-galactosylceramide (α-GalCer).

75) The method of claim 69, wherein the liposome comprises TR8 further co-formulated with 103.

76) A method of treating a subject suffering or diagnosed with cancer comprising,
    (i) administering to a subject in need of such treatment an effective amount of a liposome, wherein the liposome comprises a TLR lipid moiety; and
    (ii) a pharmaceutically acceptable salt thereof.

77) The method of claim 76, wherein the TLR lipid moiety comprises TR11.

78) The method of claim 76, wherein the liposome comprises TR11 further co-formulated with and ICD-inducing chemotherapeutic.

79) The method of claim 76, wherein the liposome comprises TR11 further co-formulated with an immune modulating agent.

80) The method of claim 76, wherein the liposome comprises TR11 further co-formulated with an iNTK activator.

81) The method of claim 80, wherein the iNTK activator is Alpha-galactosylceramide (α-GalCer).

EXAMPLES

Various aspects of the invention are further described and illustrated by way of the several examples that follow, none of which is intended to limit the scope of the invention.

Example 1: Chemical Synthesis of TR5(B) Prodrug Comprising Various Lipids

Chemical synthesis of a TR5(B) prodrug comprising various lipids, set forth for example, in Table(s) I and III is synthesized using the following protocol. First, Quinoline (1) is treated with valeric anhydride to yield Intermediate 2. Then, 4-aminobutanol (3) is treated with benzylchloroformate (4) to yield Intermediate 5. Then, Intermediate 5 is treated with N-hydroxyphthalimide, triphenylphosphine, and DIAD, followed by hydrazine to yield Intermediate 6. Then, Intermediate 6 and Intermediate 2 were heated with triethylamine to yield Intermediate 7. Then, Intermediate 7 was treated sequentially with mCPBA, ammonium hydroxide, benzenesulfonyl chloride, then heated with HCl to yield Intermediate 8. Finally, Intermediate 8 was treated with various lipid carboxylic acids to yield final product denoted TR5(B) (FIG. 1).

Example 2: Chemical Synthesis of TR6 Prodrug Comprising Various Lipids

Chemical synthesis of a TR6 prodrug comprising various lipids, set forth for example, in Table(s) I and III is synthesized using the following protocol. First, Fluoronitroaniline (1) is treated with methyl amine to yield Compound 2. Then, Compound 2 was treated with trimethylorthoformate to yield benzimidazole (3). Then, Benzimidazole (3) was treated with Compound 4 to yield Compound 5. Then, Compound 5 was treated with ammonium acetate to yield Compound 6. Then, Compound 6 was treated with chloromethylchloroformate (7) to yield Compound 8. Finally, Compound 8 was treated with various lipid acids (9) to yield final product denoted TR6 (FIG. 2).

Example 3: Chemical Synthesis of TR6 Prodrug Intermediate

In another experiment, a chemical synthesis of the TR6 prodrug intermediate was performed in the following manner. To a solution of Cu-T12-9 (5.50 g, 15.1 mmol, 1.00 eq) in THF (75.0 mL) was added LiHMDS (1 M, 18.2 mL, 1.20 eq) at −70° C. and the reaction mixture was stirred at −70° C. for 0.5 hr. Then a solution of compound 2a (2.94 g, 22.7 mmol, 2.02 mL, 1.50 eq) in THF (10 mL) was added to the mixture at −70° C. and stirred at −70° C. for another 1.5 hrs. LCMS showed that Cu-T12-9 (RT=0.934 min) was consumed incompletely, and the desired mass (RT=0.966 min) was detected. The reaction mixture was poured into saturated citric acid solution (100 mL) and extracted with ethyl acetate (150 mL*3). The organic layer was washed with brine (150 mL*2), dried over $Na_2SO_4$, filtered, and concentrated to give the crude product confirmed by LCMS and HPLC). The crude product was purified by prep-HPLC (column: Phenomenex luna C18 250*80 mm*10 um; mobile phase: [water (0.1% TFA)-ACN]; B %: 38ACN %-68ACN %, 21 min) and extracted with ethyl acetate (200 mL*2) directly. The combined organic layer was washed with brine (200 mL*3), dried over $Na_2SO_4$, filtered, and concentrated to give compound 2 (2.50 g, 5.50 mmol, 36.2% yield) as a yellow solid. The resulting compounds are shown in FIG. 6.

Example 4: Chemical Synthesis of TR6 Prodrug Comprising Cholesterol Hemisuccinate ("CHEMS")

In another experiment, an TR6 Prodrug comprising cholesterol hemisuccinate ("CHEMS") was synthesized in the following manner. Briefly, a solution of cholesterol hemisuccinate (2.68 g, 5.50 mmol, 1.00 eq) in DMF (150 mL) was added $Ag_2CO_3$ (2.27 g, 8.25 mmol, 374 uL, 1.50 eq) at 25° C. The reaction mixture was stirred at 25° C. for 0.5 hr. Then compound 2 (2.50 g, 5.50 mmol, 1.00 eq) and NaI (1.24 g, 8.25 mmol, 1.50 eq) were added to the mixture. After addition, the reaction mixture was stirred at 80° C. for 12 hrs. LCMS showed that the reaction was completed, and the desired mass (RT=1.465 mins) was detected. The reaction mixture was cooled to 25° C. and filtered through a pad of celite and washed with DMF (200 mL). The filtrate was concentrated at 50° C. to give the crude product, which was purified by reverse-MPLC (TFA condition) and then concentrated under reduced pressure to give the crude product. The crude product was combined with EW15710-150-P1 (~700 mg) to purified by column chromatography ($SiO_2$, Petroleum ether: Ethyl acetate=5:1 to 2:1, $R_f$=0.6), which was detected by TLC (Petroleum ether: Ethyl acetate=1:1, $R_f$=0.6, PMA). Target 1 (1.80 g, 1.97 mmol, 29.8% yield, 99.0% purity) was obtained as a yellow solid, which was confirmed by $^1$H NMR, $^{19}$F NMR, LCMS, HPLC, SFC, and DSC. The resulting compound(s) are shown in FIG. 7.

Example 5: Chemical Synthesis of TR3 Prodrug Comprising Stearic Acid

In another experiment, a TR3 Prodrug comprising stearic acid was synthesized in the following manner. Briefly, to a solution of compound 4 (9.86 g, 15.9 mmol, 94.7% purity, 1.00 eq) in $CHCl_3$ (100 mL) was added m-CPBA (4.86 g, 23.9 mmol, 85.0% purity, 1.50 eq) in portions. Then, the mixture was stirred at 80° C. for five (5) hrs. LCMS showed 6.01% of compound 4 (Retention Time=1.041 mins) was remained and desired mass (Retention Time=1.149 mins) was detected. Then $NH_3.H_2O$ (107 g, 920 mmol, 118 mL, 30% purity, 57.6 eq) was added and the mixture was stirred at 15° C. for thirty (30) mins. Finally, TosCl (3.65 g, 19.1 mmol, 1.20 eq) was added in one portion. The mixture was stirred at 15° C. for twelve (12) hrs. LCMS showed that compound 4 was consumed and the desired mass (RT=1.049 mins) was detected. The reaction mixture was separated by separating funnel. The aqueous phase was extracted with DCM (100 mL*2). The combined organic phase was washed with brine (100 mL), dried over $Na_2SO_4$, filtered, and concentrated under vacuum. The crude product combination was purified by prep-HPLC (column: Welch Ultimate XB-SiOH 250*50*10 um; mobile phase: [Hexane-EtOH (0.1% $NH_3$ $H_2O$)]; B %: 1%-40%, 20 min) and further purified by MPLC ($SiO_2$, Dichloromethane/Methanol=1/0 to 100/1, Dichloromethane/Methanol=10/1, $R_f$=0.35). The Target A (485.61 mg, 767 μmol, 4.33% yield, 94.8% purity) was obtained as off-white solid, which was confirmed by $^1$H NMR, LCMS, and HPLC. The resulting compound(s) are shown in FIG. 8.

Example 6: Synthesis and Characterization of LNP-TR6 Liposome

A liposome comprising the TR6 prodrug (denoted LNP-TR6) was synthesized and characterized using a microfluidics technique performed on a NanoAssemblr Bench top instrument (Precision NanoSystems) in the following manner. Briefly, a stock solution of each lipid component; Hydro Soy PC[(HSPC: L-α-phosphatidylcholine, hydrogenated (Soy)], Cholesterol, DSPE-PEG (1,2-distearoyl-sn-glycero-3-phosphoethanolamine-N-[amino(polyethylene glycol)-2000], and TR6 were prepared in ethanol at the concentration of 20 mg/ml. Each of the lipid components (HSPC, CHOL, DSPE-PEG, and TR6) were mixed together in a molar ratio of 40:31:26:3 to synthesize LNP-TR6. The size of the LNP-TR6 depend on various parameter(s) such as flow rate, temperature, and concentration of the lipid mixture. The optimized ratio of the lipid mixture at the molar ratio of 40:31:26:3 was preheated at 50° C. using the heating block attachment in the microfluidizer. The aqueous phase containing 1 mM PBS buffer was also preheated at 50° C. before passing through the microfluidics cartridge at the flow rate of 3:1 (aqueous: organic phase, lipid mixture). The solvent was removed using dialysis membrane of cut off 12 KDa size (Sigma Aldrich) against DI water for at least twenty-four (24) hrs. The DI water was changed at least five (5) times during the period of twenty-four (24) hrs. to maximize the removal of the solvent. After the removal of the solvent, the LNP-TR6 was concentrated according to the need using Amicon centrifugal filtration device (cut off size 10 KDa, at 3000 g).

Characterization of the LNP-TR6 liposome was determined using a Malvern Zetasizer (Malvern Instrumentation Co., Westborough, Mass., USA). Two (2) ml of LNP-TR6 liposomes (concentration of the liposome was of 0.5-1 mg/ml) was placed in a 4-sided, clear, plastic cuvette and analyzed directly at 25° C. The results shown in FIG. 9 show the Zav size of the nanoparticles were approximately 83 nm with a PDI of approximately 0.164.

Additionally. Zeta potential of the LNP-TR6 liposomes in aqueous dispersion was determined using a Malvern zeta seizer Instrument (Malvern Instrumentation Co, Westborough, Mass., USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-TR6 was approximately −16.2 mV (FIG. 10).

Example 7: Synthesis and Characterization of LNP-TR5 Liposome

In another experiment, a liposome comprising the TR5 prodrug (denoted LNP-TR5) was synthesized and characterized using a microfluidics technique performed on a NanoAssemblr Bench top instrument (Precision NanoSystems) in the following manner. Briefly, a stock solution of each lipid component; Hydro Soy PC[(HSPC: L-α-phosphatidylcholine, hydrogenated (Soy)], Cholesterol, DSPE-PEG (1,2-distearoyl-sn-glycero-3-phosphoethanolamine-N-[amino(polyethylene glycol)-2000], and TR5 were prepared in ethanol at the concentration of 10 mg/ml. Each of the lipid components (HSPC, CHOL, DSPE-PEG, and TR5) were mixed together in a molar ratio of 53:33:9:5 to synthesize LNP-TR5. The size of the LNP-TR5 depend on various parameter(s) such as flow rate, temperature, and concentration of the lipid mixture. The optimized ratio of the lipid mixture at the molar ratio of 53:33:9:5 was preheated at 45° C. using the heating block attachment in the microfluidizer. The aqueous phase containing 1 mM PBS buffer was also preheated at 45° C. before passing through the microfluidics cartridge at the flow rate of 3.5:1 (aqueous: organic phase, lipid mixture). The solvent was removed using dialysis membrane of cut off 12 KDa size (Sigma Aldrich) against DI water for at least twenty-four (24) hrs. The DI water was changed at least five (5) times during the period of twenty-four (24) hrs. to maximize the removal of the solvent. After the removal of the solvent, the LNP-TR6 was concentrated according to the need using Amicon centrifugal filtration device (cut off size 10 KDa, at 3000 g).

Characterization of the LNP-TR5 liposome was determined using a Malvern Zetasizer (Malvern Instrumentation Co., Westborough, Mass., USA). Two (2) ml of LNP-TR5 liposomes (concentration of the liposome was of 0.5-1 mg/ml) was placed in a 4-sided, clear, plastic cuvette and analyzed directly at 25° C. The results shown in FIG. 11 show the Zav size of the nanoparticles were approximately 85 nm with a PDI of approximately 0.096.

Additionally, Zeta potential of the LNP-TR5 liposomes in aqueous dispersion was determined using a Malvern zeta seizer Instrument (Malvern Instrumentation Co, Westborough, Mass., USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-TR5 was approximately −13.1 mV (FIG. 12).

Example 8: Synthesis and Characterization of LNP-TR3 Liposome

In another experiment, a liposome comprising the TR3 prodrug (denoted LNP-TR3) was synthesized and characterized using a microfluidics technique performed on a NanoAssemblr Bench top instrument (Precision NanoSystems) in the following manner. Briefly, a stock solution of each lipid component; HSPC, Cholesterol, DSPE-PEG was prepared in ethanol at a concentration of 20 mg/ml. The TR3 prodrug was prepared in ethanol at the concentration of 2 mg/ml. Each of the lipid components (HSPC, CHOL, DSPE-PEG, and TR3) were mixed together in a molar ratio of 53.5:33.5:6:5 and then diluted with ethanol to obtain a lipid concentration of approximately 9 mg/ml to synthesize LNP-TR3. The size of the LNP-TR3 depend on various parameter(s) such as flow rate, temperature, and concentration of the lipid mixture. The optimized ratio of the lipid mixture at the molar ratio of 53.5:33.5:6:5 was preheated at 45° C. using the heating block attachment in the microfluidizer. The aqueous phase containing 1 mM PBS buffer was also preheated at 45° C. before passing through the microfluidics cartridge at the flow rate of 3.5:1 (aqueous: organic phase, lipid mixture). The solvent was removed using dialysis membrane of cut off 12 KDa size (Sigma Aldrich) against DI water for at least twenty-four (24) hrs. The DI water was changed at least five (5) times during the period of twenty-four (24) hrs. to maximize the removal of the solvent. After the removal of the solvent, the LNP-TR3 was concentrated according to the need using Amicon centrifugal filtration device (cut off size 10 KDa, at 3000 g).

Characterization of the LNP-TR3 liposome was determined using a Malvern Zetasizer (Malvern Instrumentation Co., Westborough, Mass., USA). Two (2) ml of LNP-TR3 liposomes (concentration of the liposome was of 0.5-1 mg/ml) was placed in a 4-sided, clear, plastic cuvette and analyzed directly at 25° C. The results shown in FIG. 13 show the Zav size of the nanoparticles were approximately 88 nm with a PDI of approximately 0.125.

Additionally, Zeta potential of the LNP-TR3 liposomes in aqueous dispersion was determined using a Malvern zeta seizer Instrument (Malvern Instrumentation Co, Westborough, Mass., USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-TR3 was approximately −13.2 mV (FIG. 14).

Example 9: Synthesis and Characterization of LNP-TR8 Liposome

In another experiment, a liposome comprising the TR8 prodrug (denoted LNP-TR8) was synthesized and characterized using a microfluidics technique performed on a NanoAssemblr Bench top instrument (Precision NanoSystems) in the following manner. Briefly, a stock solution of each lipid component; HSPC, Cholesterol, DSPE-PEG was prepared separately. MPLA (PHAD®) Monophosphoryl Lipid A (Synthetic) (PHAD) stock solution was prepared in dimethyl sulfoxide (10 mg/ml). Each of the lipid components (HSPC, CHOL, DSPE-PEG, and MPLA) were mixed together in a molar ratio of 55:37.5:3 and then diluted with ethanol to obtain a lipid concentration of approximately 10 mg/ml. The size of the LNP-TR8 depend on various parameter(s) such as flow rate, temperature, and concentration of the lipid mixture. The optimized ratio of the lipid mixture at the molar ratio of 55:37:5:3 was preheated at 45° C. using the heating block attachment in the microfluidizer. The aqueous phase containing 1 mM PBS buffer was also preheated at 45° C. before passing through the microfluidics cartridge at the flow rate of 5:1 (aqueous: organic phase, lipid mixture). The solvent was removed using dialysis membrane of cut off 12 KDa size (Sigma Aldrich) against DI water for at least twenty-four (24) hrs. The DI water was changed at least five (5) times during the period of twenty-four (24) hrs. to maximize the removal of the solvent. After the removal of the solvent, the LNP-TR8 was concentrated according to the need using Amicon centrifugal filtration device (cut off size 10 KDa, at 3000 g).

Characterization of the LNP-TR8 liposome was determined using a Malvern Zetasizer (Malvern Instrumentation Co., Westborough, Mass., USA). Two (2) ml of LNP-TR8 liposomes (concentration of the liposome was of 0.5-1 mg/ml) was placed in a 4-sided, clear, plastic cuvette and analyzed directly at 25° C. The results shown in FIG. 15 show the Zav size of the nanoparticles were approximately 89 nm with a PDI of approximately 0.240.

Additionally, Zeta potential of the LNP-TR8 liposomes in aqueous dispersion was determined using a Malvern zeta seizer Instrument (Malvern Instrumentation Co, Westborough, Mass., USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-TR8 was approximately −9.8 mV (FIG. 16).

Example 10: Synthesis and Characterization of LNP-ID3-TR8 Liposome

In another experiment, a liposome comprising the ID3 prodrug and the TR8 prodrug (denoted LNP-ID3-TR8) was synthesized and characterized using a microfluidics technique performed on a NanoAssemblr Bench top instrument (Precision NanoSystems) in the following manner. Briefly, a stock solution of each lipid component; HSPC, Cholesterol, DSPE-PEG was prepared in ethanol at a concentration of 20 mg/ml. Meanwhile, a stock solution of ID3 prodrug (20 mg/mi) was prepared in acetonitrile, while a stock solution of MPLA (10 mg/ml) was prepared in DSMO. Each of the lipid components (HSPC, CHOL, DSPE-PEG, ID3, and MPLA) were mixed together in a molar ratio of 54:28:12:3:3 and then diluted with ethanol to obtain a lipid concentration of approximately 10 mg/ml. The size of the LNP-ID3-TR8 depend on various parameter(s) such as flow rate, temperature, and concentration of the lipid mixture. The optimized ratio of the lipid mixture at the molar ratio of 54:28:12:3:3 was preheated at 45° C. using the heating block attachment in the microfluidizer. The aqueous phase containing 1 mM PBS buffer was also preheated at 45° C. before passing through the microfluidics cartridge at the flow rate of 3:1 (aqueous: organic phase, lipid mixture). Accordingly, the liposome formulation was synthesized in such a way so that the molar ratio of ID3:TR8 remain at a 4:1 ratio. The solvent was removed using dialysis membrane of cut off 12 KDa size (Sigma Aldrich) against DI water for at least twenty-four (24) hrs. The DI water was changed at least five (5) times during the period of twenty-four (24) hrs. to maximize the removal of the solvent. After the removal of the solvent, the LNP-TR8 was concentrated according to the need using Amicon centrifugal filtration device (cut off size 10 KDa, at 3000 g).

Characterization of the LNP-ID3-TR8 liposome was determined using a Malvern Zetasizer (Malvern Instrumentation Co., Westborough, Mass., USA). Two (2) ml of LNP-ID3-TR8 liposomes (concentration of the liposome was of 0.5-1 mg/ml) was placed in a 4-sided, clear, plastic cuvette and analyzed directly at 25° C. The results shown in FIG. 17 show the Zav size of the nanoparticles were approximately 82 nm with a PDI of approximately 0.170.

Additionally, Zeta potential of the LNP-ID3-TR8 liposomes in aqueous dispersion was determined using a Malvern zeta seizer Instrument (Malvern Instrumentation Co, Westborough, Mass., USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-ID3-TR8 was approximately −11.9 mV (FIG. 18).

Example 11: Tumor Inhibition of LNP-TR5 in Combination with LNP-DOX Using B16F10 Cells In Vivo Evaluation of LNP-TR5 in combination with LNP-DOX was performed using the following protocols. Briefly, murine melanoma cancer B16F10 cells ($0.2 \times 10^6$) were inoculated subcutaneously in the right rear flank region of C57BL/6 mice. Animals were treated with vehicle control, LNP-DOX (Doxorubicin in liposome form) at 3 mg/kg, and combination of LNP-DOX at 3 mg/kg and LNP-TR5 at 1 mg/kg, two times weekly through i.v injection. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day twenty (20).

The results show treatment with LNP-DOX alone produces a significant tumor growth inhibition. The TGI was calculated at 66.37% ($p<0.01$) when compared with the vehicle treated group. Additionally, combination LNP-TR5 and LNP-DOX also produced significant anti-tumor activity. The TGI was calculated at 52.73% ($p<0.05$). (See, FIG. 19).

Example 12: Tumor Inhibition of LNP-TR6 in Combination with LNP-NK1 and LNP-TR6 in Combination with LNP-TR8 and LNP-MTO Using B16F10 Cells In Vivo Evaluation of LNP-TR6 in combination with LNP-NK1 and LNP-TR6 was performed using the following protocols. Briefly, murine melanoma cancer B16F10 cells ($0.2 \times 10^6$) were inoculated subcutaneously in the right rear flank region of C57BL/6 mice. Animals were treated with vehicle control, LNP-MTO (Mitoxantrone dihydrochloride in liposome form) at 2 mg/kg, combination of LNP-TR6 at 3 mg/kg and LNP-NK1 (KRN7000 in liposome form) at 0.03 mg/kg, and combination of LNP-TR6 at 2 mg/kg, LNP-TR8 at 0.6 mg/kg and LNP-MTO at 2 mg/kg, two times weekly through i.v injection. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day eighteen (18).

The results show that treatment with LNP-TR6+LNP-NK1 and LNP-TR6+LNP-TR8+LNP-MTO produce a significant tumor growth inhibition, when compared to vehicle treated group. The TGIs were calculated at 49.87% and 57.02%, respectively ($p<0.01$). (See, FIG. 20).

Example 13: Tumor Inhibition of LNP-TR5 and LNP-TR6 in Combination with LNP-AR5 Using B16F10 Cells In Vivo Evaluation of LNP-TR6 in combination with LNP-AR5 and LNP-TR5 in combination with LNP-AR5 was performed using the following protocols. Briefly, murine melanoma cancer B16F10 cells ($0.2 \times 10^6$) were inoculated subcutaneously in the right rear flank region of C57BL/6 mice. Animals were treated with vehicle control, LNP-AR5 (ZM241385-Stearic Acid in liposome form) at 3 mg/kg, combination of LNP-AR5 and LNP-TR6 at 3 mg/kg and combination of LNP-AR5 and LNP-TR5 at 3 mg/kg two times weekly through i.v injection. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day fifteen (15).

The results show treatment with LNP-AR5+LNP-TR5 produces significant anti-tumor activities. The TGI was calculated at 30.72% (all p<0.05) when compared to vehicle treated group. Insignificant anti-tumor activities were observed in LNP-AR5 and LNP-AR5+LNP-TR6 groups. TGIs were calculated at 14.86% and 21.52%, respectively. (See, FIG. 21).

Example 14: Tumor Inhibition of LNP-TR5 in Combination with LNP-AR5 and LNP-DOX Using EMT6 Cells In Vivo Evaluation of LNP-TR5 in combination with LNP-AR5 and LNP-DOX was performed using the following protocols. Briefly, murine breast cancer EMT6 cells ($0.1 \times 10^6$) were inoculated subcutaneously in the right rear flank region of Balb/c mice. Animals were treated with vehicle control, Doxorubicin (LNP-DOX) at 3 mg/kg, and combination of LNP-DOX+LNP-AR5+LNP-TR5 at 3 mg/kg through i.v injection. After receiving two (2) doses of LNP-DOX, the LNP-DOX treatment was replaced with vehicle. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day twenty-one (21).

The results show, treatment of LNP-DOX alone at 3 mg/kg for two (2) doses in one (1) week produces significant anti-tumor activity. The TGI was calculated at 68.74% (p<0.05) when compared to vehicle treated group. Additionally, improved anti-tumor activities were observed when combining the LNP-DOX treatment with LNP-AR5+LNP-TR5. The TGI was at 87.92%, (all p<0.05). (See, FIG. 22).

Example 15: Tumor Inhibition Studies of LNP-TR5 and LNP-TR6 in Multiple Combination(s) Using H22 Cells In Vivo Evaluation of LNP-TR5 and LNP-TR6 in a plurality of combination(s) was performed using the following protocols. Briefly, hepatocellular carcinoma H22 cells ($1 \times 10^6$) were inoculated subcutaneously in the right rear flank region of Balb/c mice. Animals were treated with vehicle control, anti-PD1 antibody at 10 mg/kg, combination of LNP-AR5 at 4 mg/kg and LNP-TR5 at 4 mg/kg for the first two (2) doses and 2 mg/kg for the remainder of the study, combination of LNP-AR5 and LNP-TR6 at 4 mg/kg, combination of anti-PD1 antibody at 10 mg/kg, LNP-AR5 at 4 mg/kg and LNP-TR5 at 4 mg/kg for the first two (2) doses and 2 mg/kg for the remainder of the study, and combination of LNP-ID3, LNP-AR5 at 3 mg/kg for first two (2) doses and 3.5 mg/kg for the remainder of the study, and LNP-TR5 at 3 mg/kg for the first two (2) doses and 2 mg/kg for the remainder of the study through i.v. injection. Tumor volumes were measured 3 times in two dimensions using a caliper, and the volume was calculated using the formula: $V=(L \times W \times W) \times 0.5$, where V is tumor volume, L is tumor length (the longest tumor dimension) and W is tumor width (the longest tumor dimension perpendicular to L). The tumor growth inhibition (TGI) was calculated based on the tumor size data of day fourteen (14).

The results show that treatment with Anti-PD-1+LNP-AR5+LNP-TR5 produces significant anti-tumor activities. The TGI was calculated at 74.98% (all p<0.05) when compared to vehicle treated group. Insignificant anti-tumor activity was observed in LNP-AR5+LNP-TR5, and LNP-ID3+LNP-AR5+LNP-TR5. The TGIs were calculated at 55.8%, and 48.83%, respectively. (See, FIG. 23).

Example 16: Tumor Inhibition Studies of LNP-TR5 and LNP-TR6 in Multiple Combination(s) in Colorectal Cancer Cells In Vivo Evaluation of LNP-TR5 and LNP-TR6 in a plurality of combination(s) was performed using the following protocols, Briefly, colorectal cancer cells ($1 \times 10^6$) were inoculated subcutaneously in the right rear flank region of C57BL/6 mice. Animals were treated with vehicle control, Doxorubicin (LNP-DOX) at 4 mg/kg, anti-PD1 antibody at 10 mg/kg, combination of LNP-AR5 at 4 mg/kg and LNP-TR5 at 4 mg/kg for the first two (2) doses and 2 mg/kg for the remainder of the study, a combination of LNP-AR5 and LNP-TR6 at 4 mg/kg, a combination of LNP-DOX, LNP-AR5 and LNP-TR6 at 4 mg/kg, a combination of LNP-DOX, LNP-AR5 at 4 mg/kg and LNP-TR5 at 4 mg/kg for the first two (2) doses and 2 mg/kg for the remainder of the study, a combination of anti-PD1 antibody at 10 mg/kg, LNP-AR5 at 4 mg/kg and LNP-TR5 at 4 mg/kg for the first two (2) doses and 2 mg/kg for the remainder of the study, and a combination of LNP-ID3 and LNP-AR5 at 3 mg/kg for first two (2) doses and 3.5 mg/kg for the remainder of the study, and LNP-TR5 at 3 mg/kg for the first two (2) doses and 2 mg/kg for the remainder of the study through i.v. injection.

The study further included a dosing regimen wherein the groups receiving a dose of LNP-DOX, the first doses included solely LNP-DOX and subsequently the LNP-DOX was halted and mice were dosed with other drugs.

Tumor volumes were measured three (3) times in two dimensions using a caliper, and the volume was calculated using the formula: $V=(L \times W \times W) \times 0.5$, where V is tumor volume, L is tumor length (the longest tumor dimension) and W is tumor width (the longest tumor dimension perpendicular to L). The tumor growth inhibition (TGI) was calculated based on the tumor size data of day nineteen (19).

The results show that treatment of LNP-DOX alone at 4 mg/kg produces significant anti-tumor activity. The TGI was calculated at 74.39% (p<0.05) when compared to vehicle treated group. Additionally, combination treatment with LNP-AR5+LNP-TR5+LNP-DOX followed by LNP-AR5+LNP-TR6+LNP-DOX followed by LNP-AR5+LNP-TR5+Anti-PD-1+LNP-AR5+LNP-TR5, and LNP-ID3+LNP-AR5+LNP-TR5 also produce significant anti-tumor activities. The TGIs were calculated at 77.35%, 90.31%, 87.67%, 91.33% and 73.77% (all p<0.05), respectively. (See, FIG. 24).

Example 17: In Vitro Validation of TR6 Prodrug in Liposome Form Mechanism of Action To confirm in vitro biological activity of LNP-TR6 and to further confirm targeting of TLR1/2, the following experiment(s) were performed using a RAW-Blue™ Cells and QUANTI-Blue™ assay (InvivoGen, San Diego, Calif.). Briefly, Raw Blue™ cells that express human Toll Like Receptors (TLRs) (with the exception of TLR5) and an NF-κB/AP-1-inducible SEAP (secreted embryonic alkaline phosphatase) reporter gene were used. Stimulation of these cells with TR6 lead to NF-κB activation through TLR1/2 which is measured by detection of SEAP levels. RAW-Blue™ Cells were incubated with TR6 and LNP-TR6 at different concentration. After twenty-four (24) hr. incubation with the compounds, TLR stimulation was assessed by measuring the levels of SEAP optimal density (OD) using a QUANTI-Blue™ assay. ODs were normalized to the control (untreated) group. The result showed that treating the cells with TR6 and LNP-TR6 could cause stimulation of TLR1/2 confirming the mechanism of action of TR6 and its activity in LNP form, (See, FIG. 25).

Example 18: In Vitro Validation of TR8 Prodrug in Liposome Form Mechanism of Action In another experiment, in vitro biological activity of LNP-TR8 and to further confirm targeting of TLR4, the following experiment(s) were performed using a RAW-Blue™ Cells and QUANTI-Blue™ assay (InvivoGen, San Diego, Calif.). Briefly, Raw Blue™ cells that express human Toll Like Receptors (TLRs) (with the exception of TLR5) and an NF-κB/AP-1-inducible SEAP (secreted embryonic alkaline phosphatase) reporter gene were used. Stimulation of these cells with TR8 lead to NF-κB activation through TLR4 which is measured by detection of SEAP levels. RAW-Blue™ Cells were incubated with TR8 and LNP-TR8 at different concentration. After twenty-four (24) hr. incubation with the compounds, TLR stimulation was assessed by measuring the levels of SEAP optimal density (OD) using a QUANTI-Blue™ assay. ODs were normalized to the control (untreated) group. The result showed that treating the cells with TR8 and LNP-TR8 could cause stimulation of TLR4 confirming the mechanism of action of TR8 and its activity in LNP form. (See, FIG. 26).

Example 19: In Vitro Validation of TR5 Prodrug in Liposome Form Mechanism of Action In another experiment, in vitro biological activity of LNP-TR5 and to further confirm targeting of TLR7/8, the following experiment(s) were performed using a RAW-Blue™ Cells and QUANTI-Blue™ assay (InvivoGen, San Diego, Calif.). Briefly, Raw Blue™ cells that express human Toll Like Receptors (TLRs) (with the exception of TLR5) and an NF-κB/AP-1-inducible SEAP (secreted embryonic alkaline phosphatase) reporter gene were used. Stimulation of these cells with TR5 lead to NF-κB activation through TLR7/8 which is measured by detection of SEAP levels. RAW-Blue™ Cells were incubated with TR5 and LNP-TR5 at different concentration. After twenty-four (24) hr. incubation with the compounds, TLR stimulation was assessed by measuring the levels of SEAP optimal density (OD) using a QUANTI-Blue™ assay. ODs were normalized to the control (untreated) group. The result showed that treating the cells with TR5 and LNP-TR5 could cause stimulation of TLR7/8 confirming the mechanism of action of TR5 and its activity in LNP form. (See, FIG. 27).

Example 20: In Vitro Validation of TR3 Prodrug in Liposome Form Mechanism of Action In another experiment, in vitro biological activity of LNP-TR3 and to further confirm targeting of TLR7 and not targeting TLR8, the following experiment(s) were performed using a RAW-Blue™ Cells and QUANTI-Blue™, HEK-Blue™, and hTLR8 cell line assay (InvivoGen, San Diego, Calif.). Briefly, despite Raw Blue™ cells that express a variety of human Toll Like Receptors (TLRs) (including TLR7/8 but with the exception of TLR5) hTLR8 cells dominantly oxproεε the human TLR8. Additionally, an NF-κB/AP-1-inducible SEAP (secreted embryonic alkaline phosphatase) reporter gene were used. Stimulation of these cells with TR3 lead to NF-κB activation through TLR8 which is measured by detection of SEAP levels.

RAW-Blue™ Cells were incubated with TR5, LNP-TR5, TR3, TR3+Stearic Acid, and LNP-TR3 at different concentration. After twenty-four (24) hr. incubation with the compounds, TLR stimulation was assessed by measuring the levels of SEAP optimal density (OD) using a QUANTI-Blue™ assay. ODs were normalized to the control (untreated) group. The results show both TR5 and TR3 in prodrug and liposome form stimulated TLRs in RAW-Blue™ cells. (See, FIG. 28).

Furthermore, HEK-Blue™ TLR8 Cells were incubated with TR5, LNP-TR5, TR3, TR3+Stearic Acid, and LNP-TR3 at different concentration. After twenty-four (24) hr. incubation with the compounds, TLR stimulation was assessed by measuring the levels of SEAP optimal density (OD) using a QUANTI-Blue™ assay. ODs were normalized to the control (untreated) group. The results show that only TR5 in prodrug and liposome form were able to stimulate the cells. (See, FIG. 29).

Taken together, these results show that since TR5 is a TLR7/8 agonist, TR5 and TR5 in liposome form stimulate TLR7 and TLR8. However, TR3 can only stimulate TLR7 and not TLR8. Thus, it is shown that TR3 is specific to TLR7 and not TLR8.

Example 21: Human Clinical Trials for the Treatment of Human Carcinomas Through the Use of Formulated and/or Co-Formulated Liposomes Comprising TLR Prodrugs Formulated and/or co-formulated liposomes containing TLR prodrugs and/or TLR lipid moieties are used in accordance with the present invention which specifically accumulate in a tumor cell and are used in the treatment of certain tumors and other immunological disorders and/or other diseases. In connection with each of these indications, two clinical approaches are successfully pursued.

I.) Adjunctive therapy: In adjunctive therapy, patients are treated with formulated and/or co-formulated liposomes containing TLR prodrugs in combination with a chemotherapeutic or pharmaceutical or biopharmaceutical agent or a combination thereof. Primary cancer targets are treated under standard protocols by the addition of formulated and/or co-formulated liposomes containing TLR prodrugs. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the formulated and/or co-formulated liposomes containing TLR prodrugs in monotherapy of tumors, the formulated and/or co-formulated liposomes containing TLR prodrugs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single formulated and/or co-formulated liposome containing TLR prodrugs may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention is dictated by and directly dependent on (a) the unique characteristics of the formulated and/or co-formulated liposomes containing TLR prodrugs, (b) the individual mechanics of the combination compound, if any, (c) the particular therapeutic or prophylactic effect to be achieved, and (d) the limitations inherent in the art of compounding such a compound for the treatment of sensitivity in individuals.

Clinical Development Plan (CDP)

The CDP follows and develops treatments of using formulated and/or co-formulated liposomes containing TLR prodrugs in connection with adjunctive therapy or monotherapy. Trials initially demonstrate safety and thereafter confirm efficacy in repeat doses. Trials are open label comparing standard chemotherapy and/or the current standard of therapy plus formulated and/or co-formulated liposomes containing TLR prodrugs. As will be appreciated, one non-limiting criteria that can be utilized in connection with enrollment of patients is expression of TLR in a tumor as determined by standard detection methods known in the art.

It is believed that formulated and/or co-formulated liposomes, or any of the embodiments disclosed herein, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Examples of Lipids.

| No. | Abbreviation | Name/Chemical Formula |
|---|---|---|
| 1 | CHOL | Cholesterol |
| 2 | DPPG · Na | 1,2-dipalmitoyl-sn-glycero-3-phospho-(1'-rac-glycerol) (sodium salt) |
| 3 | DMPG · Na | 1,2-dimyristoyl-sn-glycero-3-phospho-(1'-rac-glycerol) (sodium salt) |
| 4 | Lyso PC | 1-decanoyl-2-hydroxy-sn-glycero-3-phosphocholine |
| 5 | (Δ9-Cis) PG | 1,2-dioleoyl-sn-glycero-3-phospho-(1'-rac-glycerol) (sodium salt) |
| 6 | Soy Lyso PC | L-α-lysophosphatidylcholine (Soy) |
| 7 | PG | 1,2-dilauroyl-sn-glycero-3-phospho-(1'-rac-glycerol) (sodium salt) |
| 8 | PA-PEG3-mannose | 1,2-dipalmitoyl-sn-glycero-3-phospho((ethyl-1',2',3'-triazole)triethyleneglycolmannose) (ammonium salt) |
| 9 | C16 PEG2000 Ceramide | N-palmitoyl-sphingosine-1-{succinyl[methoxy(polyethylene glycol)2000]} |
| 10 | MPLA | Monophosphoryl Lipid A |

TABLE II

Examples of Helper Lipids.

| No. | Abbreviation | Name |
|---|---|---|
| 1 | DOTAP | 1,2-dioleoyl-3-trimethylammonium-propane (chloride salt) |
| 2 | DODMA | 1,2-dioleyloxy-3-dimethylaminopropane |
| 3 | DLinDMA | 1,2-dilinoleyloxy-3-dimethylaminopropane |
| 4 | DLin-KC2-DMA | 2,2-dilinoleyl-4-dimethylaminoethyl-[1,3]-dioxolane |
| 5 | Δ9-Cis PE (DOPE) | 1,2-Dioleoyl-sn-glycero-3-phosphoethanolamine |
| 6 | DOPC | 1,2-dioleoyl-sn-glycero-3-phosphocholine |
| 7 | CHOL | Cholesterol |
| 8 | PEG-C-DMA | N-[(methoxy poly(ethylene glycol)2000)carbamyl]-1,2-dimyristyloxlpropyl-3-amine |
| 9 | CHEMS | cholesteryl hemisuccinate |
| 10 | DPPC | 1,2-dipalmitoyl-sn-glycero-3-phosphocholine |

TABLE II-continued

Examples of Helper Lipids.

| No. | Abbreviation | Name |
|---|---|---|
| 11 | DSPC | 1,2-distearoyl-sn-glycero-3-phosphocholine |
| 12 | MO-CHOL | 4-(2-aminoethyl)-morpholino-cholesterolhemisuccinate |

TABLE III

Examples of Phospholipids/Fatty Acids.

No. Name

1. Oleic acid
2. linolenic acid
3. arachidonic acid
4. docosahexaenoic (DHA)
5. Palmitic acid
6. Palmitoleic acid
7. Stearic acid
8. Eicosapentaenoic acid (EPA)
9. DSPE-PEG(2000) Carboxylic Acid (1,2-distearoyl-sn-glycero-3-phosphoethanolamine-N-[carboxy(polyethylene glycol)
10. DOPE-PEG(2000) Carboxylic acid (1,2-dioleoyl-sn-glycero-3-phosphoethanolamine-N-[carboxy(polyethylene glycol)-2000] (sodium salt)

The invention claimed is:

1. A Toll-like receptor (TLR) prodrug composition comprising TR6 as the TLR prodrug, TR6 having the following structure:

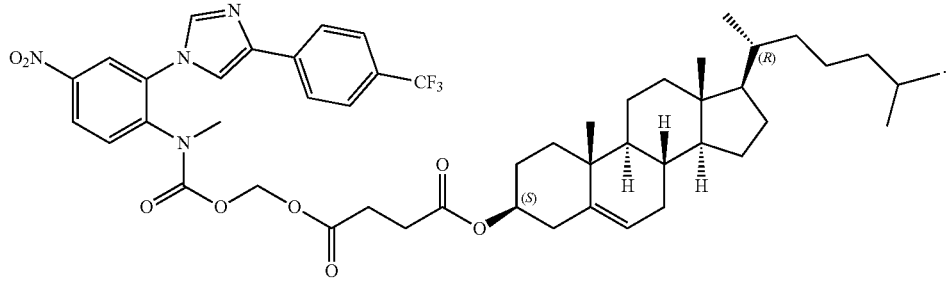

2. A nanocarrier comprising the TLR prodrug of claim 1 whereby the nanocarrier releases an active TLR inhibitor after cleavage of the hydromethylcarbamate linker of TR6.

3. The nanocarrier of claim 2, whereby the nanocarrier is further co-formulated with an iNKT (i-Natural Killer T cell) activator.

4. The nanocarrier of claim 3, wherein the iNKT activator is Alpha-galactosylceramide (α-GalCer).

5. The nanocarrier of claim 2, whereby the nanocarrier is further co-formulated with an immune modulating agent, wherein the immune modulating agent is selected from the group consisting of other TLR agonists and/or prodrugs, immunogenic-cell death inducing chemotherapeutics, IDO (indoleamine 2,3-dioxygenase) antagonists, STING (stimulator of interferon genes protein) agonists, CTLA-4 (cytotoxic T-lymphocyte-associated antigen 4) and inhibitors, PD-1/PD-L1 (programmed cell death 1/programmed cell death ligand 1) inhibitors and/or prodrugs thereof.

6. The nanocarrier of claim 2, whereby the nanocarrier is further co-formulated with an ICD (immunogenic cell death)-inducing chemotherapeutic, wherein the ICD-inducing chemotherapeutic is selected from the group consisting of Doxorubicin (DOX), Mitoxantrone (MTO), Oxaliplatin (OXA), Cyclophosphamide (CP), Bortezomib, Carfilzimib, or Paclitaxel.

7. The nanocarrier of claim 2, further comprising doxorubicin (DOX).

8. The nanocarrier of claim 2, wherein the nanocarrier comprises a liposome.

9. The nanocarrier of claim 2, wherein the nanocarrier comprises a solid-lipid nanoparticle (SLNP).

* * * * *